United States Patent
Deans et al.

(10) Patent No.: US 10,736,911 B2
(45) Date of Patent: Aug. 11, 2020

(54) USE OF A DHODH INHIBITOR IN COMBINATION WITH AN INHIBITOR OF PYRIMIDINE SALVAGE

(71) Applicant: The Board of Trustees of the Leland Stanford Junior University, Stanford, CA (US)

(72) Inventors: Richard Deans, Rocky Mount, NC (US); Ayse Okesli, Stanford, CA (US); David Morgens, Stanford, CA (US); Chaitan Khosla, Palo Alto, CA (US); Michael C. Bassik, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 63 days.

(21) Appl. No.: 16/063,113

(22) PCT Filed: Dec. 22, 2016

(86) PCT No.: PCT/US2016/068365
§ 371 (c)(1),
(2) Date: Jun. 15, 2018

(87) PCT Pub. No.: WO2017/117006
PCT Pub. Date: Jul. 6, 2017

(65) Prior Publication Data
US 2019/0209598 A1    Jul. 11, 2019

Related U.S. Application Data

(60) Provisional application No. 62/272,428, filed on Dec. 29, 2015.

(51) Int. Cl.
| | |
|---|---|
| *A61K 31/7072* | (2006.01) |
| *A61K 45/06* | (2006.01) |
| *A61K 31/519* | (2006.01) |
| *A61P 31/14* | (2006.01) |
| *A61P 35/00* | (2006.01) |
| *A61K 31/404* | (2006.01) |
| *A61K 31/4439* | (2006.01) |
| *A61K 31/52* | (2006.01) |

(52) U.S. Cl.
CPC ........ *A61K 31/7072* (2013.01); *A61K 31/404* (2013.01); *A61K 31/4439* (2013.01); *A61K 31/519* (2013.01); *A61K 31/52* (2013.01); *A61K 45/06* (2013.01); *A61P 31/14* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 2003/0166201 A1* | 9/2003 | Jensen | C12N 9/0006 435/191 |
| 2011/0206689 A1 | 8/2011 | Hahn et al. | |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
"Analog" in Saunders Comprehensive Veterinary Dictionary, 3 ed. © 2007 Elsevier, Inc., retrieved from http://medical-dictionary.thefreedictionary.com/analog on Apr. 19, 2016 (Year: 2007).*
Lossani, A., Torti, A., Gatti, S., Bruno, A., Maserati, R., Wright, G. E., & Focher, F. (2009). Thymidine kinase and uridine-cytidine kinase from Entamoeba histolytica: cloning, characterization, and search for specific inhibitors. Parasitology, 136(6), 595-602. (Year: 2009).*
Munier-Lehmann et al., "On Dihydroorotate Dehydrogenases and Their Inhibitors and Uses", Journal of Medicinal Chemistry, Apr. 25, 2013, pp. 3148-3167, vol. 56, No. 8, Washington, DC.
Noguchi et al., "Synthesis of carbocyclic pyrimidine nucleosides and their inhibitory activities against Plasmodium falciparum thymidylate kinase", Parasitology International, Aug. 2013, pp. 368-371, vol. 62, Issue 4, Elsevier, New York City, NY.
Weber et al., "Salvage capacity of hepatoma 3924A and action of dipyridamole", Advances in Enzyme Regulation, 1983, pp. 53-69, vol. 21, Elsevier, New York City, NY.

* cited by examiner

*Primary Examiner* — Dale R Miller
(74) *Attorney, Agent, or Firm* — Pamela J. Sherwood; Bozicevic, Field & Francis LLP

(57) ABSTRACT

Compounds and methods are provided for the treatment of pathogenic virus infections or cancer. The formulations combine an inhibitor of de novo pyrimidine synthesis, and an inhibitor of a pyrimidine salvage pathway enzyme.

14 Claims, 15 Drawing Sheets
(12 of 15 Drawing Sheet(s) Filed in Color)
Specification includes a Sequence Listing.

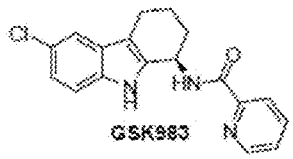
FIG. 1A
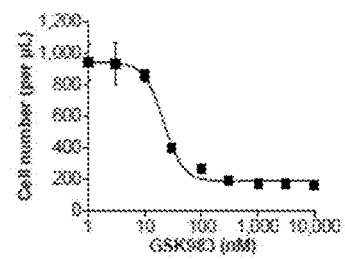
FIG. 1B
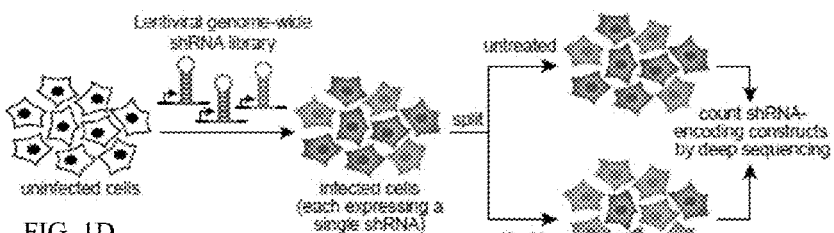
FIG. 1C
FIG. 1D
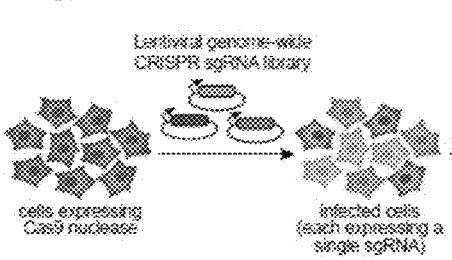
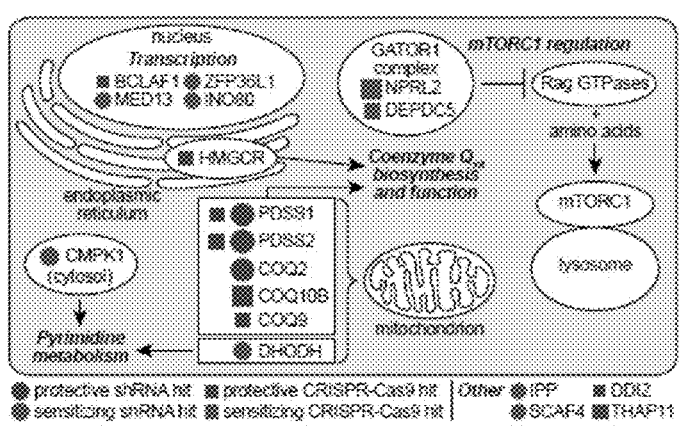
FIG. 1E
FIG. 1F
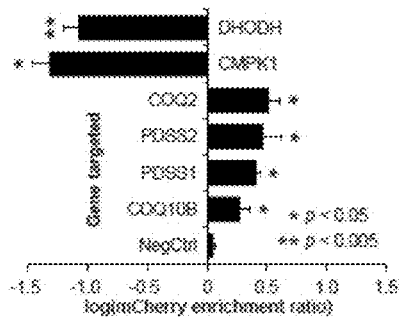
FIG. 1G
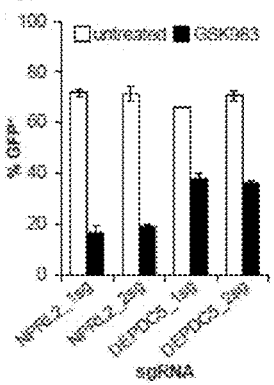
FIG. 1H
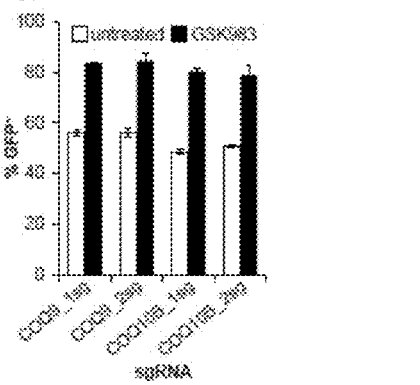
FIG. 1I FIG. 2A
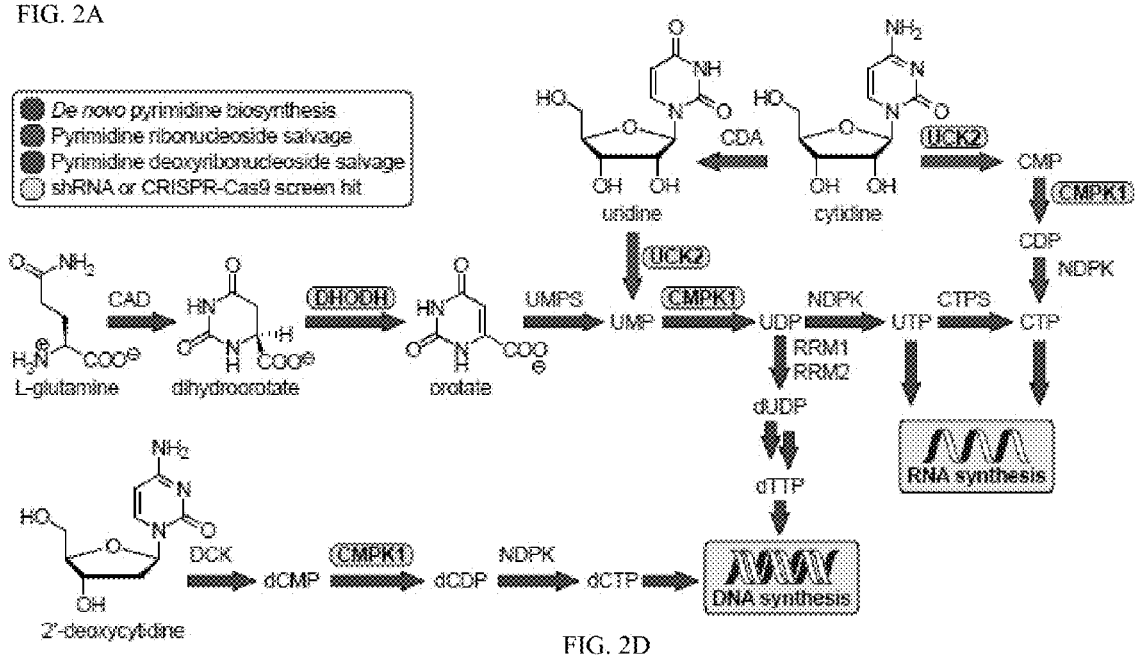
FIG. 2B
FIG. 2C
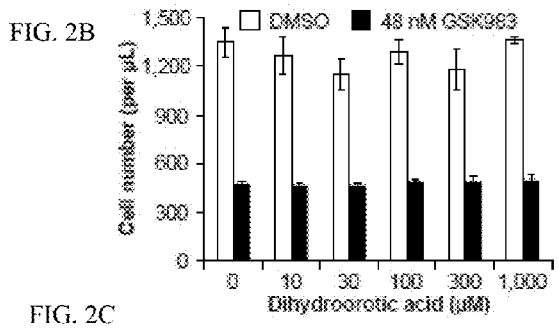
FIG. 2D
| Compound | $K_i$ (nM) | $IC_{50}$ for HPV-16 inhibition (nM)* |
|---|---|---|
| teriflunomide | 156 (31) | not reported |
| GSK983 | 483 (23) | 5 |
| 6Br-pF | 536 (114) | 44 |
| 6Br-oTol | 10,080 (2,000) | 580 |
| GSK984 | 68,000 (12,000) | 9,000 |
*Reported by GlaxoSmithKline
FIG. 2E
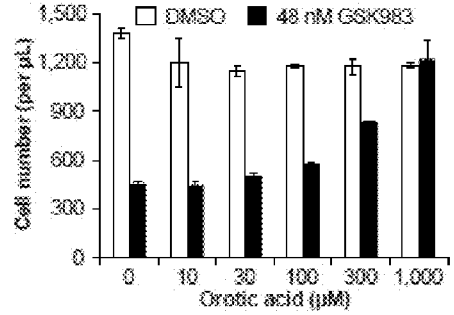
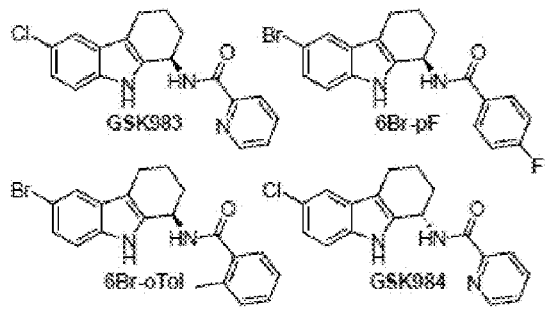

FIG. 4A
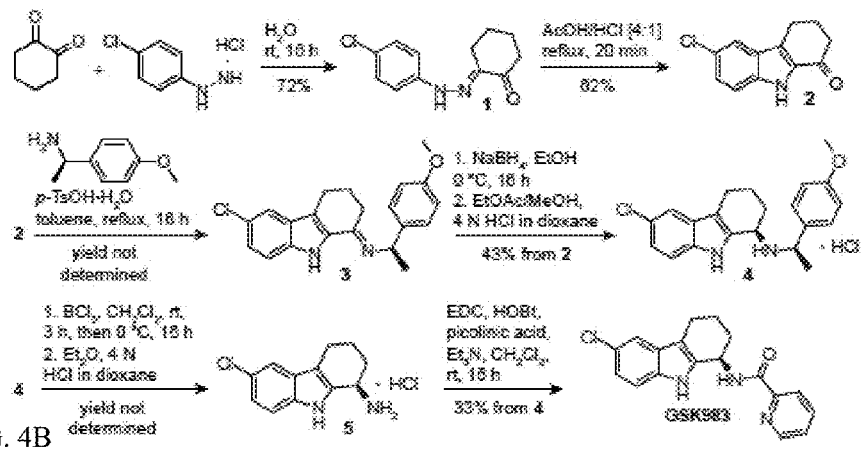
FIG. 4B
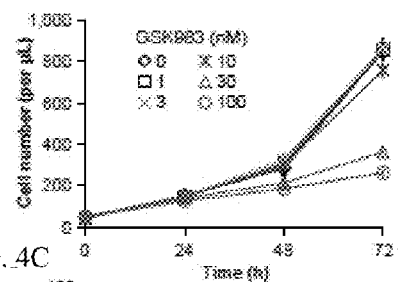
FIG. 4C
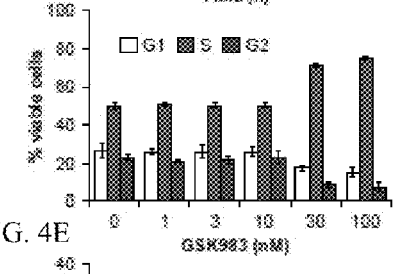
FIG. 4D
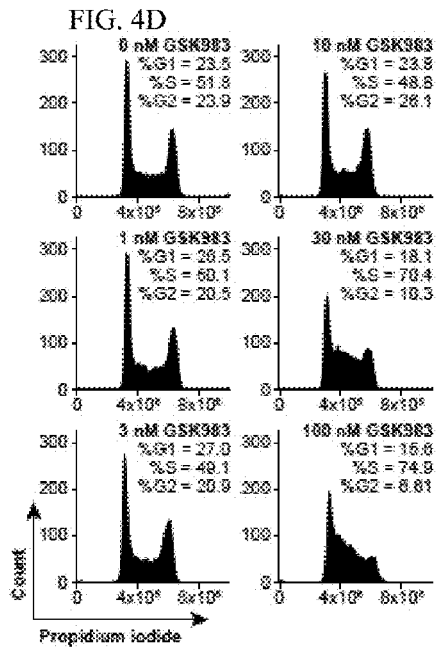
FIG. 4E
FIG. 4F
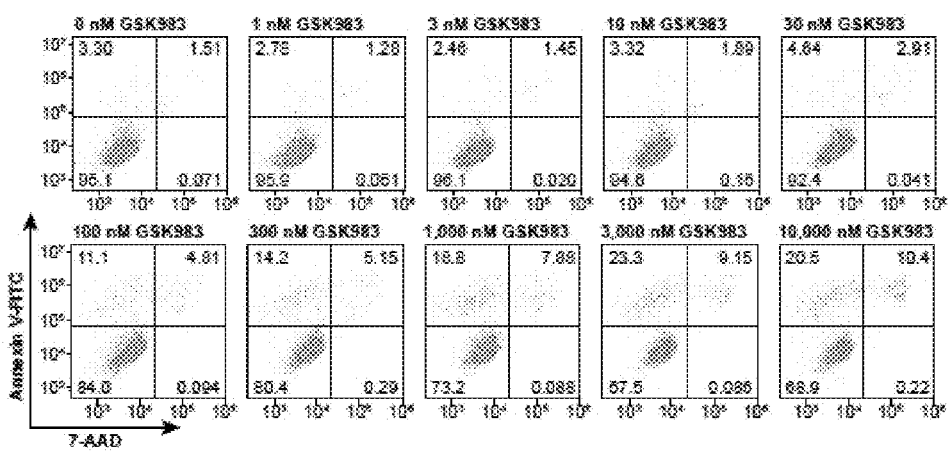

FIG. 6A
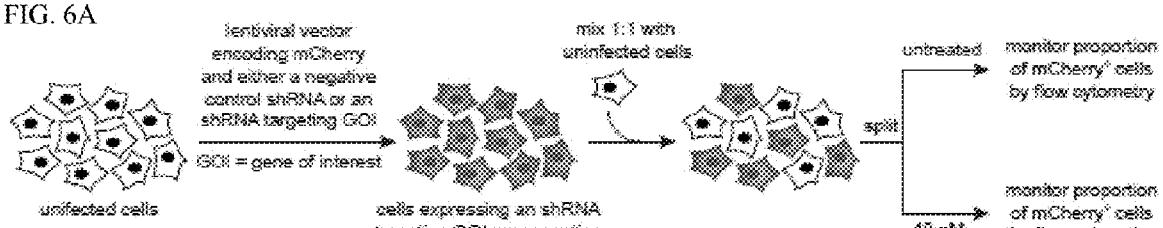
FIG. 6B
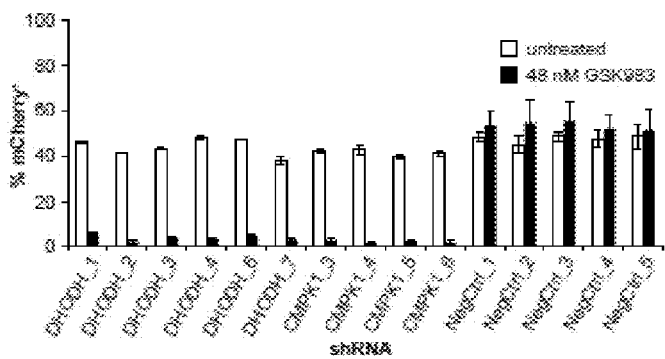
FIG. 6D
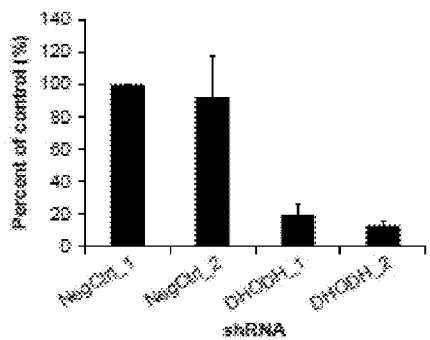
FIG. 6C
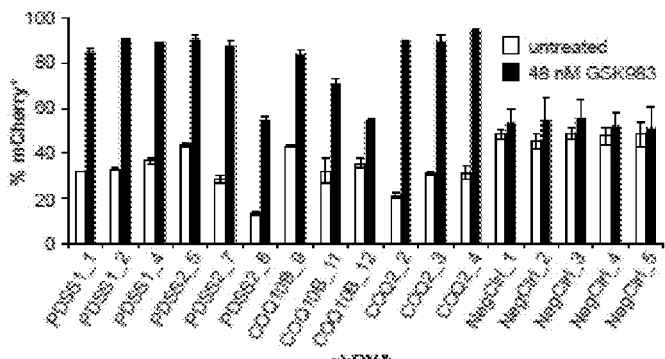
FIG. 6E

```
SEQUENCE LISTING

<160> NUMBER OF SEQ ID NOS: 22

<210> SEQ ID NO 1
<211> LENGTH: 40
<212> TYPE: DNA
<213> ORGANISM: Artificial Sequence
<220> FEATURE:
<223> OTHER INFORMATION: Synthetic nucleotide

<400> SEQUENCE: 1
aggcttggat tctataact tcgtatagca tacattatac                40

<210> SEQ ID NO 2
<211> LENGTH: 26
<212> TYPE: DNA
<213> ORGANISM: Artificial sequence
<220> FEATURE:
<223> OTHER INFORMATION: Synthetic nucleotide

<400> SEQUENCE: 2
acatgcatgg cggtaatacg gttatc                              26

<210> SEQ ID NO 3
<211> LENGTH: 45
<212> TYPE: DNA
<213> ORGANISM: Artificial sequence
<220> FEATURE:
<223> OTHER INFORMATION: Synthetic nucleotide

<400> SEQUENCE: 3
caagcagaag acggcatacg agatgcacaa aaggaaactc accct         45

<210> SEQ ID NO 4
<211> LENGTH: 82
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (62)..(63)
<223> OTHER INFORMATION: An Illumina Index Barcode is present between
      the nucleotides at positions 62 and 63.

<400> SEQUENCE: 4
aatgatacgg cgaccaccga gatctacacg atcggaagag cacacgtctg aactccagtc   60
accgactcgg tgccactttt tc                                           82
```

<210> SEQ ID NO 5
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 5
atgtatcaca gcctgtacct g                                              21

<210> SEQ ID NO 6
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 6
ttcttggtct cttcctcctt g                                              21

<210> SEQ ID NO 7
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 7
aaggtttcga gagcattcct                                                20

<210> SEQ ID NO 8
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 8
tgaaaggaag caaagcacct                                                20

<210> SEQ ID NO 9
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 9
agtcacagat gccattggag                                                20

<210> SEQ ID NO 10
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 10
gtccctcctc tcatgatcca                                                20

<210> SEQ ID NO 11
<211> LENGTH: 31
<212> TYPE: DNA
<213> ORGANISM: Artificial sequence
<220> FEATURE:
<223> OTHER INFORMATION: Synthetic nucleotide

<400> SEQUENCE: 11
acgacaagca tatggccacg ggagatgagc g                                    31

<210> SEQ ID NO 12
<211> LENGTH: 39
<212> TYPE: DNA
<213> ORGANISM: Artificial sequence
<220> FEATURE:
<223> OTHER INFORMATION: Synthetic nucleotide

<400> SEQUENCE: 12
gcgacccgaa ttcggccgcc gatgatctgc tccaatggc                            39

<210> SEQ ID NO 13
<211> LENGTH: 30
<212> TYPE: DNA
<213> ORGANISM: Artificial sequence
<220> FEATURE:
<223> OTHER INFORMATION: Synthetic nucleotide

<400> SEQUENCE: 13
aaaaaacata tgaagccgct ggtcgtgttc                                      30

<210> SEQ ID NO 14
<211> LENGTH: 39
<212> TYPE: DNA
<213> ORGANISM: Artificial sequence
<220> FEATURE:
<223> OTHER INFORMATION: Synthetic nucleotide

<400> SEQUENCE: 14
cacgtctaaa aactgttcct tccgattcct aggtttttt                            39

<210> SEQ ID NO 15
<211> LENGTH: 32
<212> TYPE: DNA
<213> ORGANISM: Artificial sequence
<220> FEATURE:
<223> OTHER INFORMATION: Synthetic nucleotide

<400> SEQUENCE: 15
ggaagttcta tcggccacat gtttgagaca ac                                   32

<210> SEQ ID NO 16
<211> LENGTH: 32
<212> TYPE: DNA
<213> ORGANISM: Artificial sequence
<220> FEATURE:
<223> OTHER INFORMATION: Synthetic nucleotide

<400> SEQUENCE: 16
gttgtctcaa acatgtggcc gatagaactt cc                                   32

<210> SEQ ID NO 17
<211> LENGTH: 19
<212> TYPE: DNA
<213> ORGANISM: Artificial sequence
<220> FEATURE:
<223> OTHER INFORMATION: Synthetic nucleotide

<400> SEQUENCE: 17
cgaaattcga gctcacgcg                                                  19

<210> SEQ ID NO 18

```
<211> LENGTH: 28
<212> TYPE: DNA
<213> ORGANISM: Artificial sequence
<220> FEATURE:
<223> OTHER INFORMATION: Synthetic nucleotide

<400> SEQUENCE: 18
tcctgctagc ttgagcaaat caaagttc                                         28

<210> SEQ ID NO 19
<211> LENGTH: 62
<212> TYPE: DNA
<213> ORGANISM: Artificial sequence
<220> FEATURE:
<223> OTHER INFORMATION: Synthetic nucleotide

<400> SEQUENCE: 19
tcaagctagc aggagacgtt gagtccaacc ccgggcccat gaataaccaa cggaaaagg      60 cg                                                                     62

<210> SEQ ID NO 20
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 20
ggaagagcat gcagtcggaa atg                                              23

<210> SEQ ID NO 21
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 21
atgaccacct gcttctggcg at                                               22

<210> SEQ ID NO 22
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 22
tttgagaatg agttcattgt ca                                               22
```

USE OF A DHODH INHIBITOR IN COMBINATION WITH AN INHIBITOR OF PYRIMIDINE SALVAGE

CROSS REFERENCE

This application claims benefit of PCT Application No. PCT/US2016/068365, filed Dec. 22, 2016, which claims benefit of U.S. Provisional Patent Application No. 62/272,428, filed Dec. 29, 2015, which applications are incorporated herein by reference in their entirety.

FEDERALLY SPONSORED RESEARCH AND DEVELOPMENT

This invention was made with Government support under contract AI109662 and HD084069 awarded by the National Institutes of Health. The Government has certain rights in the invention.

BACKGROUND

The rapid rise in the number of emerging pathogens in the world's population represents a serious global health problem and underscores the need to develop broad spectrum anti-infectives that target common components of large classes of pathogens. Targeting of viral proteins has the inextricable challenge of rise of resistance. Safe and effective vaccines are not possible for many viral pathogens. New approaches are required to address the unmet medical need in this area.

An understanding of the molecular mechanisms of viral life cycles has led to the identification of viral proteins as targets for therapeutic intervention, however few effective and safe agents have emerged, and these face the challenge of high mutation rates that have confounded many conventional antiviral products.

As an alternative to targeting viral proteins, targeting a cellular protein may lead to antiviral compounds with a broader spectrum of activity and less opportunity for developing resistance. However, targeting the host may result in toxicity, especially if the protein or pathway used is crucial for cell survival. The present invention provides broad spectrum anti-infective agents for use in treating viral infections.

SUMMARY OF THE DISCLOSURE

Compounds and methods are provided for the broad spectrum treatment of viral infections by administering a formulation that inhibits multiple pathways in pyrimidine synthesis and salvage. The compositions and methods of the invention combine an effective dose of a de novo pyrimidine biosynthesis inhibitor, such as an inhibitor of dihydroorotate dehydrogenase (DHODH), with an effective dose of an inhibitor of a protein in the pyrimidine salvage pathway. In some embodiments the active agent inhibitors are provided in a combined dosage formulation with a pharmaceutically acceptable excipient. In some embodiments the combined dosage formulation is for oral administration. In some embodiments each of the active agents is a small molecule therapeutic.

In other embodiments, methods are provided for treatment of cancer, including cancer cells expressing UCK2. The methods include administering a formulation that inhibits multiple pathways in pyrimidine synthesis and salvage, e.g. an effective dose of a de novo pyrimidine biosynthesis inhibitor, such as an inhibitor of dihydroorotate dehydrogenase (DHODH), with an effective dose of an inhibitor of a protein in the pyrimidine salvage pathway, e.g. UCK2. In some embodiments a method of treatment is provided. In some embodiments the cancer is tested for over-expression of UCK2 prior to, or in combination with drug treatment, where a patient is selected for treatment after determining that the cancer cells over-express UCK2 relative to a control cell, e.g. a paired normal cell from the same tissue.

In some embodiments the combination of active agents provides for decreased toxicity to the host. In some embodiments the dosage and ratio of agents is selected to achieve increased efficacy with reduced toxicity, particularly reduced toxicity relative to the administration of the DHODH inhibitor as a single agent. Indicia of toxicity may include, without limitation, leukopenia, and other effects on rapidly dividing cells.

The invention provides compositions and methods for the administration of formulations of these active agents, as well as unit dose forms of the formulations suitable for administration to patients. In some embodiments the ratio of active agents, i.e. inhibitor of DHODH to inhibitor of a pyrimidine salvage pathway enzyme may range from about 500:1, 100:1, 50:1, 25:1, 10:1, 5:1, 2:1, 1:1, 1:2, 1:5, 1:10, 1:25, 1:50, 1:100, 1:500 by weight, or by molarity.

In certain embodiments, the protein of the pyrimidine salvage pathway is uridine cytidine kinase 2 (UCK2). In some such embodiments, the inhibitor is an analog of a nucleotide or nucleoside that selectively inhibits UCK2, including without limitation 5'-chloro-5'-deoxyuridine, 5'-azido-5'-deoxyuridine, and saturated or unsaturated carbocyclic derivatives of uridine and cytidine.

In certain embodiments, the proteins of the pyrimidine salvage pathway are transporters responsible for uridine uptake in cells. In some such embodiments, the inhibitor is dipyridamole or nitrobenzylthioinosine.

In certain embodiments the inhibitor of DHODH is GSK983 or an analog thereof, as defined herein, which analogs include without limitation GSK983; GSK984, 6Br-pF and 6Br-oTol, each defined herein.

Also provided are methods of inhibiting viral infection in a subject by administering an effective dose of a combination therapy of the invention to a subject infected with a virus or at risk of virus infection, e.g. a person known to be exposed to a pathogenic virus. In some embodiments the virus infects a mammal or avian. In some embodiments the virus infects humans. In some embodiments the virus is an RNA virus, e.g. a Group III, Group IV, or Group V of the Baltimore classification system of classifying viruses, which groups comprise single stranded RNA viruses, double stranded RNA viruses, and retroviruses.

The subject combination of active agents may be formulated or provided to a subject in need thereof in combination with one or more additional agents, e.g. deoxycytidine supplementation, interferon, ribavirin, and the like for treatment of viral infection; or in combination with chemotherapeutic agents, checkpoint inhibitors or other immune-oncology agents, radiation therapy, and the like for treatment of cancer.

These and other advantages, and features of the disclosure will become apparent to those persons skilled in the art upon reading the details of the compositions and methods of use, which are more fully described below.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1I. shRNA and CRISPR-Cas9 screens to identify the cellular target and mechanism of action of GSK983. (FIG. 1A) Structure of GSK983. (FIG. 1B) GSK983 dose response in K562 cells. Viable cells were counted by flow cytometry (FSC/SSC) following 72 h GSK983 treatment at the indicated concentration. Error bars represent ± standard deviation of 8 biological replicates from two independent experiments. Schematic representation of genome-wide shRNA (FIG. 1C) and CRISPR-Cas9 (FIG. 1D) screens. (FIG. 1E) Top ten hits from the shRNA and CRISPR-Cas9 screens in cellular and biological context. Circle size is proportional to MLE score absolute value. Square size is proportional to median fold-enrichment or disenrichment. (FIG. 1F) Comparative analysis of results from shRNA and CRISPR-Cas9 screens. Pyrimidine metabolism (orange), CoQ10 biosynthesis (blue), regulation of mTORC1 activity (green). (FIG. 1G) Validation of selected top hit genes from the shRNA screen using a competitive growth assay. A total of 27 shRNAs were retested (6 targeting DHODH; 4 targeting CMPK1; 3 each targeting COQ2, PDSS2, PDSS1, and COQ10B; and 5 negative controls). Error bars represent ± standard deviation of log(mCherry enrichment ratio) values for all retested shRNAs targeting each gene. P values were calculated by Mann-Whitney U test. Validation of selected sensitizing (FIG. 1H) or protective (FIG. 1I) sgRNAs from the CRISPR-Cas9 screen using a competitive growth assay. Error bars represent the range of 2 biological replicates.

FIG. 2A-2E. GSK983 inhibits DHODH to block virus replication and cell proliferation. (FIG. 2A) Schematic representation of mammalian pyrimidine metabolism. Genes that appeared as strong sensitizing hits in the shRNA screen (CMPK1, DHODH, UCK2) and CRISPR-Cas9 screen (UCK2) are highlighted in yellow. (FIG. 2B) Dihydroorotic acid had no effect on GSK983-induced growth inhibition in K562 cells. (FIG. 2C) Orotic acid reversed GSK983-induced growth inhibition in K562 cells. For (FIG. 2B) and (FIG. 2C), viable cells were counted by flow cytometry (FSC/SSC) following 72 h treatment with 48 nM GSK983 or vehicle and the indicated concentration of (dihydro)orotic acid. Error bars represent ± standard deviation of 4 biological replicates. (FIG. 2D) GSK983 and analogues inhibited recombinant human DHODH in vitro. $K_i$ values are averages of two independent $K_i$ determinations at different inhibitor concentrations. The range between independently calculated $K_i$ values for each inhibitor is shown in parentheses. $IC_{50}$ values for inhibition of episomal HPV-16 replication in cell-based antiviral assays are those reported by GlaxoSmithKline. (FIG. 2E) Structures of GSK983, 6Br-pF, 6Br-oTol, and GSK984.

(FIG. 3C) GSK983 inhibited replication of luciferase-expressing DENV in A549 cells (black). 1 mM uridine reversed antiviral activity (blue), while 1 mM deoxycytidine did not (red). Error bars represent ± standard deviation of 3 biological replicates. (FIG. 3D) Uridine (blue) and deoxycytidine (red) reversed GSK983-induced growth inhibition in A549 cells. Viable cells were counted by flow cytometry (FSC/SSC) following 72 h treatment with no exogenous pyrimidines (control), 1 mM uridine, or 1 mM deoxycytidine and the indicated concentration of GSK983. Error bars represent ± standard deviation of 3 biological replicates. (FIG. 3E) Ribonucleoside (uridine) salvage sustains both RNA virus replication and cellular DNA synthesis. (FIG. 3F) Deoxyribonucleoside (deoxycytidine) salvage sustains cellular DNA synthesis but not RNA virus replication. For (FIG. 3E) and (FIG. 3F), Pyr=pyrimidine, rNuc=ribonucleotides, dNuc=deoxyribonucleotides. (FIG. 3G) Deoxycytidine reversed GSK983-induced S phase cell cycle arrest in K562 cells. Following 24 h treatment with 48 nM GSK983, cells were treated with 10 μM 5-ethynyl-2'-deoxyuridine (EdU) for 2 h and fixed in 70% EtOH. Cells were stained with Azide-fluor 488 and 7-AAD and analyzed by flow cytometry. Flow cytometry plots depict one of three biological replicates.

FIG. 4A-4F. (FIG. 4A) Synthesis of GSK983. (FIG. 4B) Time-dependence of GSK983-induced growth inhibition in K562 cells. Viable cells were counted by flow cytometry (FSC/SSC) at the indicated time points following treatment with 0-100 nM GSK983. Error bars represent ± standard deviation of 4 biological replicates. (FIG. 4C) GSK983-induced S phase cell cycle arrest in K562 cells. Cells were treated with the indicated concentration of GSK983 for 24 h, fixed in 70% EtOH, stained with propidium iodide, and analyzed by flow cytometry. (FIG. 4D) Cell cycle analysis of GSK983-treated K562 cells. Flow cytometry plots depict one of three biological replicates from data summarized in FIG. 4c. (FIG. 4E) GSK983-induced apoptosis in K562 cells. Cells were treated with the indicated concentration of GSK983 for 72, fixed in 70% EtOH, stained with annexin V-FITC and 7-AAD, and analyzed by flow cytometry. Error bars represent ± standard deviation of 4 biological replicates. (FIG. 4F) GSK983-induced apoptosis in K562 cells. Flow cytometry plots depict one of four biological replicates from data summarized in FIG. 4e.

(FIG. 5A) Mammalian coenzyme Q10 (CoQ10) biosynthesis. Genes shown in bold appeared among the top ten hits in the shRNA screen (PDSS2, COQ2, PDSS1) and/or CRISPR-Cas9 screen (PDSS2, COQ9, HMGCR, PDSS1). (FIG. 5B) Comparison of counts of shRNA-encoding constructs in genomic DNA isolated from untreated and GSK983-treated cells following our genome-wide shRNA screen. For each plot, the enlarged, colored circles represent shRNAs targeting the indicated gene. The grey cloud represents the set of negative control shRNAs.

FIG. 6A-6E. (FIG. 6A) Schematic representation of competitive growth assays used to retest individual shRNAs. (FIG. 6B) shRNA-mediated knockdown of DHODH or CMPK1 sensitized K562 cells to GSK983 in competitive growth assays. Six shRNAs targeting DHODH, four shRNAs targeting CMPK1, and five negative control shRNAs were retested. Error bars represent the range of 2 biological replicates. (FIG. 6C) shRNA-mediated knockdown of PDSS1, PDSS2, COQ10B, and COQ2 protected K562 cells against GSK983 in competitive growth assays. Three shRNAs targeting each gene and five negative control shRNAs were retested. Error bars represent the range of 2 biological replicates. qPCR to confirm the efficacy of selected shRNAs targeting DHODH (FIG. 6D), and CMPK1 (FIG. 6E). Measurements are the average of 3 replicates, error bars represent ± standard deviation of 3 biological replicates. All values are normalized to the first of two negative control shRNAs.

(FIG. 7A) Schematic representation of competitive growth assays used to validate sgRNAs targeting top hit genes from the CRISPR-Cas9 screen. (FIG. 7B) Retesting in HeLa cells of selected sgRNAs targeting top hit genes from the CRISPR-Cas9 screen. Error bars represent the range of 2 biological replicates.

FIG. 8A-8G. (FIG. 8A) Dihydroorotic acid had no effect on GSK983-induced growth inhibition in HeLa cells. (FIG. 8B) Orotic acid reversed GSK983-induced growth inhibition in HeLa cells. For (FIG. 8A) and (FIG. 8B), viable cells were counted by flow cytometry (FSC/SSC) following 72 h treatment with 48 nM GSK983 or vehicle and the indicated concentration of (dihydro)orotic acid. Error bars represent ± standard deviation of 4 biological replicates. Effect of (FIG. 8C) teriflunomide, (FIG. 8D) GSK983, (FIG. 8E) 6Br-pF, (FIG. 8F) 6Br-oTol, and (FIG. 8G) GSK984 on the activity of recombinant human DHODH in vitro. For each inhibitor, the Ki was determined with respect to the concentration of decylubiquinone (Qd) at two different inhibitor concentrations.

(FIG. 9A) Cytidine partially reversed GSK983-induced growth inhibition in K562 cells. Viable cells were counted by flow cytometry (FSC/SSC) following 72 h treatment with 48 nM GSK983 or vehicle and the indicated concentration of cytidine. Error bars represent ± standard deviation of 4 biological replicates. (FIG. 9B) Low concentrations of exogenous uridine (≤20 µM) are unable to completely reverse the anti-proliferative effect of GSK983 in K562 cells. Viable cells were counted by flow cytometry (FSC/SSC) following 72 h treatment with 48 nM GSK983 or vehicle and the indicated concentration of uridine. Error bars represent ± standard deviation of 4 biological replicates. 1 mM exogenous deoxycytidine largely reversed the antiproliferative effect of 30 nM GSK983 in K562 cells after 3 days (FIG. 9C), but this effect was less pronounced after 6 days (FIG. 9D). Viable cells were counted by flow cytometry (FSC/SSC) following 3 day (FIG. 9C) or 6 day (FIG. 9D) treatment with the indicated concentration of GSK983 and deoxycytidine. Error bars represent ± standard deviation of 4 biological replicates. (FIG. 9E) Effect of GSK983 on VEEV-GFP replication in A549 cells in the absence of exogenous pyrimidines (control, black circles), or in the presence of 1 mM uridine (blue squares), 1 mM deoxycytidine (red triangles), 1 mM dihydroorotic acid (purple diamonds), or 1 mM orotic acid (green stars). A549 cells were incubated with the indicated combination of GSK983 and pyrimidine metabolite for 24 h prior to VEEV infection. Cells were then incubated with VEEV (MOI=20 plaque-forming units/cell) for an additional 16 h. Viral replication was measured by GFP fluorescence using flow cytometry. Error bars represent ± standard deviation of 3 biological replicates.

(FIG. 10A) Summary of results from EdU-based cell cycle analysis shown in FIG. 3g. Error bars represent ± standard deviation of 3 biological replicates. (FIG. 10B) Deoxycytidine (dC) reversed GSK983-induced S phase cell cycle arrest in K562, HeLa, and A549 cells. For all three cell lines, cells were treated with 48 nM GSK983 for 24 h, fixed in 70% EtOH, stained with propidium iodide, and analyzed by flow cytometry. For each cell line, flow cytometry plots are representative of three biological replicates. Deoxycytidine reduced GSK983 toxicity in (FIG. 10C) K562 cells, (FIG. 10D) HeLa cells, and (FIG. 10E) A549 cells at all growth-inhibitory doses. For (c), (d), and (e), viable cells were counted by flow cytometry (FSC/SSC) following 72 h treatment with GSK983 at the indicated concentration. Error bars represent ± standard deviation of 4 biological replicates. (FIG. 10F) Deoxycytidine alleviated teriflunomide toxicity in K562 cells at all growth-inhibitory doses. Viable cells were counted by flow cytometry (FSC/SSC) following 72 h treatment with teriflunomide at the indicated concentration. Error bars represent ±standard deviation of 4 biological replicates.

(FIG. 11A) Uridine salvage inhibition in K562 and A549 cells was quantified using 5-ethynyl-uridine (5-EU) and click chemistry. (FIG. 11B) Using this assay, DP had an $IC_{50}$ of 0.2 µM. (FIG. 11C) Two different UCK2 shRNA derivatives of K562 were constructed. Both showed reduced uptake of uridine.

(FIG. 12A) Effect of shRNA knockdown of UCK2 onto the propagation of a luciferase-expressing DENV strain in cell cultures containing 48 nM GSK983 in 20 µM uridine. (FIG. 12B) Combined effect of 48 nM GSK983 and varying doses of dipyridamole (DP) in A549 cells infected with the same virus in 20 µM uridine supplemented media. The $EC_{50}$ of DP is estimated as 135 nM after 2 days and 164 nM after 3 days post-infection. Luciferase signal is a convenient surrogate for DENV propagation in this assay.

DEFINITIONS

Figure 3A:
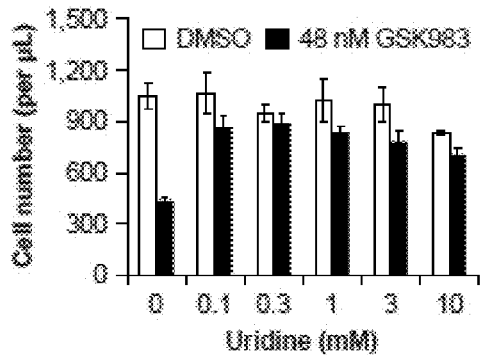
FIG. 3A-3G. Deoxycytidine (dC) reverses the anti-proliferative effect of GSK983 but not antiviral activity. Uridine (FIG. 3A) and deoxycytidine (FIG. 3B) largely reversed GSK983-induced growth inhibition in K562 cells. For (FIG. 3A) and (FIG. 3B), viable cells were counted by flow cytometry (FSC/SSC) following 72 h treatment with 48 nM GSK983 or vehicle and the indicated concentration of uridine or deoxycytidine. Error bars represent ±standard deviation of 4 biological replicates.
Figure 3B:
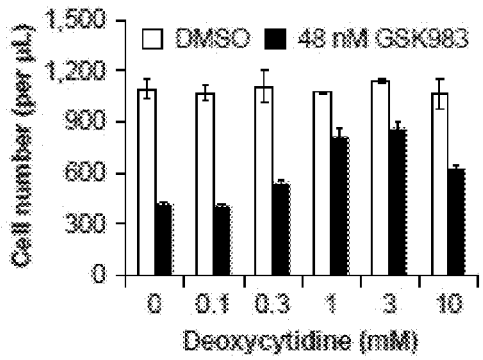

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect, such as reduction of viral titer. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease (e.g., reduction in viral titers).

The terms "individual," "host," "subject," and "patient" are used interchangeably herein, and refer to an animal, including, but not limited to, human and non-human primates, including simians and humans; rodents, including rats and mice; bovines; equines; ovines; felines; canines; avians, and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

Pathogenic virus. The compositions and methods of the present invention provide for improved treatment of pathogenic viruses, particularly viruses that infect avians and mammals for medical and veterinary use. Viruses include those that infect, e.g. farm animals including horses, cattle, sheep, pigs, chickens, turkeys, etc., domestic animals including dogs and cats; and viruses that infect humans. Viruses include DNA viruses and RNA viruses.

In some embodiments a virus for treatment by the methods of the invention is an RNA virus. An RNA virus is a virus that has RNA (ribonucleic acid) as its genetic material. This nucleic acid is usually single-stranded RNA (ssRNA) but may be double-stranded RNA (dsRNA). Human diseases caused by RNA viruses include AIDS, Ebola hemorrhoragic fever, SARS, influenza, hepatitis C, West Nile fever, polio, and measles.

The ICTV classifies RNA viruses as those that belong to Group III, Group IV or Group V of the Baltimore classification system of classifying viruses and does not consider viruses with DNA intermediates in their life cycle as RNA viruses. Viruses with RNA as their genetic material but that include DNA intermediates in their replication cycle are retroviruses, and comprise Group VI of the Baltimore classification. Notable human retroviruses include HIV-1 and HIV-2, the cause of the disease AIDS. For the purposes of the present invention, an RNA virus is one that is within Group III, IV, V or VI unless otherwise indicated.

The double-stranded (ds)RNA viruses represent a diverse group of viruses that vary widely in host range, genome segment number, and virion organization. Members of this group include the rotaviruses and picobirnaviruses. The clades include the Caliciviridae, Flaviviridae, and Picornaviridae families, and a second that includes the Alphatetraviridae, Birnaviridae and Cystoviridae, Nodaviridae, and Permutotretraviridae families. Double-stranded RNA viruses (Group III) contain from one to a dozen different RNA molecules, each coding for one or more viral proteins.

RNA viruses can be further classified according to the sense or polarity of their RNA into negative-sense and positive-sense, or ambisense RNA viruses. Positive-sense ssRNA viruses (Group IV) have their genome directly utilized as if it were mRNA, with host ribosomes translating it into a single protein that is modified by host and viral proteins to form the various proteins needed for replication. One of these includes RNA-dependent RNA polymerase (RNA replicase), which copies the viral RNA to form a double-stranded replicative form. In turn this directs the formation of new virions. Viruses in this group include I. Bymoviruses, comoviruses, nepoviruses, nodaviruses, picornaviruses, potyviruses, sobemoviruses and a subset of luteoviruses (beet western yellows virus and potato leafroll virus)—the picorna like group (Picornavirata); II. Carmoviruses, dianthoviruses, flaviviruses, pestiviruses, tombusviruses, hepatitis C virus and a subset of luteoviruses (barley yellow dwarf virus)—the flavi like group (Flavivirata); Ill. Alphaviruses, carlaviruses, furoviruses, hordeiviruses, potexviruses, rubiviruses, tobraviruses, tricornaviruses, tymoviruses and hepatitis E virus—the alpha like group (Rubivirata). Alphaviruses and flaviviruses can be separated into two families—the Togaviridae and Flaviridae.

Negative-sense ssRNA viruses (Group V) must have their genome copied by an RNA replicase to form positive-sense RNA. The positive-sense RNA molecule then acts as viral mRNA, which is translated into proteins by the host ribosomes. The resultant protein goes on to direct the synthesis of new virions, such as capsid proteins and RNA replicase, which is used to produce new negative-sense RNA molecules. Group V-negative-sense ssRNA viruses include one order and eight families in this group. The group includes a number of clinically relevant pathogens. Bornaviridae-Borna disease virus; Family Filoviridae-includes Ebola virus, Marburg virus; Family Paramyxoviridae-includes Measles virus, Mumps virus, Nipah virus, Hendra virus, RSV and NDV; Family Rhabdoviridae-includes Rabies virus; Family Nyamiviridae-includes Nyavirus; Family Arenaviridae-includes Lassa virus; Family Bunyaviridae-includes Hantavirus, Crimean-Congo hemorrhagic fever; Family Ophioviridae; Family Orthomyxoviridae-includes Influenza viruses; Genus Deltavirus-includes Hepatitis D virus; Genus Dichorhavirus; Genus Emaravirus; Genus Nyavirus-includes Nyamanini and Midway viruses; Genus Tenuivirus; Genus Varicosavirus Retroviruses (Group VI) have a single-stranded RNA genome although they use DNA intermediates to replicate. Reverse transcriptase, a viral enzyme that comes from the virus itself after it is uncoated, converts the viral RNA into a complementary strand of DNA, which is copied to produce a double-stranded molecule of viral DNA. After this DNA is integrated into the host genome using the viral enzyme integrase, expression of the encoded genes may lead to the formation of new virions. Included in retroviruses are the lentiviruses, e.g. HIV-1 and HIV-2.

The term "tumor," as used herein, refers to all neoplastic cell growth and proliferation, whether malignant or benign, and all pre-cancerous and cancerous cells and tissues.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. In general, the cells of interest for detection, analysis, classification, or treatment in the present application include precancerous (e.g., benign), malignant, pre-metastatic, and non-metastatic cells.

The term "primary tumor" refers to all neoplastic cell growth and proliferation, whether malignant or benign, and all pre-cancerous and cancerous cells and tissues located at the anatomical site where the autonomous, unregulated growth of the cells initiated, for example the organ of the original cancerous tumor. Primary tumors do not include metastases.

The "pathology" of cancer includes all phenomena that compromise the well-being of the patient. This includes, without limitation, abnormal or uncontrollable cell growth, primary tumor growth and formation, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor (e.g., the organ containing the primary tumor). Metastasis can also be defined as several steps of a process, such as the departure of cancer cells from an original tumor site (e.g., primary tumor site) and migration and/or invasion of cancer cells to other parts of the body.

Depending on the nature of the cancer, an appropriate patient sample is obtained. As used herein, the phrase "cancerous tissue sample" refers to any cells obtained from a cancerous tumor. In the case of solid tumors which have not metastasized (for example a primary tumor), a tissue sample from the surgically removed tumor will typically be obtained and prepared for testing by conventional techniques.

The definition of an appropriate patient sample encompasses blood and other liquid samples of biological origin, solid tissue samples such as a biopsy specimen or tissue cultures or cells derived there from and the progeny thereof. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

Tumors of interest for treatment with the methods of the invention include solid tumors, e.g. carcinomas, gliomas, melanomas, sarcomas, and the like. Breast cancer is of particular interest. Carcinomas include the a variety of adenocarcinomas, for example in prostate, lung, etc.; adernocartical carcinoma; hepatocellular carcinoma; renal cell carcinoma; ovarian carcinoma, carcinoma in situ, ductal carcinoma, carcinoma of the breast, basal cell carcinoma; squamous cell carcinoma; transitional cell carcinoma; colon carcinoma; nasopharyngeal carcinoma; multilocular cystic renal cell carcinoma; oat cell carcinoma, large cell lung carcinoma; small cell lung carcinoma; etc. Carcinomas may be found in prostrate, pancreas, colon, brain (usually as secondary metastases), lung, breast, skin, etc. Including in the designation of soft tissue tumors are neoplasias derived from fibroblasts, myofibroblasts, histiocytes, vascular cells/endothelial cells and nerve sheath cells. Tumors of connective tissue include sarcomas; histiocytomas; fibromas; skeletal chondrosarcoma; extraskeletal myxoid chondrosarcoma; clear cell sarcoma; fibrosarcomas, etc. Hematologic cancers include leukemias and lymphomas, e.g. cutaneous T cell lymphoma, acute myeloid leukemia (AML), chronic myeloid leukemia (CML), acute lymphoblastic leukemia (ALL), non-Hodgkins lymphoma (NHL), etc.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

Anti-proliferative, or cytoreductive therapy is used therapeutically to eliminate tumor cells and other undesirable cells in a host, and includes the use of therapies such as delivery of ionizing radiation, and administration of chemotherapeutic agents, and may be used in combination with the agents of the invention. Chemotherapeutic agents are well-known in the art and are used at conventional doses and regimens, or at reduced dosages or regimens, including for example, topoisomerase inhibitors such as anthracyclines, including the compounds daunorubicin, adriamycin (doxorubicin), epirubicin, idarubicin, anamycin, MEN 10755, and the like. Other topoisomerase inhibitors include the podophyllotoxin analogues etoposide and teniposide, and the anthracenediones, mitoxantrone and amsacrine. Other anti-proliferative agent interferes with microtubule assembly, e.g. the family of vinca alkaloids. Examples of vinca alkaloids include vinblastine, vincristine; vinorelbine (NAVELBINE); vindesine; vindoline; vincamine; etc. DNA-damaging agent include nucleotide analogs, alkylating agents, etc. Alkylating agents include nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc. Nucleotide analogs include pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc. Other chemotherapeutic agents of interest include metal complexes, e.g. cisplatin (cis-DDP), carboplatin, oxaliplatin, etc.; ureas, e.g. hydroxyurea; gemcitabine, and hydrazines, e.g. N-methylhydrazine.

For example, ionizing radiation (IR) is used to treat about 60% of cancer patients, by depositing energy that injures or destroys cells in the area being treated, and for the purposes of the present invention may be delivered at conventional doses and regimens, or at reduced doses. Radiation injury to cells is nonspecific, with complex effects on DNA. The efficacy of therapy depends on cellular injury to cancer cells being greater than to normal cells. Radiotherapy may be used to treat every type of cancer. Some types of radiation therapy involve photons, such as X-rays or gamma rays. Another technique for delivering radiation to cancer cells is internal radiotherapy, which places radioactive implants directly in a tumor or body cavity so that the radiation dose is concentrated in a small area. A suitable dose of ionizing radiation may range from at least about 2 Gy to not more than about 10 Gy, usually about 5 Gy. A suitable dose of ultraviolet radiation may range from at least about 5 $J/m^2$ to not more than about 50 $J/m^2$, usually about 10 $J/m^2$. The sample may be collected from at least about 4 and not more than about 72 hours following ultraviolet radiation, usually around about 4 hours.

Dihydroorotate dehydrogenase (DHODH) catalyzes the fourth enzymatic step, the ubiquinone-mediated oxidation of dihydroorotate to orotate, in de novo pyrimidine biosynthesis. This protein is a mitochondrial protein located on the outer surface of the inner mitochondrial membrane. The enzyme classification is EC 1.3.3.1. Human DHODH has two domains: an alpha/beta-barrel domain containing the active site and an alpha-helical domain that forms the opening of a tunnel leading to the active site.

For use in the present invention, inhibitors of DHODH include known inhibitors as well as compounds that are identified herein as inhibitors. Known inhibitors of DHODH include the immunomodulatory drugs teriflunomide and leflunomide. Other inhibitors include, without limitation, those disclosed in, for example Baumgartner et al. (2006) J. Med. Chem. 49(4):1239-1247; Lolli et al. (2012) Eur. J. Med. Chem. 49:102-109; Lucas-Hourani et al. (2015) J. Med. Chem. 58(14):5579-5598.

Known compounds that were previously not known to be inhibitors of DHODH include compounds disclosed in International application WO 2006/118607, herein specifically incorporated by reference. Included in such compositions are GSK983, a tetrahydrocarbazole that inhibits the replication of a variety of unrelated viruses in vitro with $EC_{50}$ values of 5-20 nM (see Harvey et al. (2009) Antiviral Res. 82(1):1-11) and analogs thereof. Such compounds may have the structure:

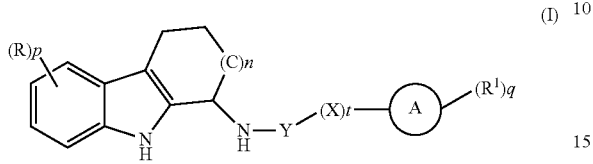

wherein: n is 0, 1,or 2; t is 0 or 1; X is —NH—, —O—, —$R^{10}$—, —$OR^{10}$, —$R^{10}O$—, —$R^{10}OR^{10}$—, —$NR^{10}$—, —$R^{10}N$—, —$R^{10}NR^{10}$—, —$R^{10}S(O)_m$—, or —$R^{10}S(O)_m$ $R^{10}$—; Y is —C(O)— or —$S(O)_m$—;

each R is the same or different and is independently selected from the group consisting of halogen, haloalkyl, akkyl, akenyl, alkynyl, cycloalkyl, cycloakenyl, —$R^{10}$cycloalkyl, Ay, —$NHR^{10}$Ay, Het, —NHHet, —$NHR^{10}$Het, —$OR^2$, —OAy, —OHet, —$R^{10}OR^2$, —$NR^2R^3$, —$NR^2$Ay, —$R^{10}NR^2R^3$, —$R^{10}NR^2$Ay, —$R^{10}C(O)R^2$, —$C(O)R^2$, —$CO_2R^2$, —$R^{10}CO_2R^2$, —$C(O)NR^2R^3$, —C(O)Ay, —$C(O)NR^2$Ay, —C(O)Het, —$C(O)NHR^{10}$Het, —$R^{10}C(O)NR^2R^3$, —$C(S)NR^2R^3$, —$R^{10}C(S)NR^2R^3$, —$R^{10}NHC(NH)NR^2R^3$, —$C(NH)NR^2R^3$, —$R^{10}C(NH)NR^2R^3$, —$S(O)_2NR^2R^3$, —$S(O)_2NR^2$Ay, —$R^{10}SO_2NHCOR^2$, —$R^{10}SO_2NR^2R^3$, —$R^{10}SO_2R^2$, —$S(O)_mR^2$, —$S(O)_m$Ay, cyano, nitro, or azido;

each $R^1$ is the same or different and is independently selected from the group consisting of halogen, haloalkyl, alkyl, alkenyl, alkynyl, cycloakyl, cycloakenyl, —$R^{10}$cycloakyl, Ay, —$NHR^{10}$Ay, Het, —NHHet, —$NHR^{10}$Het, —$OR^2$, —OAy, —OHet, —$R^{10}OR^2$, —$NR^2R^3$, —$NR^2$Ay, —$R^{10}NR^2R^3$, —$R^{10}NR^2$Ay, —$R^{10}C(O)R^2$, —$C(O)R^2$, —$CO_2R^2$, —$C(O)NR^2R^3$, —C(O)Ay, —$C(O)NR^2$Ay, —C(O)Het, —$C(O)NHR^{10}$Het, —$R^{10}C(O)NR^2R^3$, —$C(S)NR^2R^3$, —$R^{10}C(S)NR^2R^3$, —$R^{10}NHC(NH)NR^3R^3$, —$C(NH)NR^2R^3$, —$R^{10}C(NH)NR^2R^3$. —$S(O)_2NR^2R^3$, —$S(O)_2NR^2$Ay, —$R^{10}SO_2NHCOR^2$, —$R^{10}NR^2T^3$, —$R^{10}SO_2R^2$, —$S(O)_mR^2$. —$S(O)_m$Ay, cyano, nitro, or azido;

each m independently is 0, 1, or 2;

each $R^{10}$ is the same or different and b Independently selected from alkylene, cycloalkylene, alkenylene, cycloalkenylene, and alkynylene;

p and q are each independently selected from 0, 1, 2, 3, 4, or 5;

each of $R^2$ and $R^3$ are the same or different and are independently selected from the group consisting of H, alkyl, alkenyl, alkenyl, cycloakyl, cycloalkenyl, —$R^{10}$cycloakyl, —$R^{10}$OH, —$R^{10}(OR^{10})_w$, and —$R^{10}NR^4R^5$;

w is 1-10;

each of $R^4$ and $R^6$ are the same or different and are independently selected Horn the group consisting of alkyl, cycloakyl, alkenyl, cycloakenyl, and alkynyl;

Ay represents an aryl group; Het represents a 5- or 6-membered heterocyclyl or heteroaryl group; ring A is aryl or heteroaryl; provided that when the A ring is aryl, t is 0, and Y is $SO_2$, then p is not 0;

including salts, solvates and physiologically functional derivatives thereof.

In some embodiments the inhibitor of DHODH is GSK983 or an analog thereof, including without limitation 6Br-pF, 6Br-oTol, and GSK984, which compounds have the following structures:

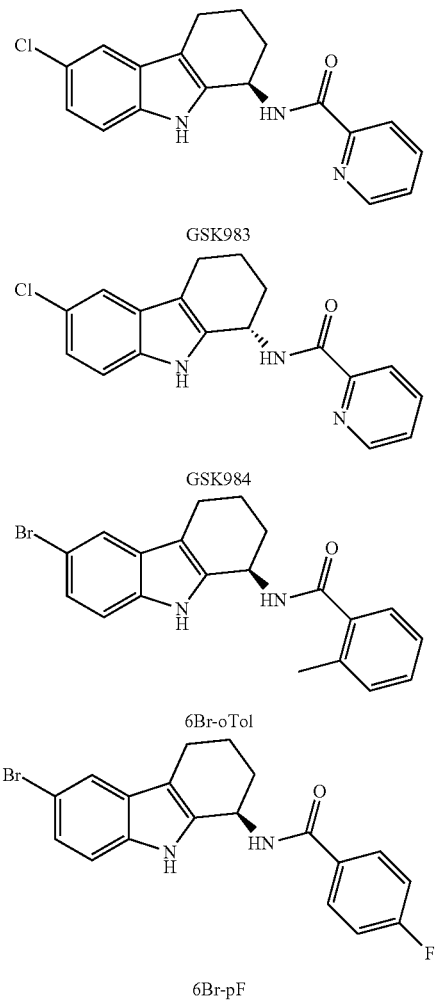

Pyrimidine salvage pathway. In pyrimidine salvage reactions, nucleosides and free bases generated by DNA and RNA breakdown are converted back to nucleotide monophosphates, allowing them to re-enter the pathways of pyrimidine biosynthesis. A schematic is shown in FIG. 2A. An inhibitor, which may be a selective inhibitor, of a protein in the pyrimidine salvage pathway may be referred to as a pyrimidine salvage pathway inhibitor generically, or as an inhibitor of the specific enzyme, e.g. a UCK2 inhibitor. In some embodiments an inhibitor of interest is a small molecule, including without limitation nucleoside, nucleotide, and pyrimidine analogs.

Enzymes of interest in the pathway include cytidine deaminase (CDA), which catalyzes the irreversible hydrolytic deamination of cytidine and deoxycytidine to uridine and deoxyuridine, respectively. Inhibitors of CDA include, without limitation, zebularine, Tetrahydrouridine (THU).

The enzyme uridine-cytidine kinase 2 (UCK2) phosphorylates uridine and cytidine to uridine monophosphate and cytidine monophosphate. It does not phosphorylate deoxy-ribonucleosides or purine ribonucleosides, and can use ATP or GTP as a phosphate donor. Inhibitors of UCK2 include, without limitation, 5[-Azido-5]-deoxycytidine; 5[-Azido-5]-deoxyuridine, 5[-Iodo-5]-deoxyuridine, 5[-Azido-5]-deoxy-6-azauridine, 5-O-Nitrouridine, 5-O-Nitro-5-fluorouridine, 5-azacytidine 5'-triphosphate, and 5-Nitrouridine. Cyclopentenyluridine and cyclopentenylcytidine analogs are inhibitors of uridine-cytidine kinase, see Lim et al. (1984) J. Med. Chem. 27(12):1536-1538; Moyer et al. (1985) Mol. Pharmacol. 28:454-460; and Ahmed et al. (1982) Int. J. Biochem, 14(4):259-262, herein specifically incorporated by reference.

Cytidine monophosphate kinase 1 (CMPK1) catalyzes the transfer of a phosphate group from ATP to CMP, UMP, or dCMP, to form the corresponding diphosphate nucleotide. Inhibitors of this enzyme include, without limitation, 2'-deoxy-2',2'-difluorocytidine.

Determination of additional inhibitors can be determined by conventional screening methods, e.g. contacting a pyrimidine salvage pathway enzyme with a candidate inhibitor, and determining the effect on the enzymatic activity, e.g. phosphorylation of uridine or cytidine.

Additional inhibitors of interest include inhibitors of nucleoside transporters. At least three distinct nucleoside transporters are known to exist in mammalian cells with tolerance toward exogenous uridine. Clinically useful inhibitors include without limitation dipyridamole, dilazep, and S-4-nitrophenylmethyl-6-thioinosine, and have broad target specificity.

An effective and specific inhibitor of pyrmidine salvage, e.g. an inhibitor of UCK2, can act synergistically with a DHODH inhibitor to achieve improved activity against viruses, particularly against RNA viruses.

"In combination with", "combination therapy" and "combination products" refer, in certain embodiments, to the concurrent administration to a patient of a first therapeutic and a second therapeutic, as used herein. When administered in combination, each component can be administered at the same time or sequentially in any order at different points in time. Thus, each component can be administered separately but sufficiently closely in time so as to provide the desired therapeutic effect. Alternatively a co-formulation can include an effective dose of each of the active agents in a single formulation.

"Concomitant administration" of two active agents as set forth in the present invention means administration with the two agents such that they will have a therapeutic effect. Such concomitant administration may involve concurrent (i.e. at the same time), prior, or subsequent administration of one agents with respect to the administration of the other agent. A person of ordinary skill in the art would have no difficulty determining the appropriate timing, sequence and dosages of administration for particular drugs and compositions of the present invention.

As used herein, endpoints for treatment will be given a meaning as known in the art and as used by the Food and Drug Administration.

Overall survival is defined as the time from randomization until death from any cause, and is measured in the intent-to-treat population. Survival is considered the most reliable endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased survival of patients with reduced toxicity relative to administration of the DHODH inhibitor as a single agent.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, may contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—CH2-), ethylene (—CH2CH2-), propylene (—CH2CH2CH2-), 2-methylpropylene (—CH2-CH(CH3)-CH2-), hexylene (—(CH2)6-) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

As used herein, the terms "Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH2), mono-substituted C1-C24 alkylcarbamoyl (—(CO)—NH(C1-C24 alkyl)), di-substituted alkylcarbamoyl (—(CO)—N(C1-C24 alkyl)2), mono-substituted arylcarbamoyl (—(CO)—NH-aryl), thiocarbamoyl (—(CS)—NH2), carbamido (—NH—(CO)—NH2), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—NH2), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO2), nitroso (—NO), sulfo (—SO2-OH), sulfonato (—SO2-O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—SO2-aryl), phosphono (—P(O)(OH)2), phosphonato (—P(O)(O—)2), phosphinato (—P(O)(O—)), phospho (—PO2), and phosphino (—PH2), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a bivalent radical moiety that connects two groups via covalent bonds. Examples of such linking groups include alkylene, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—), carbonyldioxy (—O—CO—O—), alkyldioxy (—O—(CH2)n-O—), epoxyimino (—O—NH—), epimino (—NH—), carbonyl (—CO—), etc. Any convenient orientation and/or connections of the linkers to the linked groups may be used.

When the term "substituted" appears prior to a list of possible substituted groups, it is intended that the term apply to every member of that group. For example, the phrase "substituted alkyl and aryl" is to be interpreted as "substituted alkyl and substituted aryl."

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include 1H, 2H (i.e., D) and 3H (i.e., T), and reference to C is meant to include 12C and all isotopes of carbon (such as 13C).

Definitions of other terms and concepts appear throughout the detailed description below.

DETAILED DESCRIPTION OF THE EMBODIMENTS

As summarized above, compounds and methods are provided for the treatment of pathogenic viral infections, particularly pathogenic RNA virus infections. The anti-infective combinations of the invention have broad spectrum activity against a variety of virus infections.

Also provided are pharmaceutical compositions that include the subject combination formulations, where the combined active agents of the invention are formulated with a pharmaceutically acceptable excipient. Formulations may be provided in a unit dose, where the dose provides an amount of the compound effective to achieve a desired result, including without limitation inhibition of pathogenic virus replication.

Optimization for Bioavailability and Metabolic Stability

In some embodiments, the subject compounds are provided by oral dosing and absorbed into the bloodstream. In some embodiments, the oral bioavailability of the subject compounds is 30% or more. Modifications may be made to the subject compounds or their formulations using any convenient methods to increase absorption across the gut lumen or their bioavailability.

In some embodiments, the subject compounds are metabolized in vivo to produce one or more metabolites. In some embodiments, the subject compounds may be optimized for metabolic stability using any convenient methods. In some embodiments, the subject compounds are metabolically stable (e.g., remain substantially intact in vivo during the half-life of the compound). In certain embodiments, the compounds have a half-life (e.g., an in vivo half-life) of 5 minutes or more, such as 10 minutes or more, 12 minutes or more, 15 minutes or more, 20 minutes or more, 30 minutes or more, 60 minutes or more, 2 hours or more, 6 hours or more, 12 hours or more, 24 hours or more, or even more.

In some embodiments, the subject compositions comprise an inhibitor of DHODH, including without limitation GSK983 or an analog thereof, and an inhibitor of a pyrimidine salvage pathway enzyme. In certain embodiments the subject compositions comprise an inhibitor of DHODH, including without limitation GSK983 or an analog thereof, and an inhibitor of a mammalian UCK2 enzyme. The activity of the active agents may be determined by an inhibition assay, e.g., by an assay that determines the level of activity of the enzyme either in a cell-free system or in a cell after treatment with a subject compound, relative to a control, by measuring the $IC_{50}$ or $EC_{50}$ value, respectively. In certain embodiments, the subject compounds have an $IC_{50}$ value (or $EC_{50}$ value) of 10 µM or less, such as 3 µM or less, 1 µM or less, 500 nM or less, 300 nM or less, 200 nM or less, 100 nM or less, 50 nM or less, 30 nM or less, 10 nM or less, 5 nM or less, 3 nM or less, 1 nM or less, or even lower.

In some embodiments, a UCK2 inhibitor for use in the combinations of the invention have an activity as determined by a kinase activity assay, e.g., by an assay that determines the level of incorporation of radiolabeled phosphate from [$\gamma$-$^{32}$P]-ATP into a substrate molecule after treatment with a subject compound, relative to a control, by measuring the beta-particle emission rate using a scintillation counter or phosphorimaging. In certain embodiments, the subject compounds have an $IC_{50}$ value for UCK2 of less than about 1 µM, less than about 0.2 µM, less than about 0.1 µM, less than about 10 nM, less than about 1 nM, or even less. The inhibitor may be selective for UCK2. In some embodiments, the potency of the UCK2 inhibiting compounds track with the ability to reduce the toxicity of the DHODH inhibitor.

In certain embodiments, the UCK2 inhibitor has no significant effect on the viability of a mammalian cell, as determined by a cell cytotoxicity assay, e.g., as determined by administering a subject compound to a HeLa cell and determining the number of viable cells present. The subject compounds may exhibit a % cell viability, as compared to a control (e.g., a DMSO control), of 15% or more, such as 20% or more, 30% or more, 40% or more, 50% or more, 60% or more, 70% or more, 80% or more, 90% or more, 100% or more, 120% or more, or even higher. The subject compounds may exhibit a $CC_{50}$ value of 1 nM or higher, such as 100 nM or higher, 300 nM or higher, 1 µM or higher, 3 µM or higher, 5 µM or higher, 10 µM or higher, 20 µM or higher, 30 µM or higher, 50 µM or higher, or even higher. The combination of the UCK2 inhibitor and the DHODH inhibitor may have a cellular toxicity profile that is substantially less toxic than the DHODH inhibitor administered as a single agent, e.g. a reduction in toxicity of at least about 50%, at least about 90%, at least about 99%, or more.

In certain embodiments, the combination of agents has a therapeutic index (e.g., the ratio of a compound's cytotoxicity (e.g., cell cytotoxicity, CC50) to bioactivity (e.g., antiviral activity, EC50)) that is 20 or more, such as 50 or more, 100 or more, 200 or more, 300 or more, 400 or more, 500 or more, or even more.

The combination of agents may inhibit virus replication for a virus of interest by 10% to 100%, e.g., by 10% or more, 20% or more, 30% or more, 40% or more, 50% or more, 60% or more, 70% or more, 80% or more, or 90% or more. In certain assays, a subject combination of agents may inhibit its virus target with an $IC_{50}$ of $1 \times 10^{-6}$ M or less (e.g., $1 \times 10^{-6}$ M or less, $1 \times 10^{-7}$ M or less, $1 \times 10^{-8}$ M or less, $1 \times 10^{-9}$ M or less, $1 \times 10^{-10}$ M or less, or $1 \times 10^{-11}$ M or less).

The protocols that may be employed in determining activity are numerous, and include but are not limited to cell-free assays, e.g., binding assays; assays using purified enzymes, cellular assays in which a cellular phenotype is measured, e.g., gene expression assays; and in vivo assays that involve a particular animal (which, in certain embodiments may be an animal model for a condition related to the target pathogenic virus).

Methods

The present disclosure provides methods of treating pathogenic virus infection by targeting a combination of host functions upon which the virus is dependent, thereby decreasing the ability of the virus to avoid the therapy by mutation. The methods also provide a broad platform for anti-infective therapies by targeting a host function.

Methods are also provided for treating, reducing, or preventing primary tumor growth or formation of primary cancer, or metastasis of cancers, by administering a combination of a agents as described herein. Administration may be combined with one or more additional cytoreductive therapies. The combination may increase the therapeutic index of the agents.

Cancers of interest include solid tumors and hematologic malignancies, e.g. leukemias and lymphomas; and include without limitation primary AML, primary ovarian cancer, primary breast cancer, primary lung cancer, primary liver cancer, primary colon cancer, primary gallbladder cancer, primary pancreatic cancer, primary prostate cancer, primary ovarian cancer, and/or primary glioblastoma. Methods of the present invention also include treating, reducing, or preventing tumor metastasis.

Aspects of the method include contacting a sample with a subject formulation (e.g., as described above) under conditions by which the formulation inhibits multiple pathways in pyrimidine synthesis and salvage. Any convenient protocol for contacting the compound with the sample may be employed. The particular protocol that is employed may vary, e.g., depending on whether the sample is in vitro or in vivo. For in vitro protocols, contact of the sample with the compound may be achieved using any convenient protocol. In some instances, the sample includes cells that are maintained in a suitable culture medium, and the complex is introduced into the culture medium. For in vivo protocols, any convenient administration protocol may be employed. Depending upon the potency of the compound, the cells of interest, the manner of administration, the number of cells present, various protocols may be employed.

The term "sample" as used herein relates to a material or mixture of materials, typically, although not necessarily, in fluid form, containing one or more components of interest.

In some embodiments, the subject method is a method of treating a subject for an infective disease. In some embodiments, the subject method includes administering to the subject an effective amount of a formulation as described above. In some embodiments, the infective disease condition results from infection with a positive-stranded RNA virus, negative stranded RNA virus, or a dsRNA virus. In some embodiments, the infective disease condition results from infection with a pathogen selected from the group consisting of HCV, HIV1, HIV2, rhinovirus (e.g., B or C), Ebola virus, hantavirus, Japanese encephalitis virus, hepatitis A virus, and influenza virus, Poliovirus, Enterovirus (e.g., A-D), West Nile Virus, and Dengue Virus (e.g., 1-4).

In some embodiments, the subject is human. In some embodiments, the compound is administered as a pharmaceutical preparation.

In some embodiments, where the subject method is a method of inhibiting viral infection, the method including contacting virus-infected cells with an effective dose of a combination described herein to inhibit viral replication. In some embodiments, the method further includes contacting the cells with an additional therapeutic agent, including without limitation deoxycytidine supplementation.

The subject compounds and methods find use in a variety of therapeutic applications. Therapeutic applications of interest include those applications in which pathogen infection is the cause or a compounding factor in disease progression. As such, the subject compounds find use in the treatment of a variety of different conditions in which the inhibition and/or treatment of viral infection in the host is desired.

Pharmaceutical Compositions

The above-discussed compounds can be formulated using any convenient excipients, reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject compound is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some embodiments, the subject compound is formulated for sustained release.

In some embodiments, the subject combination of agents is formulated with an additional antiviral agent, e.g. interferon, ribavirin, Enfuvirtide; RFI-641 (4,4"-bis-{4,6-bis-[3-(bis-carbamoylmethyl-sulfamoyl)-phenylamino]-(1,3,5) triazin-2-ylamino}-biphenyl-2,2"-disulfonic acid); BMS-433771 (2H-Imidazo(4,5-c)pyridin-2-one, 1-cyclopropyl-1,3-dihydro-3-((1-(3-hydroxypropyl)-1H-benzimidazol-2-yl) methyl)); arildone; Pleconaril (3-(3,5-Dimethyl-4-(3-(3-methyl-5-isoxazolyl)propoxy)phenyl)-5-(trifluoromethyl)-1,2,4-oxadiazole); Amantadine (tricyclo[3.3.1.1.3,7]decane-1-amine hydrochloride); Rimantadine (alpha-methyltricyclo[3.3.1.1.3,7]decane-1-methanamine hydrochloride); Acyclovir (acycloguanosine); Valaciclovir; Penciclovir (9-(4-hydroxy-3-hydroxymethyl-but-1-yl)guanine); Famciclovir (diacetyl ester of 9-(4-hydroxy-3-hydroxymethyl-but-1-yl)-6-deoxyguanine); Gancyclovir (9-(1,3-dihydroxy-2-propoxymethyl)guanine); Ara-A (adenosine arabinoside); Zidovudine (3'-azido-2',3'-dideoxythymidine); Cidofovir (1-[(S)-3-hydroxy-2-(phosphonomethoxy)propyl]cytosine dihydrate); Dideoxyinosine (2',3'-dideoxyinosine); Zalcitabine (2',3'-dideoxycytidine); Stavudine (2',3'-didehydro-2',3'-dideoxythymidine); Lamivudine ((−)β-L-3'-thia-2',3'-dideoxycytidine); Abacavir (1S,4R)-4-[2-amino-6-(cyclopropylamino)-9H-purin-9-yl]-2-cyclopentene-1-methanol succinate); Emtricitabine (−)-β-L-3'-thia-2',3'-dideoxy-5-fluorocytidine); Tenofovir disoproxil (Fumarate salt of bis(isopropoxycarbonyloxymethyl) ester of (R)-9-(2-phosphonylmethoxypropyl)adenine); Bromovinyl deoxyuridine (Brivudin); Iodo-deoxyuridine (Idoxuridine); Trifluorothymidine (Trifluridine); Nevirapine (11-cyclopropyl-5,11-dihydro-4-methyl-6H-dipyrido[3,2-b:2',3'-f][1,4]diazepin-6-one); Delavirdine (1-(5-methanesulfonamido-1H-indol-2-yl-carbonyl)-4-[3-(1-methylethyl-amino) pyridinyl) piperazine monomethane sulfonated); Efavirenz ((−)6-chloro-4-cyclopropylethynyl-4-trifluoromethyl-1,4-dihydro-2H-3,1-benzoxazin-2-one); Foscarnet (trisodium phosphonoformate); Ribavirin (1-β-D-ribofuranosyl-1H-1,2,4-triazole-3-carboxamide); Raltegravir (N-[(4-Fluorophenyhmethyl]-1,6-dihydro-5-hydroxy-1-methyl-2-[1-methyl-1-[[(5-methyl-1,3,4-oxadiazol-2-yl)carbonyl]amino]ethyl]-6-oxo-4-pyrimidinecarboxamide monopotassium salt); Neplanocin A; Fomivirsen; Saquinavir (SQ); Ritonavir ([5S-(5R,8R,10R,11R)]-10-hydroxy-2-methyl-5-(1-methylethyl)-1-[2-(methylethyl)-4-thiazolyl]-3,6-dioxo-8,11-bis (phenylmethyl)-2,4,7,12-tetraazatridecan-13-oic acid 5-thiazolylmethyl ester); Indinavir ([(1S,2R,5(S)-2,3,5-trideoxy-N-(2,3-dihydro-2-hydroxy-1H-inden-1-yl)-5-[2-[[(1,1-dimethylethyl)amino]carbonyl]-4-pyridinylmethyl)-1-piperazinyl]-2-(phenylmethyl- -erythro)pentonamide); Amprenavir; Nelfinavir; Lopinavir; Atazanavir; Bevirimat; Indinavir; Relenza; Zanamivir; Oseltamivir; Tarvacin; etc. are administered to individuals in a formulation (e.g., in the same or in separate formulations) with a pharmaceutically acceptable excipient(s).

The subject formulations can be administered orally, subcutaneously, intramuscularly, parenterally, or other route, including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ.

Each of the active agents can be provided in a unit dose of from about 0.1 µg, 0.5 µg, 1 µg, 5 µg, 10 µg, 50 µg, 100 µg, 500 µg, 1 mg, 5 mg, 10 mg, 50, mg, 100 mg, 250 mg, 500 mg, 750 mg or more. Administration may be every 4 hours, every 6 hours, every 12 hours, daily, every other day, weekly, or as empirically determined for the virus of interest and the host of interest.

The subject compounds may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

Subjects Amenable to Treatment Using the Compounds of the Disclosure

Individuals who have been clinically diagnosed as infected with a pathogen of interest are suitable for treatment with the methods of the present disclosure, as are individuals at risk of exposure. In particular embodiments of interest, individuals of interest for treatment according to the disclosure have detectable pathogen titer indicating active replication, for example a titer of at least about $10^4$, at least about $10^5$, at least about $5\times10^5$, or at least about $10^6$, or greater than 2 million genome copies of virus per milliliter of serum. Similar methods may be used to determine whether subjects infected with another pathogen are suitable for treatment using the subject methods.

The effectiveness of the anti-infective treatment may be determined using any convenient method. For example, whether a subject method is effective in treating a virus infection can be determined by measuring viral load, or by measuring a parameter associated with infection.

Viral load can be measured by measuring the titer or level of virus in serum. These methods include, but are not limited to, a quantitative polymerase chain reaction (PCR) and a branched DNA (bDNA) test. Many such assays are available commercially, including a quantitative reverse transcription PCR (RT-PCR) (Amplicor HCV Monitor™ Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) Ann. Intern. Med. 123:321-329.

For treatment of cancer, individuals who have been clinically diagnosed with a cancer are suitable for treatment with the methods of the present disclosure. In particular embodiments of interest, individuals of interest for treatment according to the disclosure have a cancer in which, relative to a control tissue matched normal cell, has upregulated expression of UCK2, e.g. increased by about 25%, by about 50%, by about 75%, by two-fold, or more.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present disclosure. All such modifications are intended to be within the scope of the claims appended hereto.

Parallel shRNA and CRISPR-Cas9 Screens Enable Drug Target Identification and Rational Design of a Broad Spectrum Antiviral Strategy Broad spectrum antiviral drugs targeting host processes have the potential to treat a wide range of viruses while reducing the likelihood of emergent resistance. Despite great promise as therapeutics, host-targeting antivirals that are both safe and effective remain largely elusive. Here we use parallel genome-wide high-coverage shRNA and CRISPR-Cas9 screens to identify the host cell target and mechanism of action of GSK983, a potent broad spectrum antiviral with unexplained cytotoxicity.

We show that GSK983 blocks both cell proliferation and dengue virus replication by inhibiting the de novo pyrimidine biosynthesis enzyme dihydroorotate dehydrogenase (DHODH). Interestingly, DHODH appeared as a hit in our shRNA knockdown screen but not in our CRISPR-Cas9 knockout screen. However, our CRISPR-Cas9 screen highlighted unique connections between pyrimidine metabolism and other major biological pathways (most notably, mTOR signaling). Guided by mechanistic insights from both genomic screens, we found that exogenous deoxycytidine markedly reduces GSK983 cytotoxicity but not antiviral activity, providing an attractive novel approach to improve the therapeutic window of DHODH inhibitors against RNA viruses.

Together, our results highlight the distinct advantages and limitations of each screening method for identifying small molecule drug targets and demonstrate the utility of parallel knockdown and knockout screens for comprehensively probing drug activity.

The development of effective broad spectrum antiviral therapies remains a highly attractive (but equally challenging) goal in drug discovery. Antivirals targeting host cell processes have great potential to demonstrate activity against a range of viruses, reduce the likelihood of mutational resistance, and serve as frontline therapies for rapidly emerging outbreaks of viral disease such as Ebola and influenza. However, extensive efforts to develop such drugs have been stymied by various factors, including on-target toxicity and limited in vivo activity.

Recently, cell-based phenotypic screens of chemical libraries have generated numerous host targeting broad spectrum antiviral lead compounds with unidentified targets and mechanisms of action. Thus, the development of improved methods for target identification and mechanism elucidation—critical challenges in drug discovery—should facilitate the development of more effective broad spectrum antiviral therapies.

High-throughput yeast deletion and RNAi-based screening approaches have emerged as powerful alternatives to drug target identification methods that utilize affinity-based chemoproteomics or chemical-genetic expression signatures. We recently developed high-coverage shRNA libraries (25 shRNAs/gene) that facilitate pooled genome-wide screening in mammalian cells with dramatically improved hit reliability. While our high coverage shRNA libraries have demonstrated utility in identifying small molecule drug targets, genome-wide screening is no longer limited to RNAi-mediated gene knockdown.

The recent development of the CRISPR-Cas9 system has greatly expanded the scope of genomic screening in mammalian cells by enabling facile interrogation of functional gene deletions. Here, we demonstrate a comprehensive strategy using parallel genome-wide shRNA and CRISPR-Cas9 screens to discover the previously unknown host cell target and mechanism of action of GSK983, a poorly understood broad spectrum antiviral lead compound.

We first examined the biological activity of GSK983 (FIG. 1a and FIG. 4a) in human K562 cells. GSK983 inhibited K562 cell growth with an IC50 of 21 nM (FIG. 1b and FIG. 4b), consistent with previous observations. Cell cycle analysis revealed that 24 h GSK983 treatment caused an accumulation of K562 cells in S phase (FIG. 4c,d), while prolonged 72 h treatment induced a dose dependent increase in K562 cell death by apoptosis (FIG. 4e,f).

To discover the cellular target and mechanism of action of GSK983, we identified genetic modifiers of GSK983 toxicity using parallel genome-wide shRNA and CRISPR-Cas9 screens (FIG. 1c,d). For drugs that block the activity of their target protein, shRNA-mediated knockdown of the gene encoding the drug target is expected to phenocopy pharmacological inhibition of the target protein. Therefore, GSK983 should be more toxic to cells expressing an shRNA against a gene encoding a protein target of the drug. Furthermore, we reasoned that we should be able to detect different types of genes (essential vs. non-essential) using the two screening approaches. The broad spectrum of shRNA-mediated knockdown efficiency should facilitate identification of essential genes that modulate GSK983 toxicity, while CRISPR-Cas9 mediated knockout should enable detection of non-essential genes that require full deletion to produce an observable phenotype. Thus, we anticipated that parallel screens would provide a more comprehensive picture of genetic interactions with the GSK983 target than either screening approach alone.

We previously established a platform for pooled RNAi screens using ultracomplex shRNA libraries (~25 shRNAs per gene and ~10,000 negative control shRNAs). More recently, we systematically optimized several features of our shRNA design to create a next-generation shRNA library, which performs comparably to our CRISPRi library. For the shRNA screen described here, K562 cells were infected with our next-generation shRNA library targeting the entire human protein-coding genome. For the CRISPR-Cas9 screen, we designed a CRISPR single-guide RNA (sgRNA) library targeting the entire human protein-coding genome (~4 sgRNAs per gene and ~2,000 negative control sgRNAs) incorporating previously reported improvements to the sgRNA stem loop. This CRISPR sgRNA library was stably infected into a K562 cell line constitutively expressing Cas9 endonuclease. For both screens, cells expressing the genome-wide shRNA or sgRNA library were split and grown in the presence or absence of 48 nM GSK983 for 10-14 days.

Genomic DNA was then isolated from untreated and GSK983-treated cells, and the shRNA- or sgRNA-encoding DNA constructs were PCR-amplified and counted by deep sequencing. Deep sequencing data from the shRNA screen was used to rank genes according to a maximum likelihood estimator (MLE) metric that we designed to consider the magnitude of sensitization to or protection against GSK983 conferred by the entire set of shRNAs targeting each gene. Deep sequencing data from the CRISPR-Cas9 screen was used to rank genes according to the median fold-change in sgRNA frequency in the untreated versus GSK983-treated cell populations (Tables 5,6).

Figure 5A:
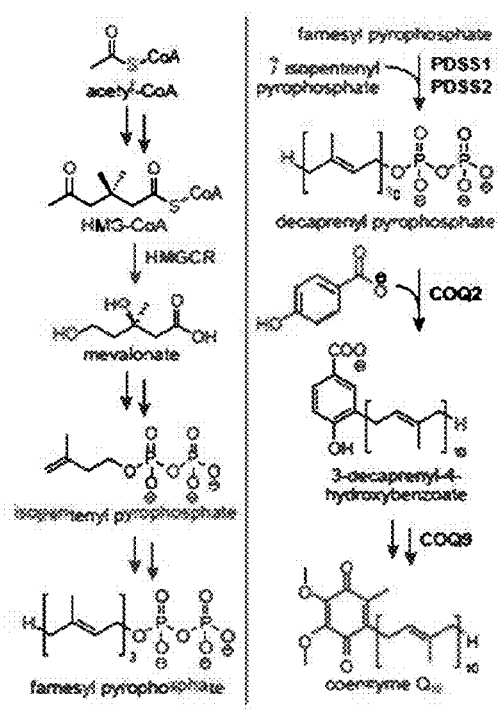
FIG. 5A-5B.
Figure 5B:
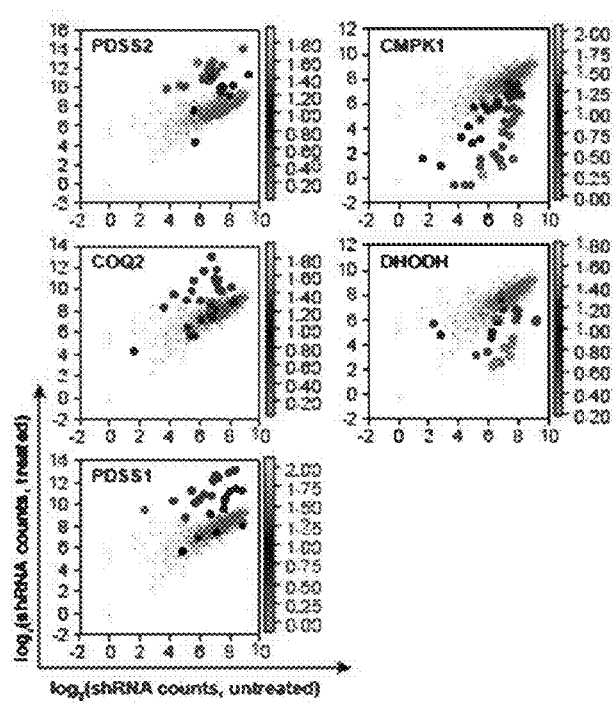

Inspection of the top 10 hit genes from both screens revealed clear signatures from three major biological pathways (FIG. 1e). Knockdown or knockout of genes whose products are required for coenzyme Q10 (CoQ10) biosynthesis and function (HMGCR, PDSS1, PDSS2, COQ2, COQ9, and COQ10B) protected K562 cells against GSK983 (FIG. 1e and FIG. 5a,b). In contrast, shRNA-mediated knockdown of pyrimidine metabolism genes (DHODH and CMPK1) sensitized K562 cells to GSK983 (FIG. 1e and FIG. 5b), as did CRISPR-Cas9-mediated knockout of components of the GATOR1 protein 4 complex (NPRL2 and DEPDC5), a recently identified negative regulator of mTORC1 activity (FIG. 1e). Interestingly, mammalian pyrimidine biosynthesis utilizes CoQ10 and is subject to regulation by mTORC1.

As expected, genes required for essential processes such as nucleotide biosynthesis (e.g., DHODH and CMPK1) that appeared as top hits in the shRNA knockdown screen did not appear as statistically significant hits in the CRISPR-Cas9 deletion screen (FIG. 1f). Conversely, certain genes (e.g., mTOR signaling components NPRL2, TSC2, SEH1L, MAPKAP1, RICTOR, RHEB, and TBC1D7) were statistically significant hits in the CRISPR-Cas9 screen but not in the shRNA screen (FIG. 1f and Table 6). A number of genes were statistically significant hits in both screens, including PDSS1, PDSS2, and UCK2.

GO enrichment analysis of the top 50 hits from each screen revealed that CoQ10 biosynthesis genes were significantly overrepresented among top hits from both screens, while pyrimidine metabolism genes were significantly overrepresented among top hits from the shRNA screen alone (p<0.001 in all cases) (Tables 1,2). Thus, our findings demonstrate the complementary power of parallel shRNA and CRISPR-Cas9 screens to identify connections between biological pathways that may be difficult to detect using either screening approach alone.

Multiple shRNAs targeting top hit genes were individually retested to validate genomic screen results. Using a competitive growth assay, we verified both the sensitized phenotype conferred by DHODH or CMPK1 knockdown and the protected phenotype conferred by knockdown of several CoQ10 biosynthesis genes (FIG. 1g and FIG. 6a-c). We also used QPCR to confirm the efficacy of selected shRNAs targeting DHODH and CMPK1 (FIG. 6d,e). Similarly, top hit sgRNAs from the CRISPR-Cas9 screen were individually retested to verify both that NPRL2 or DEPDC5 knockout sensitized K562 cells to GSK983 and that knockout of CoQ10 biosynthesis genes protected K562 cells against the drug (FIG. 1h,i and FIG. 7a).

Figure 7A:
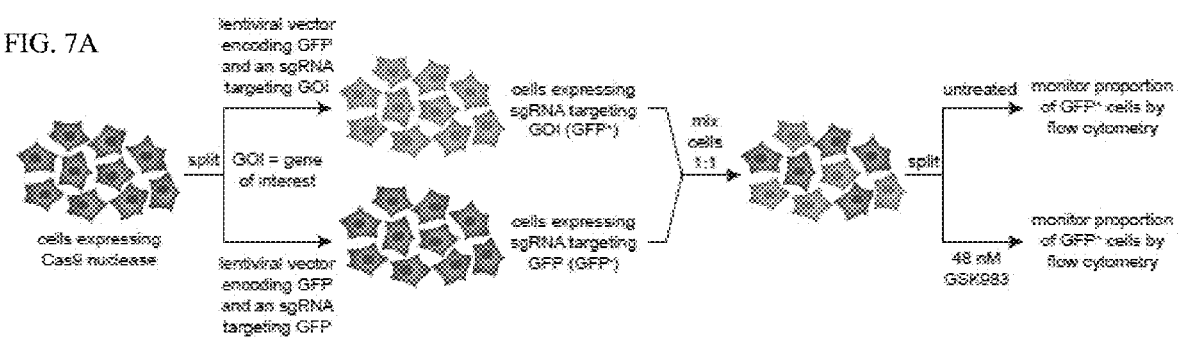
FIG. 7A-7B.
Figure 7B:
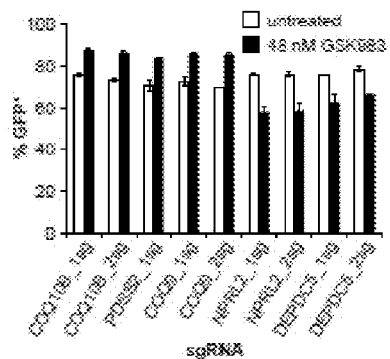

CRISPR sgRNAs targeting selected top hit genes were retested in HeLa cells and gave similar results, albeit with milder phenotypes, indicating that these genetic modifiers of GSK983 sensitivity are not K562-specific (FIG. 7a,b). While the CRISPR-Cas9 and shRNA screens collectively provided a more complete understanding of the biological activity of GSK983, we considered that the highly sensitizing hits in the pyrimidine biosynthesis pathway were among the most likely candidates to be molecular targets of GSK983.

Given that cells expressing an shRNA against a molecular target of GSK983 should be highly sensitized to GSK983-induced growth inhibition, we focused our target identification effort on the pyrimidine metabolism genes DHODH and CMPK1, which were the top sensitizing hits from our genome-wide shRNA screen. Mammalian cells derive pyrimidine (deoxy)ribonucleotide triphosphates either from de novo biosynthesis or pyrimidine salvage, in which intact pyrimidine metabolites are recycled from intracellular nucleic acid degradation or imported into the cell from exogenous sources (FIG. 2a). DHODH (dihydroorotate dehydrogenase) is required for de novo pyrimidine biosynthesis, while CMPK1 plays a critical role in both de novo biosynthesis and pyrimidine salvage (FIG. 2a).

Figure 8A:
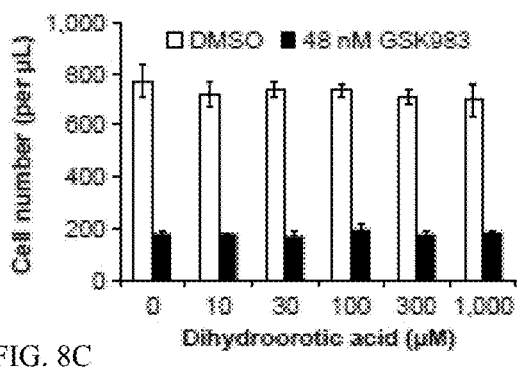
Figure 8A:
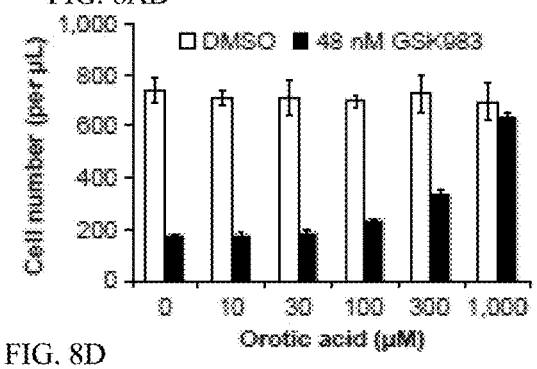

To determine whether GSK983 inhibited DHODH, we examined the ability of dihydroorotate and orotate (the substrate and product of DHODH, respectively) to reverse the anti-proliferative effect of GSK983 in K562 cells. Dihydroorotate supplementation had no effect on GSK983-induced growth inhibition (FIG. 2b). In sharp contrast, exogenous orotate reversed the anti-proliferative effect of GSK983 in dose-dependent fashion, with full rescue of K562 cell growth at the highest orotate concentration tested (FIG. 2c). We obtained identical results in HeLa cells (FIG. 8a,b). Together, these data strongly suggested that GSK983 is a DHODH inhibitor.

Figure 8C:
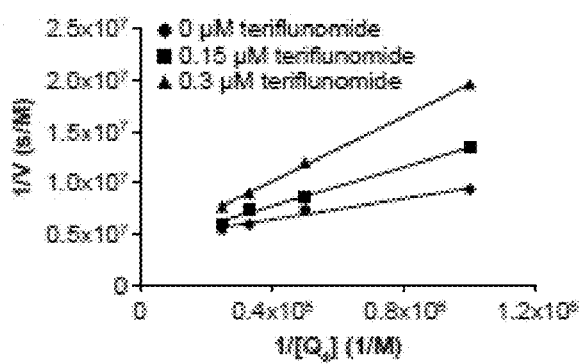
Figure 8D:
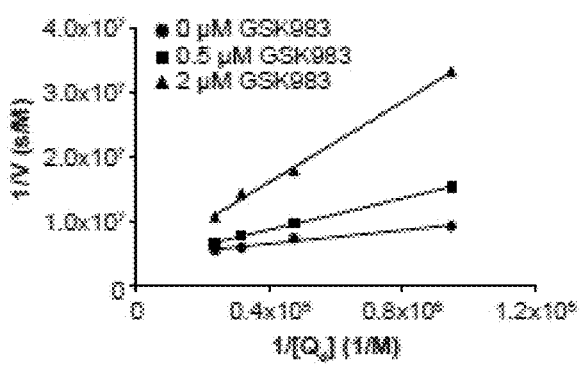
Figure 8E:
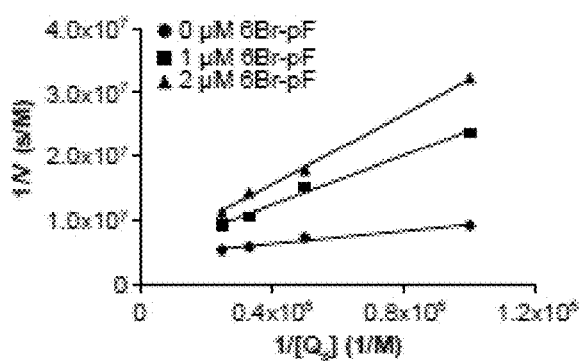
Figure 8F:
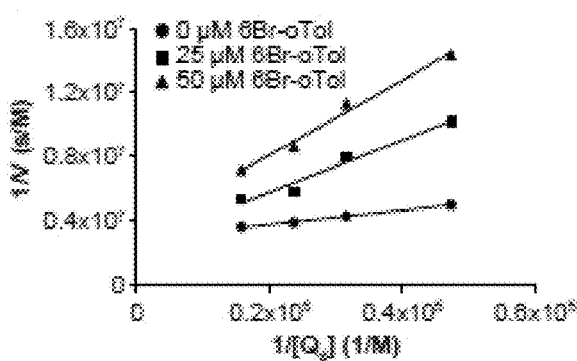
Figure 8G:
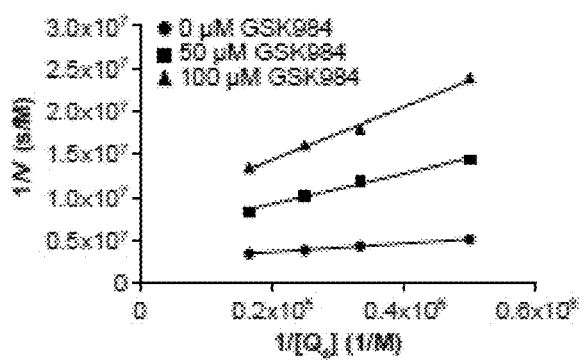

To confirm DHODH as a GSK983 target, we expressed and purified the recombinant human enzyme from E. coli and examined the effect of GSK983 on in vitro enzyme activity, using the known DHODH inhibitor teriflunomide as a positive control (reported Ki =179 nM)37. GSK983 was a competitive inhibitor of DHODH with respect to decylubiquinone binding (Ki=403 nM) (FIG. 2d and FIG. 8c,d).

To determine whether the reported antiviral effect of GSK983 could be attributed to DHODH inhibition, three GSK983 analogues originally prepared and evaluated at GlaxoSmithKline were resynthesized. The extent to which each compound (GSK983, 6Br-pF, 6Br-oTol, and GSK984) inhibited DHODH activity in vitro correlated strongly with the reported potency of each compound in cell-based antiviral assays (R2=0.993) (FIG. 2d,e and FIG. 8d-g). Collectively, these findings indicated that the antiviral effect of GSK983 is due to DHODH inhibition.

To determine whether GSK983 inhibited CMPK1, we expressed and purified the recombinant human enzyme from E. coli; however, we observed no effect of GSK983 on in vitro CMPK1 activity. Thus, although CMPK1 was the most sensitizing hit in the shRNA screen (followed by DHODH), the encoded protein is not a direct GSK983 target. Nonetheless, it is logical that shRNA-mediated CMPK1 knockdown is highly toxic in the presence of GSK983, given that CMPK1 knockdown should further impair both de novo pyrimidine biosynthesis and pyrimidine salvage (FIG. 2a). While there are examples of small molecule DHODH inhibitors that potently block virus replication, prolonged treatment with DHODH inhibitors causes pyrimidine depletion that arrests the growth of rapidly dividing cells. Indeed, the FDA-approved drugs leflunomide (rheumatoid arthritis) and teriflunomide (multiple sclerosis) are DHODH inhibitors that prevent the rapid clonal expansion of activated lymphocytes, a process which requires greatly expanded cellular pyrimidine pools. We were therefore interested in separating the antiviral effect of GSK983 from its anti-proliferative (and cytotoxic) effect on rapidly dividing cells.

Figure 9A:
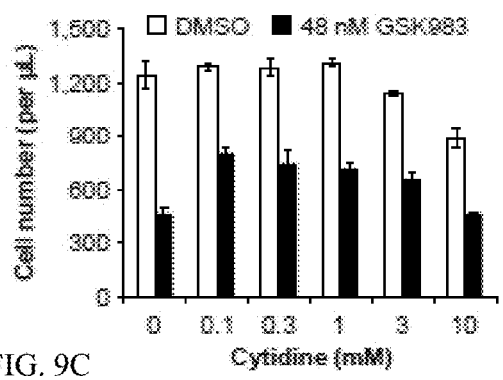
FIG. 9A-9E.
Figure 9B:
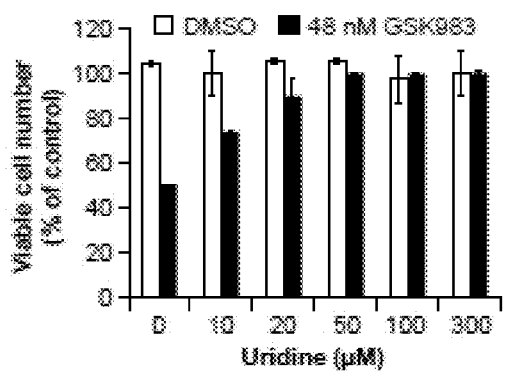

Guided by the appearance of pyrimidine salvage enzymes among the top sensitizing hits from both genomic screens, we examined the ability of pyrimidine salvage metabolites to reverse the anti-proliferative effect of GSK983 on rapidly dividing cells. Uridine, cytidine, or deoxycytidine supplementation reversed GSK983-induced growth inhibition to varying extents in K562 cells (FIG. 3a,b and FIG. 9a,b). However, cellular salvage of exogenous ribonucleosides (uridine and cytidine) can sustain RNA virus replication despite DHODH inhibition. We reasoned that deoxycytidine salvage would support DNA but not RNA virus replication given that ribonucleotides cannot be directly biosynthesized from their 2'-deoxy analogues. This raised the intriguing possibility of using a DHODH inhibitor to block RNA virus replication in combination with a deoxycytidine supplement to reverse the antiproliferative effect on rapidly dividing cells.

Figure 3C:
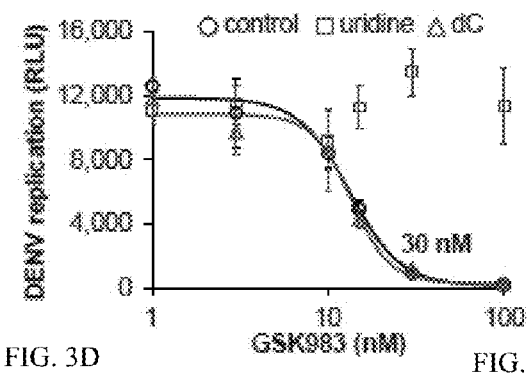

To test this therapeutically relevant hypothesis, we studied the antiviral effect of GSK983 on dengue virus (DENV), an RNA virus that has rapidly emerged as the most prevalent mosquito transmitted virus worldwide and currently causes approximately 100 million infections annually in tropical regions. We compared the effects of exogenous uridine and deoxycytidine on the ability of GSK983 to inhibit DENV replication in human A549 cells. In the absence of exogenous pyrimidines, GSK983 potently inhibited DENV replication (IC50=13.3 nM) (FIG. 3c). As expected, uridine supplementation completely abolished the antiviral activity of GSK983 (FIG. 3c). In sharp contrast, exogenous deoxycytidine did not reverse GSK983-mediated inhibition of DENV replication (IC50=13.5 nM) (FIG. 3c).

Figure 3E:
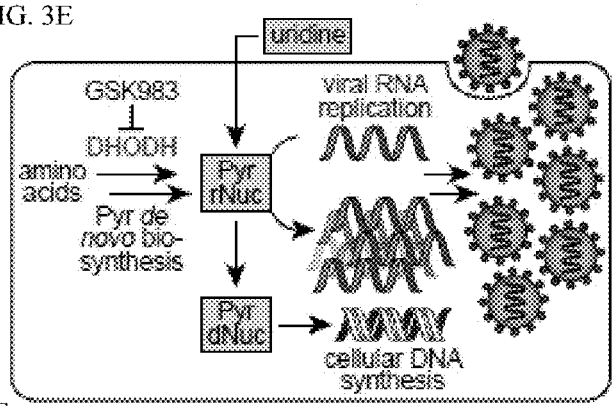
Figure 3D:
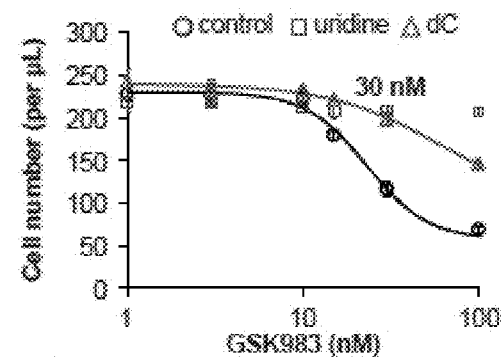
Figure 3F:
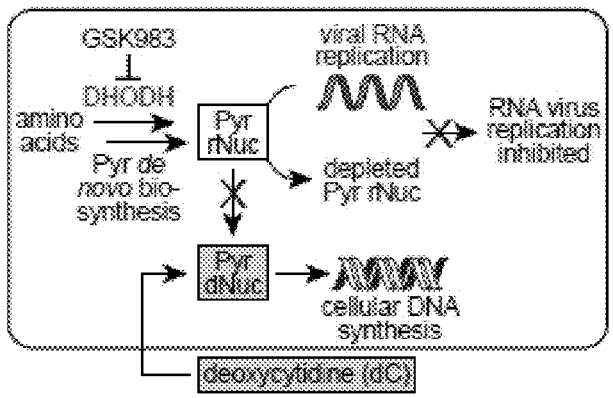
Figure 3G:
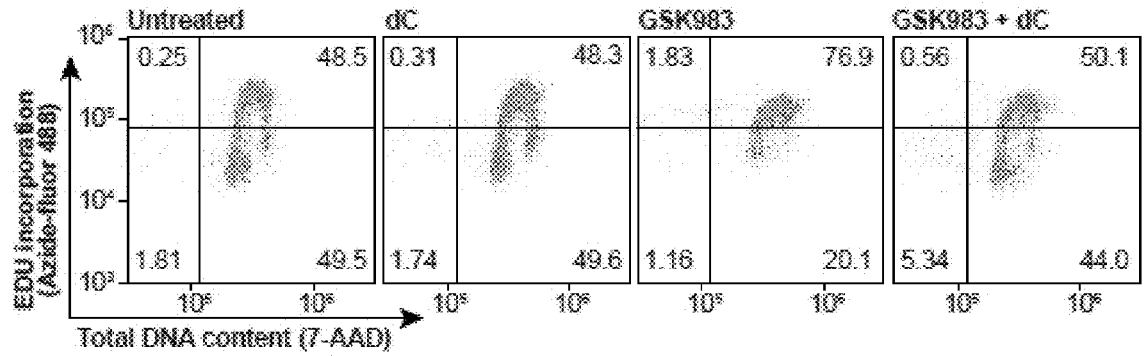

A cell growth assay conducted in parallel with antiviral experiments confirmed that both uridine and deoxycytidine reduced GSK983 cytotoxicity and rescued A549 cell growth (FIG. 3d), consistent with previous results in K562 cells. Notably, treatment with 30 nM GSK983 and 1 mM deoxycytidine caused a significant (~90%) reduction in DENV replication (FIG. 3c) with a minimal effect on A549 cell growth (FIG. 3d). Thus, deoxycytidine supplementation partially reversed the anti-proliferative effect of GSK983 but did not preclude potent inhibition of DENV replication (FIG. 3e,f).

Figure 9C:
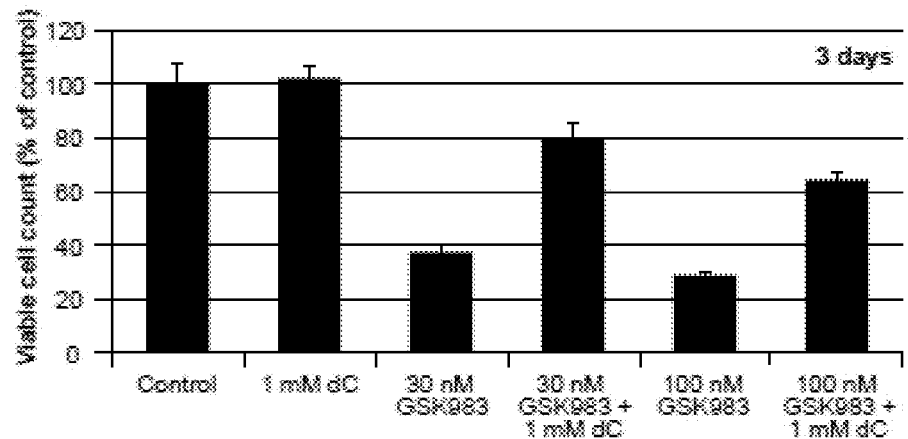
Figure 9D:
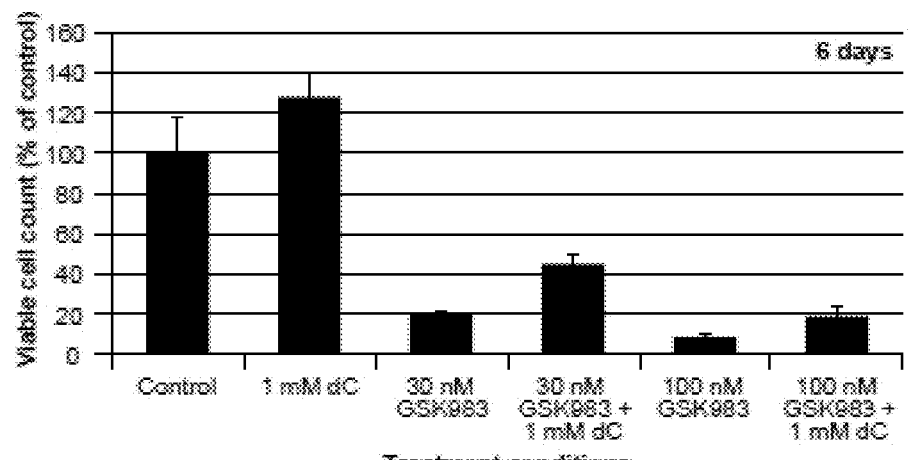
Figure 9E:
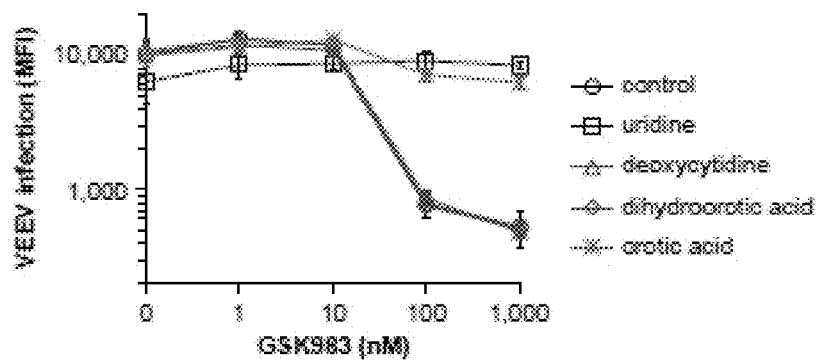

We additionally tested the effect of GSK983 on the replication of another RNA virus, Venezuelan equine encephalitis virus (VEEV). GSK983 inhibited VEEV replication with an IC50 of 12.8 nM (FIG. 9e). As with DENV, we observed that exogenous uridine reversed the antiviral effect of GSK983, while deoxycytidine supplementation had no effect on antiviral activity. Furthermore, we found that exogenous orotic acid, but not dihydroorotic acid, reversed the antiviral effect of GSK983. Collectively, these results indicate that GSK983 potently inhibits replication of RNA viruses by inhibiting cellular DHODH.

Figure 10A:
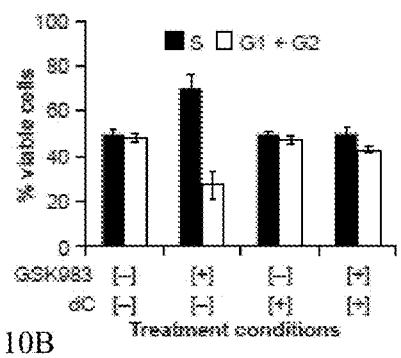
FIG. 10A-10F.
Figure 10B:
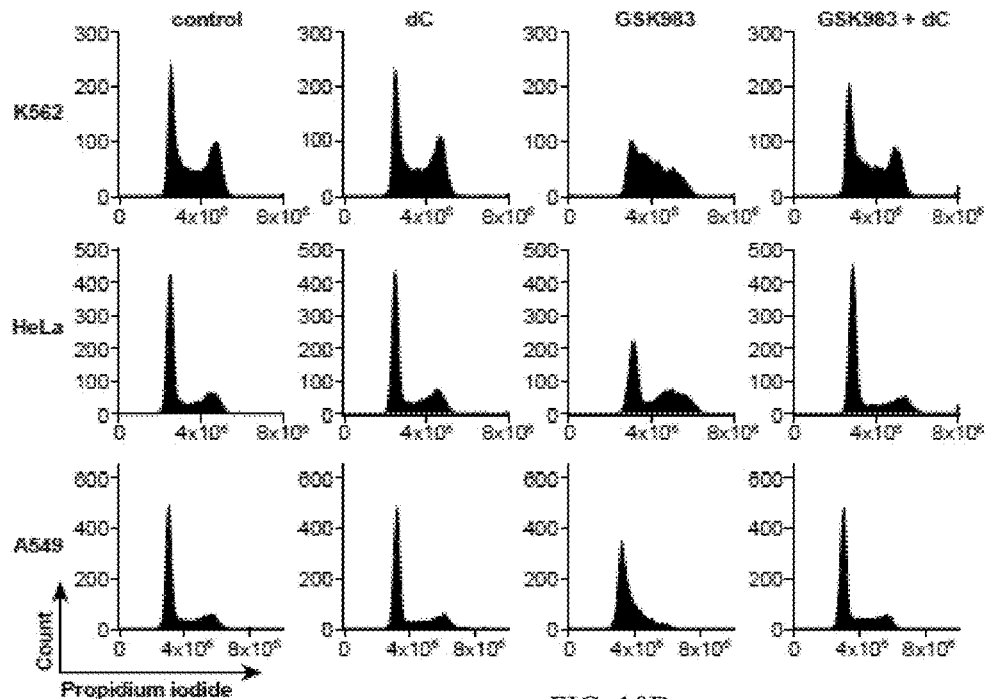
Figure 10C:
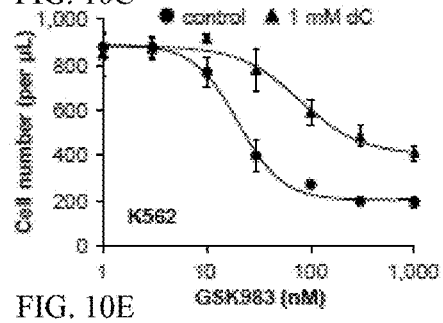
Figure 10D:
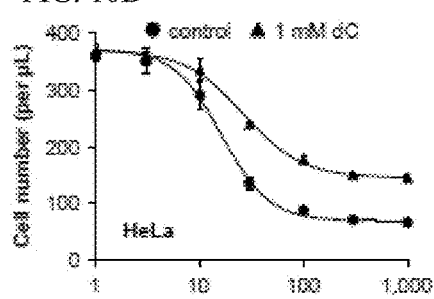
Figure 10E:
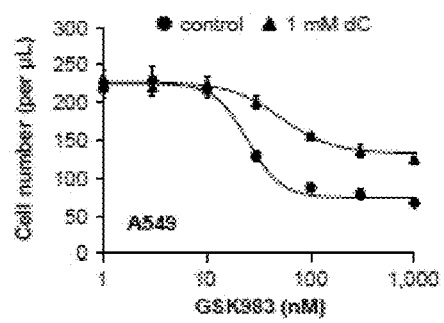
Figure 10F:
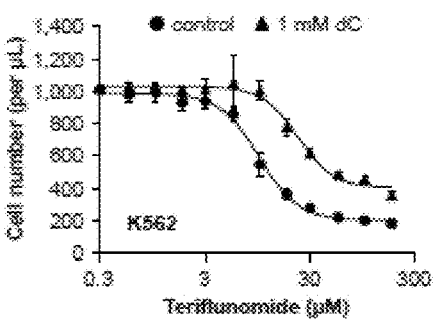

Further analysis revealed that exogenous deoxycytidine reversed GSK983-induced S phase cell cycle arrest (FIG. 4g and FIG. 10a,b) and cytotoxicity (FIG. 10c-e) at 3 days in K562, HeLa, and A549 cells. Deoxycytidine supplementation also markedly reduced teriflunomide toxicity in K562 cells (FIG. 10f. These findings suggest that deoxycytidine may reverse the anti-proliferative effect of DHODH inhibitors by sustaining cellular DNA synthesis during S phase. We observed that the capacity of exogenous deoxycytidine to reverse GSK983 toxicity is significant but diminished during extended GSK983 treatment (6 days) (FIG. 9c,d), likely due to the inability of deoxycytidine to alleviate the blockade of cellular RNA biosynthesis caused by pharmacological inhibition of DHODH.

Data from our genome-wide shRNA and CRISPR-Cas9 screens also suggested a novel combination chemotherapy to achieve improved activity against RNA viruses by targeting host pyrimidine metabolism. Both shRNA-mediated knockdown and CRISPR-Cas9-mediated deletion of the pyrimidine metabolism enzyme UCK2 (uridine-cytidine kinase) sensitized K562 cells to GSK983, presumably by impairing uridine and cytidine salvage (FIG. 2a). This result demonstrates that pharmacological inhibition of UCK2 can enhance the antiviral activity of a DHODH inhibitor by preventing flux through the ribonucleoside salvage pathway from sustaining RNA virus replication.

An effective and specific UCK2 inhibitor can act synergistically with a DHODH inhibitor to achieve improved activity against RNA viruses. Notably, UCK2 inhibition would not impair deoxycytidine salvage, which proceeds via a different pathway (FIG. 2a). Therefore, the possibility of using deoxycytidine to reduce the toxicity of a combination therapy targeting UCK2 and DHODH would still remain a viable additional therapy.

In summary, we have demonstrated the utility of parallel genome-wide shRNA and CRISPRCas9 screens for identifying the target and mechanism of action of a poorly understood therapeutic lead compound, a strategy which should be broadly applicable to other bioactive small molecules. We report for the first time that the host-targeting broad spectrum antiviral compound GSK983 inhibits cellular DHODH to produce the observed cytotoxic and antiviral effects. Furthermore, we show that co-administration of exogenous deoxycytidine largely reverses the cytotoxic antiproliferative effect of DHODH inhibitors without precluding potent activity against an RNA virus in cell-based assays.

Mechanistic insights from genomic screen data indicate that the efficacy of antiviral therapies targeting host pyrimidine metabolism can be improved by using DHODH and UCK2 inhibitors in combination. Finally, our dual genomic screening strategy identified other major biological pathways (mTOR regulation and CoQ10 biosynthesis) that affect cellular pyrimidine metabolism. Together, our results highlight the importance of genome-wide knockdown and knockout screening as a means of comprehensively interrogating both essential and non-essential genes, and demonstrate the utility of this approach as a functional platform enabling small molecule target identification and rational therapy design.

TABLE 1

Results of GO analysis (top 50 hits from the shRNA screen).

| GO Category | p-value |
| --- | --- |
| quinone biosynthetic process | 0.000560487 |
| pyrimidine nucleoside monophosphate biosynthetic process | 0.000560487 |
| ubiquinone biosynthetic process | 0.000560487 |
| pyrimidine ribonucleoside monophosphate biosynthetic process | 0.000560487 |
| UMP metabolic process | 0.000560487 |
| ubiquinone metabolic process | 0.000560487 |
| UMP biosynthetic process | 0.000560487 |
| pyrimidine ribonucleoside monophosphate metabolic process | 0.000560487 |
| pyrimidine nucleoside monophosphate metabolic process | 0.000603765 |
| isoprenoid biosynthetic process | 0.002040748 |
| ketone biosynthetic process | 0.002375797 |
| pyrimidine ribonucleoside biosynthetic process | 0.002375797 |
| pyrimidine ribonucleotide biosynthetic process | 0.002431869 |
| quinone metabolic process | 0.002564597 |
| pyrimidine ribonucleotide metabolic process | 0.002564597 |
| pyrimidine nucleotide biosynthetic process | 0.003433603 |
| pyrimidine nucleoside biosynthetic process | 0.003803045 |
| pyrimidine ribonucleoside metabolic process | 0.00418987 |
| pyrimidine-containing compound biosynthetic process | 0.005278701 |
| pyrimidine nucleotide metabolic process | 0.007333439 |

TABLE 2

Results of GO analysis (top 50 hits from the CRISPR-Cas9 screen).

| GO Category | p-value |
| --- | --- |
| ubiquinone metabolic process | $6.32667 \times 10^{-9}$ |
| ubiquinone biosynthetic process | $1.51045 \times 10^{-7}$ |
| quinone metabolic process | $1.51045 \times 10^{-7}$ |
| cellular ketone metabolic process | $1.51045 \times 10^{-7}$ |
| quinone biosynthetic process | $1.88033 \times 10^{-7}$ |
| oxidoreduction coenzyme metabolic process | $1.88033 \times 10^{-7}$ |
| coenzyme biosynthetic process | $2.31975 \times 10^{-6}$ |
| ketone biosynthetic process | $2.71449 \times 10^{-6}$ |
| coenzyme metabolic process | $9.20268 \times 10^{-6}$ |
| cofactor biosynthetic process | $9.20268 \times 10^{-6}$ |
| cofactor metabolic process | $5.80963 \times 10^{-5}$ |
| protein tetramerization | 0.000510309 |
| isoprenoid biosynthetic process | 0.003560433 |

Materials and Methods
Chemicals and Reagents for Biological Assays

GSK983 was synthesized as described below. Teriflunomide was obtained from Sigma-Aldrich and was used as received. GSK983 and teriflunomide were dissolved in DMSO to prepare stock solutions which were diluted in the appropriate cell growth medium for biological assays. GSK983 and teriflunomide stock solutions in DMSO were stored at −80° C. Uridine, cytidine, deoxycytidine, and dihydroorotic acid were obtained from Sigma-Aldrich. Orotic acid was obtained from Fisher Scientific. For pyrimidine supplementation experiments, pyrimidine metabolites (uridine, cytidine, deoxycytidine, orotic acid, and dihydroorotic acid) were dissolved directly in the appropriate growth medium (RPMI or DMEM). 5-Ethynyl-2'-deoxyuridine (EdU) and Azide-fluor 488 were obtained from Sigma-Aldrich and dissolved in DMSO to prepare working stock solutions. Copper (II) sulfate ($CuSO_4$) and ascorbic acid were obtained from Sigma-Aldrich and were used as received. 7-aminoactinomycin D (7-AAD) was obtained from Life Technologies and dissolved in DMSO to prepare a working stock solution.

Cell culture K562 cells (ATCC) were cultured in RPMI (Gibco) supplemented with 10% fetal bovine serum (FBS), penicillin/streptomycin, and L-glutamine. HeLa cells (HeLa-Kyoto cells, a gift from AA Hyman) and A549 cells (ATCC) were cultured in DMEM (Gibco) supplemented with 10% FBS, penicillin/streptomycin, and L-glutamine. In biological assays, HeLa cells and A549 cells were detached from the growth surface using a trypsin/EDTA solution (Gibco) prior to analysis. Cells were maintained in logarithmic growth during all biological assays. All cell lines were maintained in a humidified incubator (37° C., 5% $CO_2$), and checked regularly for mycoplasma contamination.

GSK983 dose response and growth time course in K562 cells. To determine the dose response of K562 cells to GSK983, K562 cells were seeded into 24-well plates at a density of 50,000 cells/mL and treated with GSK983 at the indicated concentration for 72 h. Following 72 h treatment, cells were harvested and the density of viable cells was determined by flow cytometry (FSC/SSC) using a BD Accuri C6 Flow Cytometer. $IC_{50}$ values were calculated by fitting a 4-parameter logistic equation to the data. To analyze the time-dependence of GSK983-induced growth inhibition in K562 cells, cells were seeded into 24-well plates at a density of 50,000 cells/mL and treated with the indicated concentration of GSK983. At the indicated time points, cells were harvested and the density of viable cells was determined by flow cytometry (FSC/SSC) using a BD Accuri C6 Flow Cytometer.

Cell cycle analysis based on total DNA content (propidium iodide). K562 cells were seeded into 6-well plates at a density of 100,000 cells/mL. HeLa and A549 cells were seeded into 6-well plates at a density of 200,000 cells/well. Cells were treated with the indicated concentration of GSK983 for 24 h. Where specified, cells were treated for 24 h with deoxycytidine alone (1 mM), GSK983 and deoxycytidine (1 mM), or neither (untreated). Following 24 treatment, cells were harvested and pelleted (300 g, 5 min). The supernatant was removed by vacuum and the cells were washed (0.5 mL 1×PBS). Cells were resuspended in 70% EtOH (1 mL, 0° C.) with mild vortexing. Cells were fixed in 70% EtOH overnight at 4° C. The following day, fixed cells were pelleted (1900 g, 5 min), washed (0.5 mL 1×PBS), and resuspended in 200 μL of a total DNA content staining solution (1×PBS with 50 μg/mL RNase A and 10 μg/mL propidium iodide). Samples were incubated for 30 min at 37° C. and analyzed by flow cytometry using a BD Accuri C6 Flow Cytometer. Propidium iodide fluorescence was detected in FL2.

Annexin V-FITC/7-AAD apoptosis assay. K562 cells were seeded into 24-well plates at a density of 50,000 cells/mL and treated with the indicated concentration of GSK983 for 72 h. The final concentration of DMSO in each well was <0.1%. Following 72 h GSK983 treatment, cells were harvested and pelleted (399 g, 5 min). The supernatant was removed by vacuum. Cell death by apoptosis was analyzed using a BioVision Annexin V-FITC Apoptosis Kit (catalog number K101-100). A staining solution was prepared by first diluting the provided Annexin V-FITC solution in binding buffer according to the specifications of the manufacturer. 7-AAD was added from a stock solution in DMSO (0.67 mg/mL) such that the final concentration of 7-AAD in the staining solution was 2.5 µg/mL. Cell samples were resuspended in 0.5 mL of the staining solution. Samples were incubated at room temperature for 10 min in the dark and analyzed by flow cytometry using a BD Accuri C6 Flow Cytometer. FITC fluorescence was detected in FL1 and 7-AAD fluorescence was detected in FL3.

Genome-wide shRNA screen. We infected our next-generation genome-wide lentiviral shRNA library into K562 cells as described previously. Infected cells were expanded and split into two flasks. In one flask, cells were grown in the presence of 48 nM GSK983 for 14 days, while in the other flask, cells were grown in the absence of GSK983. Untreated cells were diluted to a density of 500,000 cells/mL each day. GSK983-treated cells were diluted to a density of 500,000 cells/mL as needed. After the cell culture period, untreated and GSK983-treated cells were pelleted by centrifugation. Genomic DNA was isolated and shRNA encoding-constructs were counted by deep sequenced as described previously.

Genome-wide CRISPR-Cas9 screen. To conduct the CRISPR-Cas9 screen, we first designed a genome-wide CRISPR sgRNA library with 4 sgRNAs/gene, incorporating previously reported improvements to the sgRNA Cas9 binding region[30]. Coding sequence models for sgRNA design were based on CCDS. sgRNAs were targeted toward the 5' end of transcripts, and sgRNAs targeted exons common to all transcripts wherever possible. sgRNAs were 19-25 base pairs long and were adjacent to an NGG at the 3' end. sgRNAs also contained an endogenous 5'G. Where multiple possible sgRNA lengths existed, only one was picked at random to ensure that no two sgRNAs targeted the same PAM. sgRNAs were scored for off-targets as previously described and the most stringent score (e39 m1) was used wherever possible. Negative control sgRNAs were designed against scrambled coding sequences and filtered for zero off-targets in the genome. We generated a K562 cell line stably expressing Cas9 endonuclease by infecting K562 cells with SFFV-Cas9-BFP, which is identical to a vector described previously[23] but containing Cas9 with both active catalytic sites. We infected our newly designed lentiviral genome-wide sgRNA library into Cas9-expressing K562 cells according to the procedures described for lentiviral infection of shRNA libraries. Infected cells were expanded and split into two flasks. In one flask, cells were initially treated with 6 and 12 nM GSK983 with little effect; therefore the concentration of GSK983 was increased to 48 nM to ensure strong selection. Cells were grown in the presence of 48 nM GSK983 for 10 days. In the other flask, cells were grown in the absence of GSK983. After the cell culture period, genomic DNA was isolated from the untreated and GSK983-treated cells using a Qiagen DNA Blood Maxi kit according to the manufacturer's instructions.

To prepare the sgRNA sequencing library, the integrated sgRNA-encoding constructs were PCR amplified using Agilent Herculase II Fusion DNA Polymerase with primers oMCB_1562 (5'-AGGCTTGGATTTCTATAACTTCG-TATAG CATACATTATAC-3') and oMCB_1563 (5'-ACAT-GCATGGCGGTAATACGGT TATC-3'). PCR reactions contained 5× Herculase buffer (20 µL), dNTPs (1 µL of 10 mM stock), genomic DNA (10 µg), primer oMCB_1562 (1 µL of 100 µM stock), primer oMCB_1563 (1 µL of 100 µM stock), Herculase II Fusion DNA Polymerase (2 µL), and water (to adjust final reaction volume to 100 µL). The number of PCR reactions was scaled to use all of the isolated genomic DNA from the untreated and GSK983-treated cells. The conditions for the PCR reaction were as follows: 1× 98° C./2 min, 18× 98° C./30 s, 59.1° C./30 s, 72° C./45 s, 1× 72° C./3 min. PCR amplicons from genomic DNA isolated from untreated cells were pooled, as were PCR amplicons from genomic DNA isolated from GSK983-treated cells. The pooled PCR amplicons from the untreated and GSK983-treated samples were further amplified in a subsequent PCR reaction using primer oMCB_1349 (5'-CAAGCA-GAAGACGGCATACGAGATGCACAAAAGGA AACT-CACCCT-3') and a bar-coded primer (5'-AATGATACGGC-GACCACCGAGAT CTACACG ATCGGAAGAGCACACGTCTGAACTCCAGTCAC NNNNNN CGACTC GGTG CCACTTTTTC-3'), where N's indicate Illumina index barcodes.

For the second PCR reaction, the reaction mixtures contained 5× Herculase buffer (20 µL), dNTPs (2 µL of 10 mM stock), an aliquot of the amplicon from the first PCR reaction (5 µL), oMCB_1439 (0.8 µL of 100 µM stock), barcoded primer (0.8 µL of 100 µM stock), Herculase II Fusion DNA Polymerase (2 µL), and water (69.4 µL). The conditions for the second PCR reaction were as follows: 1× 98° C./2 min, 20× 98° C./30 s, 59.1° C./30 s, 72° C./45 s, 1× 72° C./3 min. The PCR products from the untreated and GSK983-treated samples were separated by gel electrophoresis (20% TBE-PAGE, 120 V, 50 min), and then gel purified to obtain sgRNA sequencing libraries.

Ranking genes from genome-wide shRNA and CRISPR-Cas9 screens. Given the variance in the efficiency of shRNA-mediated gene knockdown, we developed a novel maximum likelihood estimator (MLE) to approximate the maximum effect size of the collective set of shRNAs targeting each gene. The distribution of shRNAs for a given gene was fit to a mixed model with three distributions: off-target, miss, and on-target. The off-target distribution corresponds to the shRNA knocking down a gene other than its intended target and is estimated from the distribution of all shRNAs other than the negative controls. The missed distribution corresponds to the shRNA having no effect and is estimated from the distribution of all negative control shRNAs. Both estimations were performed by Gaussian kernel smoother with the bandwidth determined by Scott's rule. Finally, the on-target distribution is the uniform distribution from 0 to I, where I is a fitted parameter and corresponds to the estimated effect size. This allows for the fact that a given shRNA can be anywhere from 0 to 100 percent effective at knocking down the targeted gene product. The relative contribution of the missed and the on-target distribution was also fitted, allowing for different numbers of shRNAs to be considered on-target. The contribution of the off-target distribution was fixed at 10% to allow for outliers. The significance of the MLE was tested using a log likelihood ratio, where the p-values were empirically determined by Monte-Carlo sampling of all shRNAs other than the negative controls.

To call and rank hit genes from the shRNA screen, enrichment values for each shRNA were first calculated as the log ratio of the frequency of the shRNA-encoding construct in genomic DNA isolated from the untreated and GSK983-treated cell populations. For each gene, the MLE described above was used to estimate both the effect of the set of shRNAs targeting the gene and a p-value representing the significance of that estimate. Genes were then filtered by significance under the Bonferroni correction at p<0.05 and ranked according to the effect size estimate. To rank genes from the CRISPR-Cas9 screen, we first filtered genes with fewer than four distinct targeting sgRNAs detected in the deep sequencing data. The effect size was then calculated as the median fold-enrichment value for the set of sgRNAs targeting a given gene. Custom Python scripts for analysis of both screens will be made available upon request.

GO enrichment analysis. GO enrichment analysis was performed using Enrichr (GO Biological Process option). Separate GO enrichment analyses were performed on the top 50 hit genes from the shRNA screen and the CRISPR-Cas9 screen. All p values were adjusted using the Benjamini-Hochberg correction for false discovery rate. Table 1 shows all enriched GO categories from the shRNA screen with p<0.01. Table 2 shows all enriched GO categories from the CRISPR-Cas9 screen with p<0.01.

Lentivirus production and lentiviral infections for individual shRNA retests. Pairs of oligonucleotides encoding shRNAs targeting top hit genes were annealed and ligated into the pMCB309 vector backbone, which was previously digested with BstXI and gel-purified. pMCB309 encodes two BstXI cut sites, puromycin resistance, and mCherry. Oligonucleotides were obtained from Integrated DNA Technologies (IDT). The sequences of the shRNA-encoding oligonucleotides were ligated into pMCB309 for individual retesting. To produce lentivirus for individual shRNA retests, Mirus transfection reagent (catalog number MIR2305) (2.5 µL) was added to DMEM containing no FBS (97.5 µL) and incubated at room temperature for 5 min. Meanwhile, pMCB309 containing the indicated shRNA-encoding insert (0.75 µg) was combined with 3rd generation lentiviral packaging components (pMDL, pRSV, and pMD2—available from Addgene) (0.75 µg). The total DNA mixture (pMCB309 with shRNA encoding insert+lentiviral packaging components) was added to the DMEM/Mirus mixture and incubated for 30 min at room temperature. Meanwhile, HEK293T cells were seeded into 6-well plates at a density of 1 million cells/well in 2 mL DMEM. Transfection mixtures were added to HEK293T cells drop-wise and cells were incubated for 24 h at 37° C. The following day, cells were supplemented with 3 mL fresh DMEM. Cells were incubated at 37° C. for an additional 48 h. To harvest the virus, the supernatant was collected and passed through a 0.45 µm syringe filter. To infect K562 cells with lentivirus, K562 cells were seeded into 24-well plates at a density of 100,000 cells/well in a volume of 100 µL. Polybrene (2 µL of a 4 mg/mL stock solution) was added to the cells, followed by 1 mL of the appropriate lentivirus stock. Cells were spin infected in 24-well plates for 2 h at 1000 g at 33° C. Following spin infection, cells were resuspended and pelleted (300 g, 5 min). The supernatant was removed by aspiration and the cells were resuspended in fresh RPMI growth medium and incubated for 72 h at 37° C. The cells were expanded into 6-well plates and grown in the presence of puromycin (1.0 µg/mL) for 3-5 days to select for infected cells. Following puromycin selection, cells were pelleted (300 g, 5 min) and resuspended in fresh RPMI growth medium.

Competitive growth assays for individual shRNA retests. Competitive growth assays for individual shRNA retests were conducted as follows: 250,000 K562 cells expressing a negative control shRNA or an shRNA targeting a gene of interest (mCherry+) and 250,000 uninfected K562 cells (mCherry−) were seeded into 24-well plates. Heterogeneous cell mixtures were cultured in the presence or absence of 48 nM GSK983 for 14 days. As in the genome-wide shRNA screen, untreated cells were diluted to a density of 500,000 cells/mL each day and GSK983-treated cells were diluted to a density of 500,000 cells/mL as needed. Two wells each of untreated cells and GSK983-treated cells were cultured for each shRNA retested. The proportion of mCherry+ cells was monitored by flow cytometry every 72 h using a BD Accuri C6 Flow Cytometer (mCherry fluorescence detected in FL3). Data was analyzed as follows: for each shRNA retested, the percentage of mCherry+ cells in the two untreated wells was averaged, as was the percentage of mCherry+ cells in the two GSK983-treated wells (FIG. 6b,c). The ratio of the average percentage of mCherry+ cells in the treated and untreated cell populations was calculated to give an mCherry enrichment ratio for each shRNA retested. Thus, an mCherry enrichment ratio <1 indicates that mCherry+ cells are depleted in the GSK983-treated cell population versus the untreated cell population. In contrast, an mCherry enrichment ratio >1 indicates that mCherry+ cells are enriched in the GSK983-treated cell population versus the untreated cell population. For each shRNA, the logarithm of the mCherry enrichment ratio was calculated. A Wilcoxon-Mann-Whitney U Test was performed to compare the log(mCherry enrichment ratio) values for the set of shRNAs targeting each hit gene to the log(mCherry enrichment ratio) values for the set of negative control shRNAs. Using this competitive growth assay, we confirmed that knockdown of DHODH and CMPK1 sensitized K562 cells to GSK983, while knockdown of COQ2, PDSS2, PDSS1, and COQ10B protected K562 cells against GSK983 in good agreement with genomic screen results [FIG. 1g; bar length represents average log(mCherry enrichment ratio) for each gene and error bars represent standard deviation of log (mCherry enrichment ratio) values for each gene].

qPCR to confirm efficacy of individual shRNA reagents. We confirmed the efficacy of shRNAs DHODH_1, DHODH_2, CMPK1_2, and CMPK1_4 using qPCR according to procedures described previously[16], and values were normalized first to levels of RPL19, and then to the first of two negative control shRNAs. The following primers were used for qPCR experiments: hRPL19-5" ATGTATCACA-GCCTGTACCTG hRPL19-3' TTCTTGGTCTCTTCCTC-CTTG
oMCB1679_CMPK1_qpcr_5'AAGGTTTCGAGAGCATT CCT oMCB1680_CMPK1_qpcr_3' TGAAAGGAAGCAAAGCACCT
oMCB1681_DHODH_qpcr2_5' AGTCACAGATGCCAT-TGGAG oMCB1682_DHODH_qocr2_3' GTCCCTC-CTCTCATGATCCA Lentivirus production and lentiviral infections for individual sgRNA retests. Pairs of oligonucleotides encoding sgRNAs targeting top hit genes were annealed and ligated into the pMCB306 vector backbone, which was previously double digested with BstXI and Blp1 and gel-purified. In addition to BstXI and Blp1 cut sites, pMCB306 encodes puromycin resistance and GFP. Oligonucleotides were obtained from Integrated DNA Technologies (IDT). The plasmid map will be provided upon request. sgRNA-encoding oligonucleotides were ligated into pMCB306 for individual retesting. Lentivirus production for single sgRNA retests, spin infection into K562 cells, and puromycin selection of infected K562 cells were performed exactly as described in the procedure for individual shRNA retests. Selected sgRNAs were also retested in HeLa cells. Lentiviral infection and puromycin selection of HeLa cells was performed as follows: HeLa cells were seeded into 24-well plates at a density of 50,000 cells/well. DMEM containing the appropriate lentivirus (1 mL) was added to each well and cells were incubated for 72 h at 37° C. Cells were expanded into 6-well plates and grown in the presence of puromycin (1 μg/mL) for 3-5 days to select for infected cells. DMEM containing puromycin was removed and the cells were re-plated in fresh growth medium.

Competitive growth assays for individual sgRNA retests. For competitive growth assays to retest individual sgRNAs in K562 cells, 250,000 cells expressing an sgRNA targeting a gene of interest (GFP+) and 250,000 cells expressing an sgRNA targeting GFP (GFP−) were seeded into 24-well plates. Cells were cultured in the presence or absence of 48 nM GSK983 for 12 days. Untreated cells were diluted to a density of 500,000 cells/mL each day and GSK983-treated cells were diluted to a density of 500,000 cells/mL as needed. Two wells each of untreated cells and GSK983-treated cells were cultured for each sgRNA retested. The proportion of GFP+ cells was monitored by flow cytometry every 48-72 h using a BD Accuri C6 Flow Cytometer (GFP fluorescence detected in FL1). For competitive growth assays to retest individual sgRNAs in HeLa cells, 10,000 cells expressing an sgRNA targeting a gene of interest (GFP+) and 10,000 cells expressing an sgRNA targeting GFP (GFP−) were seeded into 24-well plates. Plated cells were incubated for 24 h at 37° C. Following 24 h incubation, the growth medium in each well was removed and cells were provided fresh growth medium with or without 48 nM GSK983. Cells were cultured in the presence or absence of 48 nM GSK983 for 13 days. Cells were split back 8-fold every 72 h in order to ensure that cell growth remained logarithmic. Two wells each of untreated cells and GSK983-treated cells were cultured for each sgRNA retested. The proportion of GFP+ cells was monitored by flow cytometry every 72 h using a BD Accuri C6 Flow Cytometer (GFP fluorescence detected in FL1).

Cloning, expression, and purification of recombinant human DHODH. Endogenous human DHODH contains a 29 residue N-terminal mitochondrial signal peptide. Here, we expressed and purified a truncated DHODH lacking the N-terminal signal peptide (Δ29DHODH) to facilitate detergent-free purification and increase the solubility of the recombinant enzyme in aqueous buffers. Others have shown that the Δ29DHODH construct retains full catalytic activity despite the N-terminal truncation. The DNA sequence encoding human DHODH was PCR-amplified from a cDNA template (Origene, SC128197) using Δ29DHODH forward primer: 5'-ACGACAAGCATATGGCCACGGGAGAT-GAGCG-3' and Δ29DHODH reverse primer: 5'-GCGAC-CCGAATTCGGCCGCCGATGATCTGCTCCAATGGC-3'. The PCR reactions contained 1×GC-Rich Buffer (NEB), DMSO (4%), Phusion High-fidelity DNA Polymerase (NEB) (0.05 unit/μL), dNTPs (2 mM), MgCl$_2$ (1.5 mM), cDNA template (20 ng) and primers (1 μM each). An annealing temperature of 53.9° C. was used for PCR amplification. The amplified insert was cloned into pET21a using NdeI and EcoRI restriction sites to form a construct encoding Δ29DHODH with a C-terminal His$_6$ tag. Expression of recombinant human DHODH was performed as described previously.

Briefly, E. coli BL21 (DE3) cells were transformed with a pET21a plasmid containing an insert encoding Δ29DHODH. Single colony transformants were grown in a 37° C. shaker for 12-15 h in 50 mL of 2×YT medium (Sigma Aldrich) supplemented with 100 μg/mL ampicillin. A 20 mL aliquot of bacterial culture was centrifuged at 5000 g for 10 min. The supernatant was discarded, and the cell pellet was resuspended in fresh 2×YT medium (20 mL). The resuspended cells were added to 2 L of 2×YT medium containing 100 μg/mL ampicillin, and the culture was grown aerobically at 37° C. until A600 was ~0.6 to 0.8. IPTG (0.1 mM) and flavin mononucleotide (100 μM) were added and the culture was grown aerobically at 25° C. for an additional 20 h. Cells were harvested by centrifugation at 5000 g for 20 min at 4° C. The resulting cell paste was stored at −80° C. prior to protein purification.

Recombinant human Δ29DHODH was purified as follows: cell paste (30 g) was thawed and resuspended in ~100 mL start buffer containing HEPES (50 mM, pH 7.7), NaCl (300 mM), glycerol (10% v/v), and Triton X-100 (0.5% v/v). The cells were lysed by sonication (35% amplitude, 4.0 s pulse, 9.0 s pause, 15 min). The sample was centrifuged at 23,700 g for 45 min (Beckman JA-20 rotor) and the supernatant was passed through a 0.45 μm syringe filter. The sample was loaded onto a 5 mL HisTrap HP column (GE Healthcare Life Sciences). The column was washed with 20 mL each of start buffer containing 5 and 10 mM imidazole. The desired Δ29DHODH protein was eluted by gradually increasing the imidazole concentration to 500 mM. The eluate was collected in several fractions, which were analyzed by Tris-SDS-PAGE (4-20% polyacrylamide gradient). The fractions containing the desired protein were combined and concentrated to a volume of less than 2 mL using an Amicon Ultra-15 centrifugal filter unit with a 10 kDa molecular mass cut off (Millipore). An Amicon filter was used to exchange the concentrated protein into a storage buffer containing HEPES (50 mM, pH 7.7), KCl (300 mM), and glycerol (10% v/v). Following buffer exchange, Δ29DHODH was aliquoted, flash frozen with liquid nitrogen, and stored at −80° C.

In vitro enzyme activity assays with recombinant human Δ29DHODH. Δ29DHODH activity was measured in the presence of teriflunomide, GSK983, and GSK983 analogues using a coupled assay in which the oxidation of dihydroorotic acid (DHO) and subsequent reduction of ubiquinone is stoichiometrically equivalent to the reduction of 2,6-dichlorophenolindophenol (DCPIP). The reduction of DCPIP can be monitored by the loss of absorbance at 610 nm ($\varepsilon$=21,500 $M^{-1}cm^{-1}$). Kinetic constants were calculated from measurements in which Δ29DHODH (10 nM) was either titrated with different concentrations of decylubiquinone ($Q_D$, 10-60 μM) at a fixed concentration of DHO (200 μM) or titrated with different concentrations of DHO (10-60 μM) at a fixed concentration of $Q_D$ (100 μM). Enzymatic assays were conducted at 25° C. in a reaction buffer containing Tris (100 mM, pH 8.0), NaCl (150 mM), DCPIP (60 μM), glycerol (10% v/v), and Triton X-100 (0.1% v/v). The $K_m$ values for Δ29DHODH (15 μM for DHO and 14 μM for $Q_D$) were in good agreement with previously reported values for both the full-size and N-terminally truncated enzyme.

To determine $K_i$ values for inhibitor compounds (teriflunomide, GSK983, 6Br-pF, 6Br-oTol, and GSK984), Δ29DHODH (10 nM) and the appropriate inhibitor compound were added to the previously described reaction buffer. For each inhibitor compound, three reactions were prepared: a control reaction containing no inhibitor and two reactions containing different inhibitor concentrations. Δ29DHODH was incubated with inhibitor compounds at room temperature for 5 min. The indicated concentration of $Q_D$ and DHO (200 μM) were added to the reaction mixtures and absorbance at 610 nm was monitored using a Perki-nElmer Lamda 25 UV-Vis spectrophotometer. For enzyme activity assays, inhibitor compounds were prepared as 1 mM stock solutions in DMSO. A $Q_D$ stock solution (10 mM) was prepared in a buffer containing Tris (100 mM, pH 8.0) and Triton X-100 (1.0% v/v). A DHO stock solution (10 mM)

was prepared in a buffer containing Tris (100 mM, pH 8.0). Concentrated stocks of inhibitor compounds, $Q_D$, and DHO were further diluted as needed with a buffer containing Tris (100 mM, pH 8.0) and Triton X-100 (0.1% v/v) to prepare working stocks. The total volume of the reaction mixture for each assay was 100 µL, and the final concentration of DMSO was 0.01% (v/v).

Cloning, expression, and purification of recombinant human CMPK1. The DNA sequence encoding human CMPK1 (196 amino acid residues) was PCR amplified from a cDNA template (GE Healthcare Dharmacon, catalog number MHS6278-202832682) using the forward primer 5'-AAAAAACATATGAAGCCGCTG GTCGTGTTC-3' and the reverse primer 5'-CACGTCTAAAAACTGTTCCT-TCC GATTCCTAGGTTTTTT-3' and gel-purified.

The PCR-amplified CMPK1-encoding construct was double digested with NdeI and BamHI-HF (New England BioLabs) in CutSmart buffer for 4 h at 37° C. and PCR-purified (Thermo GeneJet PCR Purification Kit). Similarly, vector pET28 was double digested with NdeI and BamHI-HF for 3 h at 37° C. and gel-purified. The CMPK1-encoding insert was ligated into digested pET28 using T4 DNA Ligase (Invitrogen). *E. coli* BL21 (DE3) cells were transformed with a pET28 plasmid containing a CMPK1-encoding insert. Single colony transformants were grown in 5 mL of LB growth medium containing 50 µg/mL kanamycin for 16 h at 37° C. Overnight starter culture (2.5 mL) was added to 1 L of LB growth medium containing 50 µg/mL kanamycin and grown at 37° C. for ~3 h. IPTG (150 µM) was added when A600 was ~0.65. Cells were grown at 18° C. for an additional 16 h. Cells were harvested by centrifugation at 4000 g for 20 min at 4° C. The resulting cell paste was stored at −80° C. prior to protein purification. Recombinant human CMPK1 was purified as follows: cell paste was thawed and resuspended in 50 mL of lysis buffer containing Tris (40 mM, pH 7.5), NaCl (10 mM), NaF (5 mM), and DTT (1 mM). Cells were lysed by sonication and centrifuged at 25,000 g for 1 h. The supernatant was incubated with a slurry of Ni-NTA resin for 1 h at 4° C. and loaded onto a column. The column was washed with 40 mL lysis buffer, then 20 mL each of buffers containing Tris (40 mM, pH 7.5), NaCl (10 mM), DTT (1 mM), and imidazole (10, 40, or 200 mM). The eluate was examined by SDS-PAGE and fractions containing CMPK1 were combined. Isolated CMPK1 was further purified by anion exchange chromatography using an Akta Pure 25 FPLC instrument equipped with a 5 mL Hi Trap Q anion exchange column. Prior to loading onto the anion exchange column, the combined Ni-NTA column eluate containing CMPK1 was diluted in Buffer A containing Tris (50 mM, pH 8.0) and DTT (1 mM) such that the imidazole concentration in the diluted sample was less than 50 mM. The desired protein was eluted from the anion exchange column using a linear gradient from 0 to 95% Buffer B containing Tris (50 mM, pH 8.0), DTT (1 mM), and NaCl (500 mM) over 15 column volumes. Fractions containing the desired protein were spin-concentrated to a volume of less than 1 mL using an Amicon Ultra-15 centrifugal filter unit with a 10 kDa molecular mass cut off (Millipore). An Amicon filter was used to exchange the concentrated CMPK1 into a storage buffer containing Tris (50 mM, pH 7.5) and glycerol (10% v/v). Following buffer exchange, purified CMPK1 was aliquoted, flash frozen with liquid nitrogen, and stored at −80° C.

In vitro enzyme activity assays with recombinant human CMPK1. The activity of recombinant human CMPK1 was measured in the presence of GSK983 using an ATP consumption assay. CMPK1 (10 nM) was added to a reaction buffer containing Tris (50 mM, pH 7.5), $MgCl_2$ (2 mM), DTT (2 mM), ATP (100 µM), CMP (100 µM), and GSK983 (0-10 µM, from a DMSO stock solution). The final concentration of DMSO in all reaction mixtures was 2% (v/v). Enzyme activity assays were conducted at 37° C. The consumption of phosphoryl donor ATP was monitored using a Promega Kinase-Glo Luminescent Kinase Assay kit according to the manufacturer's instructions. We observed no effect of GSK983 on CMPK1 activity in vitro at GSK983 concentrations up to 10 µM.

Pyrimidine metabolite supplementation experiments. For pyrimidine metabolite supplementation experiments in K562 cells, cells were seeded into 24-well plates at a density of 50,000 cells/mL in RPMI growth medium containing the indicated concentration of pyrimidine metabolite and the indicated concentration of DHODH inhibitor (GSK983 or teriflunomide) where applicable. Pyrimidine metabolites were dissolved directly in the growth medium. GSK983 and teriflunomide were delivered from stock solutions in DMSO as described above. Cells were incubated in the presence of exogenous pyrimidines and the indicated DHODH inhibitor at 37° C. for 72 h. Following 72 h treatment, cells were harvested and the density of viable cells was determined by flow cytometry (FSC/SSC) using a BD Accuri C6 Flow Cytometer. For 6 day experiments, cells were plated as described above and diluted to a density of 50,000 cells/mL after 3 days using fresh growth medium containing the appropriate concentrations of GSK983 and pyrimidine metabolites, and cell viability was assessed after an additional 3 days (6 days total) as described above. For pyrimidine metabolite supplementation experiments in HeLa and A549 cells, cells were seeded into 24-well plates at a density of 20,000 cells/well and incubated for 24 h at 37° C. Following 24 h incubation, the growth medium in each well was removed and replaced with fresh DMEM containing the indicated concentration of pyrimidine metabolite and GSK983. Pyrimidine metabolites were dissolved directly in the growth medium. GSK983 was delivered from a stock solution in DMSO as described above. Cells were incubated in the presence of exogenous pyrimidines and GSK983 at 37° C. for an additional 72 h. Following 72 h treatment, cells were harvested and the density of viable cells was determined by flow cytometry (FSC/SSC) using a BD Accuri C6 Flow Cytometer.

Cell cycle analysis based on 5-ethynyl-2'-deoxyuridine (EdU) incorporation. K562 cells were treated with 48 nM GSK983, 1 mM deoxycytidine, both 48 nM GSK983 and 1 mM deoxycytidine, or neither (untreated) for 24 h. Cells were seeded into 6-well plates at a density of 200,000 cells/mL. The final concentration of DMSO in each well was <0.1%. After 24 h incubation with GSK983/deoxycytidine, cells were treated with 10 µM EdU for 2 h. EdU-treated cells were harvested, pelleted (300 g, 5 min), washed (0.5 mL 1×PBS), and resuspended in 70% EtOH (1 mL, 0° C.) with mild vortexing. Cells were fixed in 70% EtOH overnight at 4° C. The following day, fixed cells were pelleted (1900 g, 5 min), washed (0.5 mL 1×PBS) and resuspended in 200 µL of a freshly prepared EdU labeling solution containing Tris-HCl (100 mM, pH 8.5), $CuSO_4$ (1 mM), ascorbic acid (100 mM), and the azide-functionalized fluorophore Azide-fluor 488 (10 µM). Cells were incubated in the EdU labeling solution in the dark at room temperature for 30 min. The cells were pelleted (475 g, 5 min), and the supernatant was removed by vacuum. Cells were washed twice (0.5 mL 1×PBS for each wash). Following the second PBS wash, cells were resuspended in 200 µL of a freshly prepared total DNA content staining solution containing 7-AAD (25

µg/mL in 1×PBS; 7-AAD diluted in PBS from a stock solution in DMSO). Cells were incubated in the total DNA content staining solution in the dark at room temperature for 20 min. Cells were analyzed by flow cytometry using a BD Accuri C6 Flow Cytometer. Azide-fluor 488 fluorescence was detected in FL1. 7-AAD fluorescence was detected in FL3.

In a first control experiment, cells that had not been treated with EdU were subjected to the dual staining protocol described above. In the absence of EdU treatment, we observed no specific labeling of S phase cells. In a second control experiment, cells that had been incubated with 10 µM EdU for 2 h were stained with 7-AAD alone. In the absence of Azide-fluor 488, we observed no specific labeling of S phase cells.

Construction of pDENV-Luc infectious clone. The design of the DENV reporter used here was based on the previously described mDVR construct. Briefly, the viral 5'UTR was followed by a duplication of the first 104 nucleotides of the C coding region, which contains cis-acting elements required for replication (CAE). The CAE was fused to the Renilla luciferase coding region followed by the complete DENV open reading frame (ORF). Between the Renilla luciferase and DENV structural protein coding sequences, a foot and mouth disease virus (FMDV) 2A sequence was introduced to provide co-translational cleavage and luciferase release. The construct was based on pD2/IC-30P, which contains a full-length infectious clone encoding dengue virus serotype 2 strain 16681. We introduced an Envelope Q399H mutation to enhance viral infection in mammalian cells using a QuikChange Site-Directed Mutagenesis kit (Agilent Technologies) (primers: 5'-GGAAGTTC TATCGGCCACATGTTTGAGACAAC-3' and 5'-GTT-GTCTCAAACATGTGGCCGAT AGAACTTCC-3). We gene-synthesized a fragment containing the T7 polymerase promoter sequence followed by the first 102 nucleotides of the C coding region in frame with the Renilla luciferase and FMDV 2A sequences. This fragment was PCR-amplified, introducing a Sac! site at the 5' end and a NheI site (present in the FMDV 2A sequence) at the 3' end using primers: 5'-CGAAATTCGAGCTCACGCG-3' and 5'-TCCT-GCTAGCTTGAGCAAATCAAAGTTC-3'. To create an in-frame fusion of FMDV 2A with the DENV-ORF, a second DNA fragment was PCR-amplified from a pD2/IC-30P template (primers: 5'-TCAAG CTAGCAGGAGACGTT-GAGTCCAACCC CGGGCCCATGAATAACCAACG-GAAAAAGGCG-3' and 5'-GGAAGAGCATGCAG TCG-GAAATG-3'), thus introducing 5' NheI and 3' SphI restriction sites. The two fragments were cut with the respective restriction enzymes and ligated into pD2/IC-30P (previously digested with SacI and SphI) to create pDENV-Luc. DENV-Luc virus was produced via in-vitro transcription of pDENV-Luc and transfection into BHK cells as described previously$_{48}$.

DENV antiviral assays. For DENV inhibition assays (FIG. 3c), human A549 cells were seeded into 24-well plates at a density of 20,000 cells/well and incubated for 24 h. The cells were treated with DMEM containing GSK983 at the indicated concentrations for 4 h at 37° C. Growth medium containing GSK983 was removed and cells were incubated for 1 h with DENVLuc (no GSK983) at 37° C. Following DENV-Luc incubation, cells were washed with 1×PBS and treated with fresh DMEM containing GSK983 at the indicated concentrations. Cells were incubated at 37° C. for an additional 72 h. Where specified, the growth medium was supplemented with 1 mM uridine or 1 mM deoxycytidine. DENV-Luc replication was monitored by the production of Renilla luciferase, which was measured using the Renilla-Glo Luciferase Assay System (Promega) according to the specifications of the manufacturer. For the accompanying cell viability assay (FIG. 3d), A549 cells were seeded into 24-well plates at a density of 20,000 cells/well incubated for 24 h at 37° C. Cells were then treated with GSK983 at the indicated concentration for 72 h. Where specified, the growth medium was supplemented with 1 mM uridine or 1 mM deoxycytidine. Following 72 h treatment, cells were harvested and the density of viable cells was determined by flow cytometry (FSC/SSC) using a BD Accuri C6 Flow Cytometer.

VEEV antiviral assays. A plasmid encoding the recombinant VEEV-GFP genome (vaccine strain TC-83) was kindly provided by Professor Frolov (University of Alabama at Birmingham). This plasmid was used to generate replication competent VEEV (capable of expressing GFP upon infection) in Huh7 cells. For the VEEV inhibition assay (FIG. 9e), human A549 cells were seeded into 96-well plates at a density of 10,000 cells per well and incubated for 24 h at 37° C. in DMEM containing GSK983 only (at the indicated concentrations), or supplemented with 1 mM uridine, 1 mM deoxycytidine, 1 mM dihydroorotic acid, or 1 mM orotic acid. Following this incubation, VEEV-GFP (at an MOI of 20 plaque forming units/cell) was added to the media and cells were further incubated for 16 hours at 37° C. GFP expression was then used to measure VEEV-GFP replication in the infected samples using flow cytometry. All flow cytometry was performed using a BD LSR Fortessa™ cell analyzer (BD, Franklin Lakes, N.J., USA) and data was analyzed and assembled using FlowJo software (TreeStar Inc, Ashland, Oreg., USA).

Synthesis and characterization of GSK983 and analogues. General Methods. All deuterated solvents for NMR spectroscopy were obtained from Cambridge Isotope Laboratories. All reagents obtained from commercial sources were used as received. Chiral HPLC was performed using a Thermo Separation Products Spectra Series P-100 and UV100 (254 nm) with a Chiralcel column (IA) eluting with heptane/isopropanol [90:10]. Mass spectrometry was performed as follows: samples were dissolved in methanol and loaded onto a Gemini-NX C18 column (Phenomenex, 5 µm, 2×100 mm) connected to an Agilent 1260 HPLC. Samples were eluted using a 28 min linear gradient of acetonitrile from 3-95%, and then injected into a 6520 Accurate-Mass QTOF mass spectrometer. Specific rotation was determined using a Jasco P-2000 Polarimeter. Synthetic procedures are based on the work of Boggs et al. and Gudmundsson et al. (GlaxoSmithKline, Research Triangle Park, N.C., USA)

1 (E)-2-(2-(4-Chlorophenyl)hydrazono)cyclohexanone (1). 4-chlorophenylhydrazine hydrochloride (1.60 g, 8.92 mmol) was added portion-wise to a stirred solution of 1,2-cyclohexane dione (1.00 g, 8.92 mmol) in water (13.4 mL) at room temperature. The reaction mixture turned bright orange within 5 minutes. The reaction was stirred for 16 h at room temperature, whereupon the heterogeneous reaction mixture was filtered. The filtered material was washed with water and air dried to afford the desired product as a reddish-orange solid (1.51 g, 72%). 1 was used in the subsequent step without further purification. $_1$H NMR (CDCl$_3$, 300 MHz) δ 1.85 (m, 4H), 2.51 (m, 2H), 2.69 (m, 2H), 7.17 (d, J=9.0 Hz, 2H), 7.25 (d, J=9.0 Hz, 2H).

1

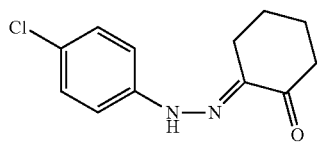

2  6-Chloro-2,3,4,9-tetrahydro-1H-carbazol-1-one (2). HCl (12 N, 4 mL) was added to a stirred solution of 1 (4.62 g, 19.5 mmol) in glacial acetic acid (16 mL). The color of the reaction mixture immediately changed from reddish-orange to dark brown. The reaction mixture was refluxed for 20 min. Ice water was added and a dark brown precipitate formed. The heterogeneous reaction mixture was cooled to 0° C. and vacuum filtered. The filtered material was washed twice with ice water to afford the desired product as a dark brown solid which was dried under high vacuum overnight (2.63 g, 62%). Vacuum dried 2 was used in the subsequent step without further purification. HRMS (ESI): obsd m/z=220.0621, calcd 220.0524 [(M+H)+, M=$C_{12}H_{10}ClNO$]. $_1$H NMR (CD$_3$OD, 300 MHz) δ 2.24 (m, 2H), 2.62 (t, J=6.0 Hz, 2H), 2.98 (t, J=6.0 Hz, 2H), 7.27 (dd, J=9.0, 2.1 Hz, 1H), 7.38 (d, J=9.0 Hz, 1H), 7.65 (d, J=2.1 Hz, 1H).

2

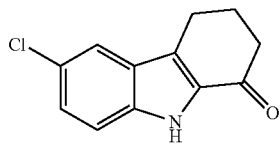

(R)-6-Chloro-N—[(R)-1-(4-methoxyphenyl)ethyl]-2,3,4,9-tetrahydro-1H-carbazol-1-amine hydrochloride (4). 2 (2.63 g, 12.0 mmol), (R)-1-(4-methoxyphenyl)ethylamine (1.81 g, 12.0 mmol), and p-toluenesulfonic acid (160 mg, 0.84 mmol) were added under argon to a two-neck round bottom flask equipped with a reflux condenser and a Dean-Stark distillation apparatus containing 4 Å molecular sieves. All Glassware and molecular sieves had been oven-dried overnight. Anhydrous toluene (25 mL) was added to the flask via syringe. The resulting dark brown solution was refluxed for 16 h. The reaction mixture was cooled to room temperature and concentrated via rotary evaporator to a dark brown oil. The 1H NMR spectrum of the crude product indicated the presence of the imine 3. Crude 3 was immediately dissolved in absolute EtOH (32 mL) and cooled to 0° C. NaBH$_4$ (272 mg, 7.20 mmol) was added portion-wise. The reaction mixture was stirred at 0° C. for 16 h and concentrated via rotary evaporator. The crude product was dissolved in EtOAc and washed with saturated aqueous NaHCO$_3$. The aqueous phase was discarded and the organic fraction was washed again with water and saturated aqueous brine, dried (Na$_2$SO$_4$), and concentrated via rotary evaporator. The crude product was dissolved in EtOAc/MeOH (21 mL, [5:2]). 4 N HCl in 1,4-dioxane (4.5 mL) was added dropwise under argon causing a pale brown solid to precipitate. The reaction mixture was stirred for 1 h at room temperature and filtered. The filtered material was washed with absolute EtOH to afford the desired tetradehydrocarbazolamine HCl salt 4 as a pale brown solid (2.00 g, 43% from 2). The $_1$H NMR spectrum of 4 appeared to show the presence of a single diastereomer and minor unidentified impurities. 4 was used in the subsequent step without further purification. $_1$H NMR (DMSO-d$_6$, 300 MHz) δ 1.67 (d, J=6.9 Hz, 3H), 1.81 (m, 1H), 1.98 (m, 2H), 2.09 (m, 1H), 2.64 (m, 2H), 3.77 (s, 3H), 4.56 (m, 1H), 4.71 (m, 1H), 7.01 (d, J=8.7 Hz, 2H), 7.14 (dd, J=8.4, 1.8 Hz, 1H), 7.43 (d, J=8.4 Hz, 1H), 7.53 (d, J=1.8 Hz, 1H), 7.72 (d, J=8.4 Hz, 2H), 9.27 (br, 1H), 9.87 (br, 1H), 11.64 (s, 1H).

4

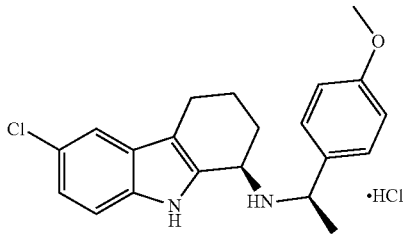

(R)—N-(6-Chloro-2,3,4,9-tetrahydro-1H-carbazol-1-yl) picolinamide (GSK983). BCl$_3$ (1 M solution in hexanes) (2.55 mL, 2.55 mmol) was added dropwise to a stirred heterogeneous suspension of 4 (392 mg, 1.00 mmol) in anhydrous CH2Cl2 (2.0 mL) in an oven-dried flask under argon. The reaction mixture changed from a pale brown suspension to a dark purple homogeneous solution upon addition of BCl$_3$. The reaction mixture was stirred for 3 h at room temperature under argon. The flask was removed from continuous argon to prevent solvent loss and stirred at 0° C. for 16 h. KOH (4.00 g, 20 wt % in water) was added slowly dropwise. The solution changed from dark purple to golden brown in color. The biphasic mixture was stirred vigorously for 20 min and water was added. The phases were allowed to separate. The aqueous phase was discarded and the organic layer was washed with saturated aqueous brine, dried (Na$_2$SO$_4$), and concentrated via rotary evaporator to a dark brown oil. The crude material was dissolved in anhydrous Et$_2$O (8.0 mL), and 4 N HCl in 1,4-dioxane (1.0 mL) was added under argon. A brown solid immediately precipitated from solution. The mixture was filtered. The filtered material was washed with anhydrous Et$_2$O and dried under high vacuum to afford a brown solid (200 mg). The $_1$H NMR spectrum of the crude product indicated the presence of the 1° amine HCl salt 5 and a small quantity of unreacted 4. Vacuum-dried crude 5 was immediately used in the next step. Neat Et$_3$N (627 μL, 4.68 mmol) was added to a stirring mixture containing crude 5 (200 mg), hydroxybenzotriazole hydrate (HOBt hydrate) (127 mg, 0.94 mmol), 1-ethyl-3-(3-dimethylaminopropyl)carbodiimide hydrochloride (EDC.HCl) (145 mg, 0.94 mmol), and picolinic acid (116 mg, 0.94 mmol) in anhydrous CH$_2$Cl$_2$ under argon. The reaction mixture rapidly changed from a heterogeneous suspension to an amber colored homogeneous solution upon addition of Et$_3$N. The reaction mixture was stirred under argon for 2 h at room temperature. The flask was removed from continuous argon to prevent solvent loss and stirred for an additional 14 h at room temperature. Water was added. The phases were allowed to separate and the aqueous layer was discarded. The organic fraction was washed with saturated aqueous brine and saturated aqueous NaHCO$_3$, dried (Na$_2$SO$_4$), and concentrated via rotary evaporator. The crude product was purified by column chromatography (silica, CH$_2$Cl$_2$) to afford the desired compound as an off-white solid in high purity (106 mg, 33% from 4). Enantiomeric ratio >99.5:0.5. [α]$_D$=+177 (c 1.12, CH2Cl2). HRMS (ESI): obsd m/z=326.1048, calcd 326.1055 [(M+H)+, M=$C_{18}H_{16}ClN_3O$]. $_1$H NMR (DMSO-d$_6$, 300 MHz) δ 1.82

(m, 1H), 2.03 (m, 3H), 2.63 (m, 2H), 5.33 (m, 1H), 7.01 (dd, J=8.7, 2.1 Hz, 1H), 7.26 (d, J=8.7 Hz, 1H), 7.43 (d, J=2.1 Hz, 1H), 7.61 (m, 1H), 8.03 (m, 1H), 8.11 (d, J=7.8 Hz, 1H), 8.60 (d, J=4.5 Hz, 1H), 8.81 (d, J=8.7 Hz, 1H), 10.95 (br, 1H).

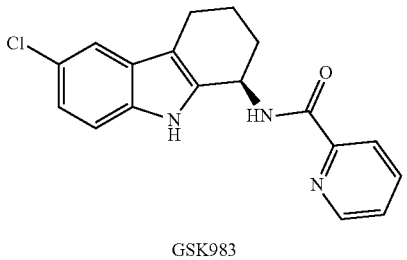 [SMILES: O=C(N[C@@H]1CCCc2c1[nH]c1ccc(Cl)cc21)c1ccccn1]

GSK983

(S)-6-Chloro-N—((S)-1-(4-methoxyphenyl)ethyl)-2,3,4,9-tetrahydro-1H-carbazol-1-amine hydrochloride (6). 6 was synthesized from the carbazolone 2 according to the procedure described for the synthesis of 4. (S)-1-(4-Methoxyphenyl)ethylamine was used to direct diastereoselective reductive amination of carbazolone 2 (27). The product was isolated as a beige solid (1.16 g, 40% from carbazolone 2). HRMS (ESI): obsd m/z=355.1500, calcd 355.1572 [(M+H)$_+$, M=$C_{21}H_{123}ClN_2O$]. $_1$H NMR (DMSO-d$_6$, 300 MHz) δ 1.61 (d, J=6.0 Hz, 3H), 1.82 (m, 1H), 1.95 (m, 3H), 2.68 (m, 2H), 3.77 (s, 3H), 4.41 (m, 1H), 4.68 (m, 1H), 7.02 (d, J=9.0 Hz, 2H), 7.15 (dd, J=9.0, 3.0 Hz, 1H), 7.45 (d, J=9.0 Hz, 1H), 7.53 (d, J=3.0 Hz, 1H), 7.65 (d, J=9.0 Hz, 2H), 9.05 (m, 1H), 9.50 (m, 1H), 11.41 (s, 1H).

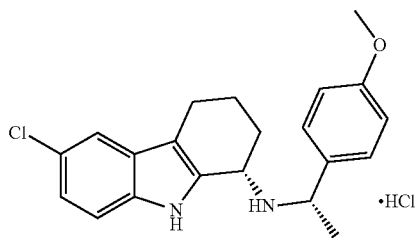

6

GSK984 N (S)—N-(6-Chloro-2,3,4,9-tetrahydro-1H-carbazol-1-yl)picolinamide (GSK984). GSK984 was synthesized from the tetradehydrocarbazolamine HCl salt 6 according to the procedure described for the synthesis of GSK983. Following aqueous workup, the crude product was purified by column chromatography (silica, CH$_2$Cl$_2$) to afford the desired compound as an off-white solid with minimal impurities (76.6 mg, 28% from 6). Enantiomeric ratio=99:1. HRMS (ESI): obsd m/z=326.1045, calcd 326.1055 [(M+H)$_+$, M=$C_{18}H_{16}ClN_3O$]. $_1$H NMR (DMSO-d$_6$, 300 MHz) δ 1.82 (m, 1H), 2.00 (m, 3H), 2.64 (m, 2H), 5.34 (m, 1H), 7.01 (dd, J=9.0, 3.0 Hz, 1H), 7.26 (d, J=9.0 Hz, 1H), 7.43 (d, J=3.0 Hz, 1H), 7.61 (m, 1H), 8.02 (m, 1H), 8.12 (d, J=9.0 Hz, 1H), 8.61 (d, J=6.0 Hz, 1H), 8.80 (d, J=9.0 Hz, 1H), 10.95 (s, 1H).

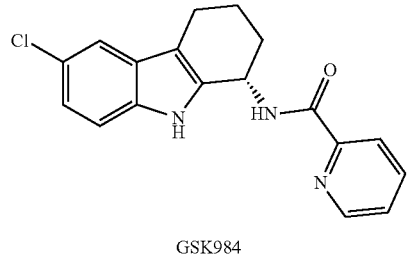 [SMILES: O=C(N[C@H]1CCCc2c1[nH]c1ccc(Cl)cc21)c1ccccn1]

GSK984

(E)-2-(2-(4-Bromophenyl)hydrazono)cyclohexanone (10). 4-bromophenylhydrazine hydrochloride (8.00 g, 35.7 mmol) was added portion-wise to a stirred solution of 1,2-cyclohexane dione (4.00 g, 35.7 mmol) in water (57.2 mL) at room temperature. The reaction mixture turned bright orange within 5 minutes. The reaction was stirred for 16 h at room temperature, whereupon the heterogeneous reaction mixture was filtered. The filtered material was washed with water and dried overnight under high vacuum to afford the desired product as a bright orange solid in almost quantitative yield (9.73 g, 97%). 1H NMR (CDCl$_3$, 300 MHz) δ 1.85 (m, 4H), 2.51 (m, 2H), 2.69 (m, 2H), 7.11 (d, J=9.0 Hz, 2H), 7.38 (d, J=9.0 Hz, 2H).

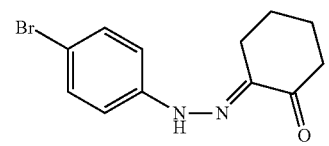

10

6-Bromo-2,3,4,9-tetrahydro-1H-carbazol-1-one (11). Carbazolone 11 was synthesized from 10 according to the procedure described for the synthesis of 2. The desired product was isolated as a dark brown solid (3.64 g, 76%). HRMS (ESI): obsd m/z=264.0053, calcd 264.0019 [(M+H)$_+$, M=$C_{12}H_{10}BrNO$]. $_1$H NMR (CDCl$_3$, 300 MHz) δ 2.25 (m, 2H), 2.63 (t, J=6.0 Hz, 2H), 2.99 (t, J=6.0 Hz, 2H), 7.34 (d, J=8.7 Hz, 1H), 7.40 (dd, J=8.7, 1.8 Hz, 1H), 7.82 (d, J=1.8 Hz, 1H).

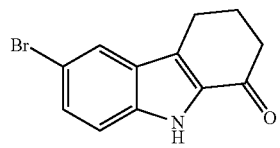

11

(R)-6-Bromo-N—((R)-1-(4-methoxyphenyl)ethyl)-2,3,4,9-tetrahydro-1H-carbazol-1-amine hydrochloride (13). 13 was synthesized from the carbazolone 11 according to the procedure described for the synthesis of 4. The desired product was isolated as a light brown solid (3.26 g, 54% from carbazolone 11). HRMS (ESI): obsd m/z=399.0894, calcd 399.1067 [(M+H)$_+$, M=$C_{21}H_{23}BrN_2O$]. $_1$H NMR (DMSO-d$_6$, 300 MHz) δ 1.66 (d, J=6.6 Hz, 3H), 1.77 (m, 1H), 1.96 (m, 2H), 2.08 (m, 1H), 2.62 (m, 2H), 3.75 (s, 3H), 4.56 (m, 1H), 4.69 (m, 1H), 6.98 (d, J=9.0 Hz, 2H), 7.23 (dd, J=8.7, 2.1 Hz, 1H), 7.36 (d, J=9.0 Hz, 1H), 7.65 (d, J=1.5 Hz, 1H), 7.71 (d, J=8.7 Hz, 2H), 9.27 (m, 1H), 9.89 (m, 1H), 11.79 (s, 1H).

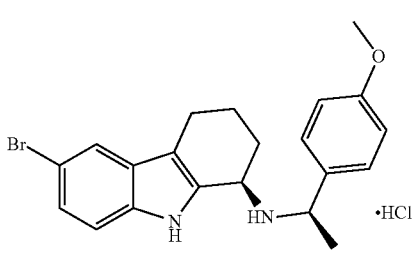

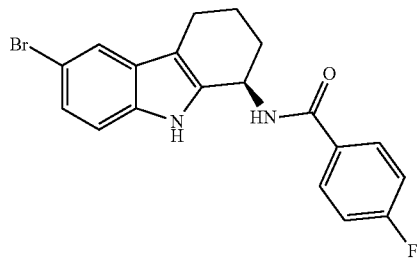

6Br-pF (R)—N-(6-Bromo-2,3,4,9-tetrahydro-1H-carbazol-1-yl)-2-methylbenzamide (6BroTol). 6Br-oTol was synthesized from the tetradehydrocarbazolamine HCl salt 13 according to the procedure described for the synthesis of GSK983. Following aqueous workup, the crude product was purified by column chromatography (silica, CH2C12) to afford the desired product as an off-white solid in high purity (110 mg, 35% from 13). Enantiomeric ratio=98:2. HRMS (ESI): obsd m/z=383.0548, calcd 383.0754 [(M+H)+, M=$C_{20}H_{19}BrN_2O$]. $_1$H NMR (DMSO-$d_6$, 400 MHz) δ 1.83 (m, 2H), 2.01 (m, 2H), 2.37 (s, 3H), 2.60 (m, 2H), 5.29 (m, 1H), 7.13 (dd, J=8.4, 2.0 Hz, 1H), 7.21 (d, J=7.2 Hz, 2H), 7.28 (d, J=8.4 Hz, 2H), 7.42 (d, J=8.4 Hz, 1H), 7.55 (d, J=2.0 Hz, 1H), 8.67 (d, J=8.4 Hz, 1H), 10.98 (s, 1H).

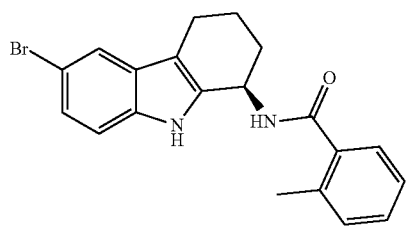

6Br-oTol (R)—N-(6-Bromo-2,3,4,9-tetrahydro-1H-carbazol-1-yl)-4-fluorobenzamide (6Br-pF). 6Br-pF was synthesized from the tetradehydrocarbazolamine HCl salt 13 according to the procedure described for the synthesis of GSK983. The $_1$H NMR spectrum of the crude product indicated the presence of 6Br-pF. An attempt to purify the crude product by column chromatography (silica, $CH_2Cl_2$) was unsuccessful. 6Br-pF was poorly soluble in $CH_2Cl_2$ which likely contributed to difficulties with chromatographic purification. 6Br-pF was suspended in anhydrous $Et_2O$. The resulting milky suspension was filtered via vacuum filtration to afford the desired compound as a white solid in high purity (46 mg, 14% from 13; low yield attributed to product loss during attempted chromatographic separation). Attempts to determine the enantiomeric ratio of 6Br-pF by chiral HPLC using the racemate 17 as a standard failed owing to the poor solubility of the compound. Given that 6Br-pF was synthesized from the same batch of 13 as 6Br-oTol, the enantiomeric ratio of 6Br-pF is estimated to be ~98:2. HRMS (ESI): obsd m/z=387.0493, calcd 387.0503 [(M+H)+, M=$C_{19}H_{16}BrFN_2O$]. $_1$H NMR (DMSO-$d_6$, 400 MHz) δ 1.82 (m, 2H), 2.04 (m, 2H), 2.63 (m, 2H), 5.33 (m, 1H), 7.12 (dd, J=8.4, 2.0 Hz, 1H), 7.27 (m, 3H), 7.56 (d, J=2.0 Hz, 1H), 8.00 (m, 2H), 8.88 (d, J=8.0 Hz, 1H), 11.00 (s, 1H).

Example 2

Development of a Combinatorial Strategy to Inhibit Pyrimidine Biosynthesis and Nucleotide Salvage for Broad Spectrum Antiviral Therapy Developing efficacious therapies for pathogenic viral infections is one of the biggest challenges in public health. Viruses such as West Nile (WNV), Dengue (DV) and Ebola, which contribute to over 100 million viral infections yearly, pose a significant worldwide health threat, with few therapeutic options and no currently approved prophylactic options. Insights into the molecular mechanisms of viral life cycles have led to the emergence of antiviral therapeutics that specifically target viral components. However, given the rapid rate of virus evolution, the potential for developing drug-resistance is high when directing antivirals against viral proteins. This is well demonstrated by drugs such as the adamantanes (amantadine and rimantadine), which act against influenza A, but have been deemed poor treatments against Influenza infections due to a marked increase in adamantine-resistant isolates. Targeting a cellular protein essential for viral infection offers the opportunity to create antiviral compounds against a wide range of viruses, with a reduced likelihood of generating virus resistance, and the potential opportunity to use such drugs as frontline therapies for rapidly emerging outbreaks. Efforts to develop host-targeted antiviral therapies are limited by toxicity (especially if the protein or pathway used is crucial for cell survival) and in vivo efficacy. These risks are mitigated if the virus utilizes the host target in a markedly different manner from the obligate cellular process or targets a non-essential biological pathway.

One approach to achieve broad-spectrum antiviral activity is to target host processes required for viral replication such as pyrimidine biosynthesis. Cells infected with viruses must increase de novo pyrimidine biosynthesis to provide pyrimidine nucleotides for viral replication. Inhibition of the key host pyrimidine biosynthesis enzyme DHODH prevents de novo pyrimidine synthesis, but salvage pathways which allow cells to absorb pyrimidine building blocks from their environment can compensate to allow viral replication. Therefore, the combined inhibition of a rate-limiting enzyme in de novo pyrimidine synthesis with an inhibitor of pyrimidine salvage should provide more effective antiviral activity.

In our study described above, we demonstrated an improved drug target identification platform that utilized parallel genome-wide high-coverage shRNA and CRISPR-Cas9 screens to discover the host cell target and mechanism of action of GSK983, a potent broad spectrum antiviral lead compound with unexplained cytotoxicity. We reasoned that the spectrum of shRNA-mediated knockdown efficiency should facilitate identification of essential genes that modulate GSK983 toxicity, while CRISPR-Cas9 mediated knockout should enable detection of non-essential genes that require full deletion to produce an observable phenotype. In addition, shRNA-mediated knockdown of a selected gene is expected to phenocopy pharmacological inhibition of the encoded protein. Therefore, GSK983 should be more toxic to cells expressing an shRNA against a gene encoding a protein target of the drug. Using this approach, we demonstrated that GSK983 blocks both cell proliferation and dengue virus (DENV and VEEV) replication by inhibiting the de novo pyrimidine biosynthesis enzyme DHODH. Pharmacological inhibition of DHODH depletes cellular pyrimidine (deoxy)ribonucleotide pools required for both cell growth and viral replication.

Guided by mechanistic insights from our genomic screens, we also found that exogenous deoxycytidine (dC) markedly reduces GSK983 cytotoxicity but not anti-DENV activity, providing an attractive novel strategy to improve the therapeutic window of DHODH inhibitors against DENY, VEEV, and other RNA viruses. Our data indicate that cellular salvage of exogenous dC enables continued cellular DNA synthesis despite DHODH inhibition, thereby reducing cytotoxicity. However, dC salvage does not sustain RNA virus replication because ribonucleotides cannot be biosynthesized from their 2'-deoxy analogues.

Uridine nucleotide transporters and the pyrimidine salvage enzyme uridine-cytidine kinase (UCK2) are necessary for uridine salvage, a process which may limit the antiviral activity of DHODH inhibitors in vivo by replenishing cellular ribonucleotide pools. Therefore, inhibition of these targets should allow efficient suppression cellular ribonucleotide levels. In preliminary experiments, we have shown that the FDA approved nucleotide transporter inhibitor dipyridamole or knockdown of UCK2 can decrease uridine salvage by K562 and A549 cells. Here, we explored an innovative antiviral strategy in which a DHODH inhibitors (GSK983 or FDA approved teriflunomide) can be used in combination with inhibitors of uridine salvage such as dipyridamole or an inhibitor of UCK2.

Results

When placed in the context of literature indicating that the serum concentration of uridine in mammals is tightly controlled under virtually all physiological conditions, our data suggested that the in vivo antiviral efficacy of GSK983 (or other DHODH inhibitors such as FDA-approved teriflunomide) could be significantly improved in combination with an inhibitor of uridine salvage. Two targets were of particular interest to us—nucleoside transporters, which imports exogenous uridine (as well as other nucleosides) into cells; and uridine-cytidine kinase (UCK2), which converts the imported uridine into UMP (as well as cytidine into CMP).

Figure 11A:
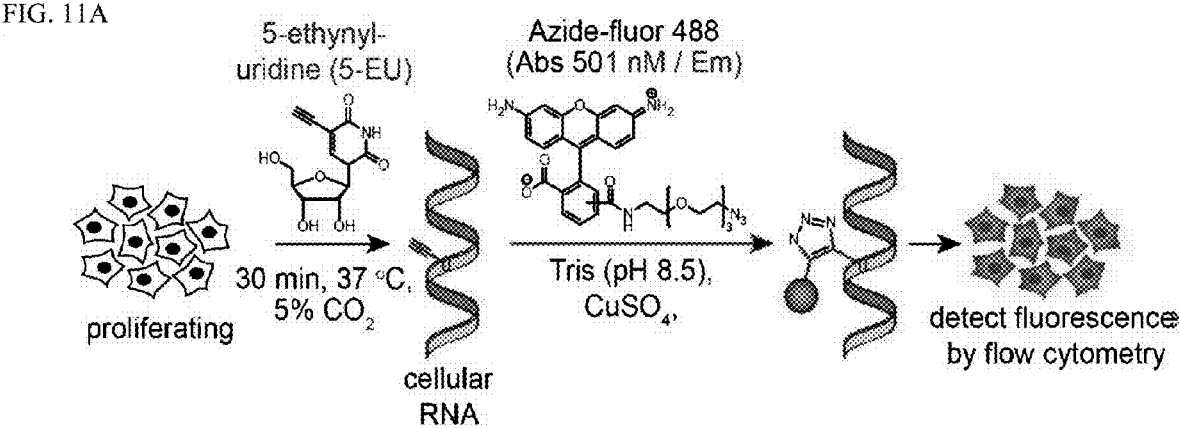
FIG. 11A-11C.
Figure 11B:
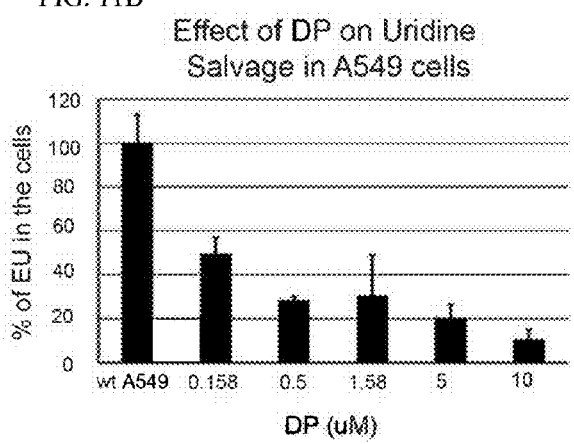

Based on a literature review, we identified dipyridamole, an FDA-approved cardiovascular drug, as a candidate nucleoside transport inhibitor. Notwithstanding its off-target activities (dipyridamole is known to block nucleoside uptake as well as certain cyclic nucleotide phosphodiesterases), we have verified that dipyridamole blocks uridine uptake by cultured K562 and A549 cells at clinically suitable concentrations (FIG. 11b). Because no pharmacologically useful UCK2 inhibitor is known in the literature, we chose to validate the suitability of this target using a genetic method. Two UCK2 shRNA-expressing K562 derivatives were constructed; both showed reduced uridine uptake (FIG. 11b).

Figure 12A:
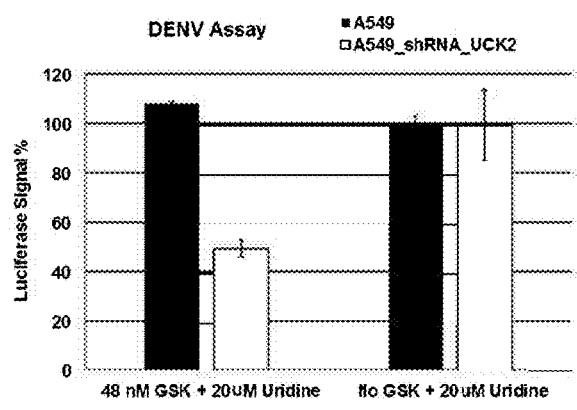
FIG. 12A-12B.
Figure 12B:
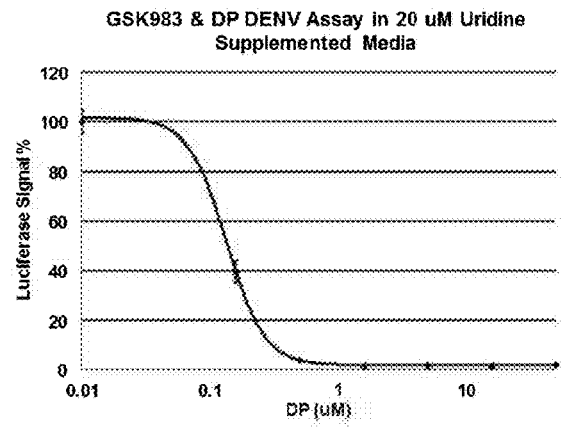

The antiviral activity of a combination of GSK983 and a uridine salvage inhibition mechanism was investigated in dengue virus (DENV)-infected cells cultured in the presence of exogenous uridine. (Our earlier studies had shown that 20 µM uridine is adequate to neutralize the antiviral activity of GSK983 against DENV in vitro.) Accordingly, a luciferase-expressing strain of DENV was infected in either A549 cells or one of the UCK2 shRNA derivatives shown in FIG. 11b. As seen in FIG. 12a, GSK983 inhibited viral replication in the latter cell-line, but not the former. Similarly dipyridamole (DP) shows dose-dependent inhibition of DENV in the presence of 48 nM GSK983 (FIG. 12b).

Figure 13:
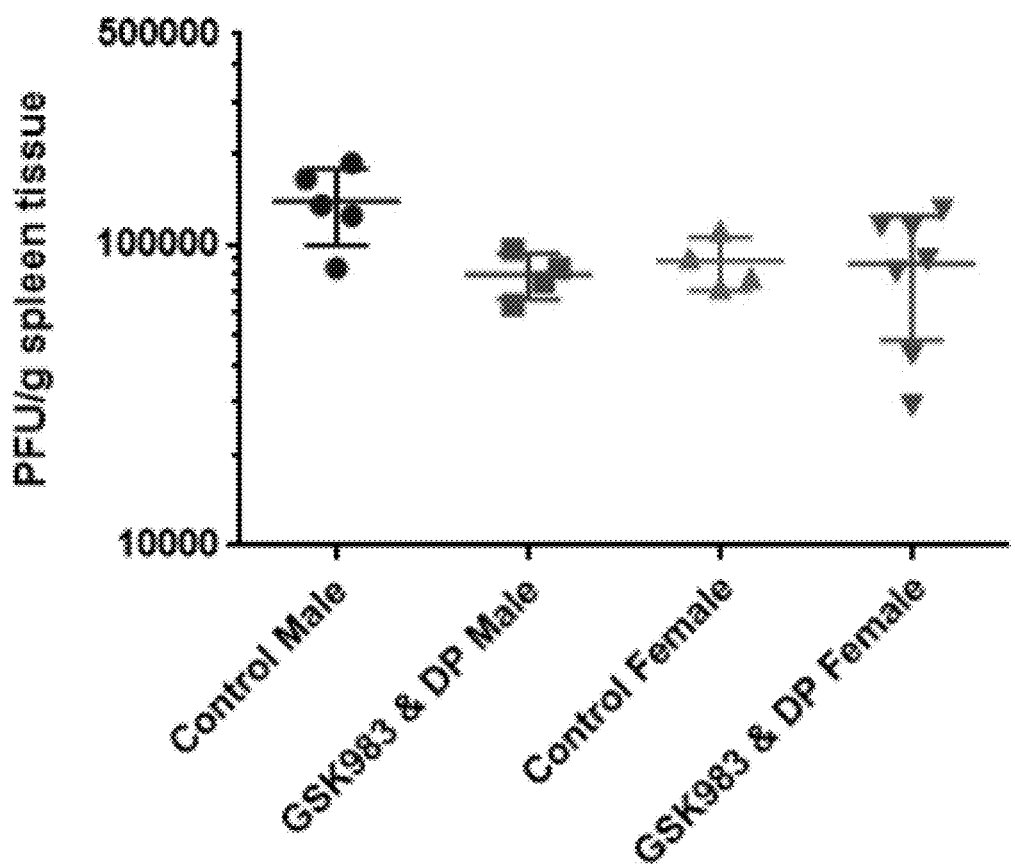
FIG. 13. AG129B6 mice (129/Sv mice lacking alpha/beta interferon [IFN-α] and IFN-β receptors) were retro-orbitally infected with $4\times10^6$ PFU/mouse DENV and dosed with 10 mg/kg GSK983 and 50 mg/kg DP b.i.d via intraperitoneal injection of individual drugs (i.p). The analysis of viral titers from spleens harvested at 4 days post-infection is shown for male and female mice.

These results demonstrate validity of the above hypothesis, and were used for the basis for further studies including in vivo experiments with DENV mouse model. AG129B6 mice (129/Sv mice lacking alpha/beta interferon [IFN-α] and IFN-β receptors) were retro-orbitally infected with $4\times10^6$ PFU/mouse and dosed with 10 mg/kg GSK983 and 50 mg/kg DP b.i.d via intraperitoneal injection of individual drugs (i.p). The analysis of viral titers from spleens harvested at 4 days post-infection suggested that the combination therapy with GSK983 and DP was effective in male mice resulting in about 2-3 folds of decrease in spleen viral titers (FIG. 13). However, dengue spleen titers for the female mice showed no difference between treated and untreated animals (FIG. 13). In conclusion, our in vivo experiments using dengue model mouse further supports our hypothesis that combination therapy inhibiting de novo and salvage pathways of pyrimidine synthesis can be successfully applied to animal models.

Inhibition of the de novo pyrimidine synthesis pathway in combination with inhibition of the salvage pathway can also be effective for the treatment of many cancer types with adjusted dosing regiments for cancer therapy. Previously, scientists investigated this hypothesis using an inhibitor of aspartate transcarbamoylase (ATCase), a portion of a multifunctional enzyme (CAD), by a compound called N-phosphonacetyl-L-aspartate (PALA) in combination with DP. The phase 2 trials for this combination therapy resulted in inconclusive results showing variation from patient to patient. We think that these studies might have failed due to several reasons and can be improved as explained below. Firstly, these studies might have failed because of inefficient inhibition of the de novo pyrimidine synthesis as the CAD enzyme is not the rate limiting step on this pathway. By employing inhibitors for DHODH enzyme, the rate limiting step in the de novo pyrimidine synthesis, one can overcome this problem. Secondly, the study was performed only on solid tumors. Recently, an inhibitor of DHODH called brequinar was shown to be effective towards chronic myelogenous leukemia (CML) in mouse models. A combination therapy with a DHODH inhibitor (brequinar, GSK983, or teriflunomide) with a uridine salvage inhibitor should be more effective in combatting this disease. It also should be noted that the worst side effect seen in the phase 2 clinical studies for combination of PALA and DP was minor headache, and diarrhea in human suggesting low toxicity profile for this type of treatment.

Figure 14:
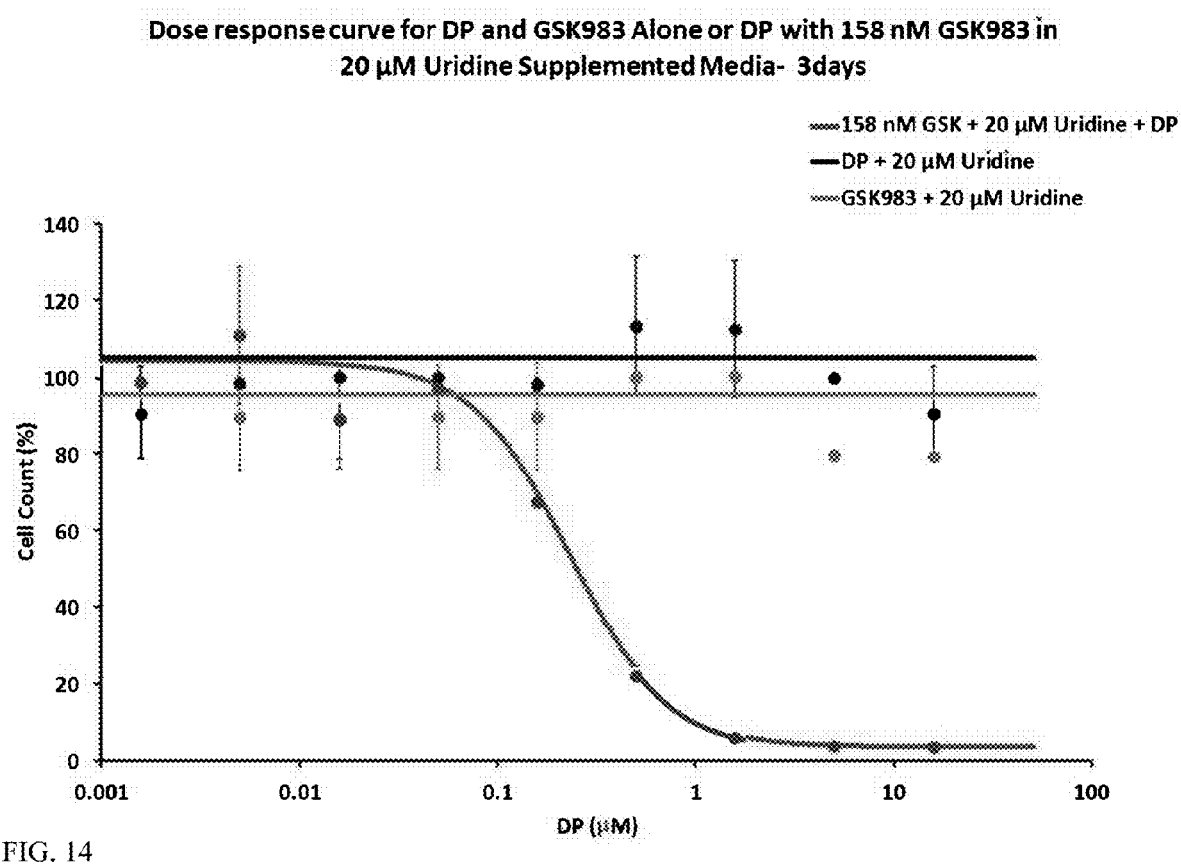
FIG. 14. A549 viable cell counts (%) for DP or GSK983 alone or 158 nM GSK893 with different concentrations of DP in 20 µM uridine supplemented media ($IC_{50}$(DP) of 230 nM).
Figure 15:
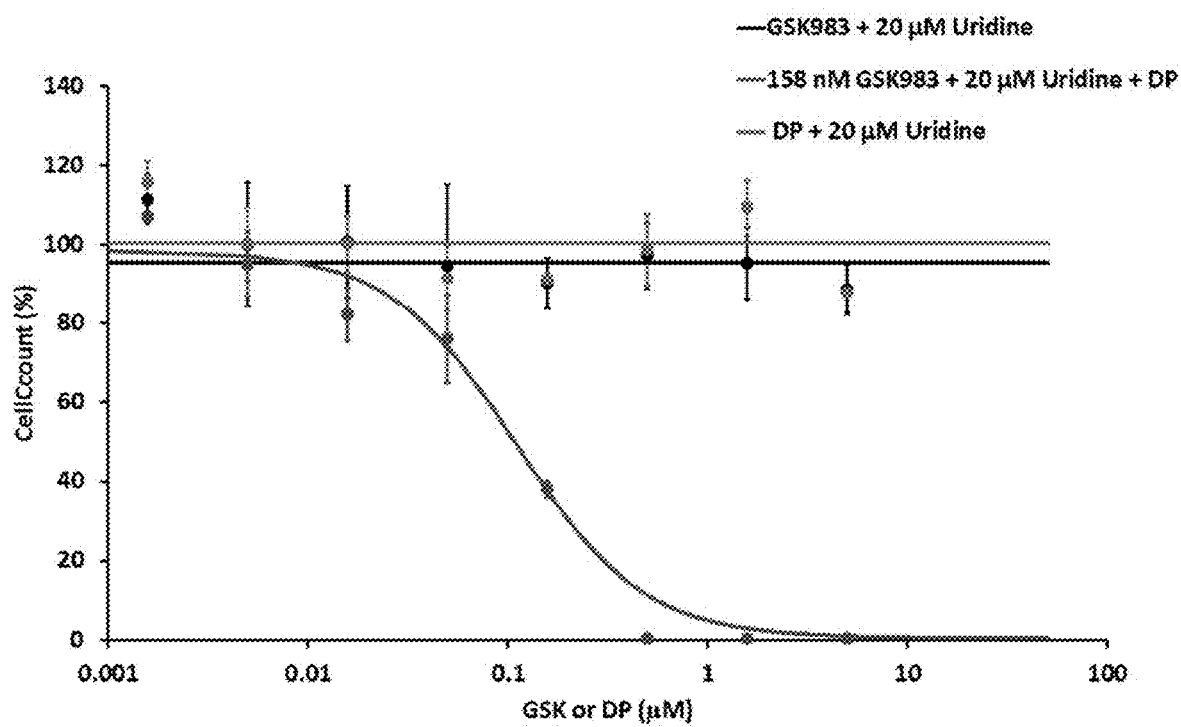
FIG. 15. K562 cell count (%) for DP alone or 50 nM GSK893 with different concentrations of DP in 20 µM uridine supplemented media ($IC_{50}$(DP) of 110 nM).

In order to support the anticancer hypothesis, combination experiments performed by using different doses of DP in the presence of 158 nM GSK983 in 20 µM uridine supplemented media revealed synergy of these compounds for killing A549 lung cancer cell line (FIG. 14, $IC_{50}$(DP) of 230 nM). Similar effect was observed on MV4-11 cells, biphenotypic B myelomonocytic leukemia cell, with $IC_{50}$(DP) of 110 nM in the presence of 158 nM GSK983 in 20 µM uridine supplemented media.

UCK2 is highly expressed in many cancer tissues therefore, specifically inhibiting UCK2 in combination with inhibiting de novo pyrimidine synthesis pathway can provide for better toxicity profiles.

Materials and Methods

Chemicals and Reagents for Biological Assays

GSK983 was synthesized as described in example 1. GSK983 was dissolved in DMSO to prepare stock solutions which were diluted in the appropriate cell growth medium for biological assays. GSK983 stock solutions in DMSO were stored at −80° C. Uridine, was obtained from Sigma-Aldrich. For pyrimidine supplementation experiments, pyrimidine metabolites uridine was dissolved directly in the appropriate growth medium (RPMI or DMEM). 5-Ethynyl uridine (EU) and Azide-fluor 488 were obtained from Sigma-Aldrich and dissolved in DMSO to prepare working stock solutions.

Cell culture K562 cells (ATCC) were cultured in RPMI (Gibco) supplemented with 10% fetal bovine serum (FBS), penicillin/streptomycin, and L-glutamine. HeLa cells (HeLa-Kyoto cells, a gift from AA Hyman) and A549 cells (ATCC) were cultured in DMEM (Gibco) supplemented with 10% FBS, penicillin/streptomycin, and L-glutamine. In biological assays, A549 cells were detached from the growth surface using a trypsin/EDTA solution (Gibco) prior to analysis. Cells were maintained in logarithmic growth during all biological assays. All cell lines were maintained in a humidified incubator (37° C., 5% CO2), and checked regularly for mycoplasma contamination.

Generation of UCK2 knockdown cell lines. Two UCK2 shRNA-expressing K562 and A549 derivatives were constructed. Pairs of oligonucleotides encoding shRNAs with the identification sequences of ATGACCACCTGCTTCTG-GCGAT (1) and 1TTTGAGAATGAGTTCATTGTCA (2)' targeting UCK2 gene were annealed and ligated into the pMK1200 (pMCB246) vector backbone, which was previously digested with BstXl and gel-purified. pMK1200 (pMCB246) encodes two BstXl cut sites, puromycin resistance, and mCherry. Oligonucleotides were obtained from Integrated DNA Technologies (IDT).

To produce lentivirus for individual shRNA tests, Mirus transfection reagent (catalog number MIR2305) (2.5 µL) was added to DMEM containing no FBS (97.5 µL) and incubated at room temperature for 5 min. Meanwhile, pMCB309 containing the indicated shRNA-encoding insert (0.75 µg) was combined with 3rd generation lentiviral packaging components (pMDL, pRSV, and pMD2—available from Addgene) (0.75 µg). The total DNA mixture (pMCB246 with shRNA encoding insert+lentiviral packaging components) was added to the DMEM/Virus mixture and incubated for 30 min at room temperature. Meanwhile, HEK293T cells were seeded into 6-well plates at a density of 1 million cells/well in 2 mL DMEM. Transfection mixtures were added to HEK293T cells dropwise and cells were incubated for 24 h at 37° C. The following day, cells were supplemented with 3 mL fresh DMEM. Cells were incubated at 37° C. for an additional 48 h. To harvest the virus, the supernatant was collected and passed through a 0.45 µm syringe filter.

To infect both A549 and K562 cells with lentivirus, the cells were seeded into 24-well plates at a density of 100,000 cells/well in a volume of 100 µL. Polybrene (2 µL of a 4 mg/mL stock solution) was added to the cells, followed by 1 mL of the appropriate lentivirus stock. Cells were spin infected in 24-well plates for 2 h at 1000 g at 33° C. Following spin infection, cells were resuspended and pelleted (300 g, 5 min). The supernatant was removed by aspiration and the cells were resuspended in fresh DMEM or RPMI growth medium and incubated for 72 h at 37° C. The cells were expanded into 6-well plates and grown in the presence of puromycin (0.5 and 1.0 µg/mL respectively) for 3-5 days to select for infected cells. Following puromycin selection, cells were pelleted (300 g, 5 min) and resuspended in fresh DMEM or RPMI growth medium and further selected for the highest mCherry labeling using fluorescence-activated cell sorting (FACS).

Figure 11C:
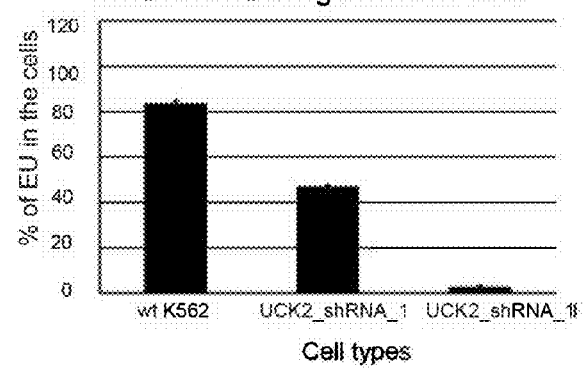

DENV antiviral assays with A549 UCK2 knockdown cells is performed with the pDENV-Luc infectious clone as described above. For DENV inhibition assays (FIG. 11), human wild type A549 cells, and A549 cells with UCK2 shRNA-2 were seeded into 24-well plates at a density of 20,000 cells/well and incubated for 24 h. The cells were treated with DMEM containing 20 µM Uridine supplied with or without 48 nM GSK983 for 4 h at 37° C. Growth medium containing uridine and/or GSK983 was removed and cells were incubated for 1 h with DENV-Luc (no GSK983 or uridine) at 37° C. Following DENV-Luc incubation, cells were washed with 1×PBS and treated with fresh DMEM containing 48 nM GSK983 and 20 µM uridine or only 20 µM uridine. Cells were incubated at 37° C. for an additional 72 h. DENV-Luc replication was monitored by the production of *Renilla* luciferase, which was measured using the *Renilla*-Glo Luciferase Assay System (Promega) according to the specifications of the manufacturer. For the accompanying cell viability assay, A549 cells were treated the same way except the viral infection procedure. Following 72 h treatment, cells were harvested and the density of viable cells was determined by flow cytometry (FSC/SSC) using a BD Accuri C6 Flow Cytometer.

DENV Antiviral Assays for Testing Combination of GSK983 and DP Inhibition. DENV antiviral assays were performed with the pDENV-Luc infectious clone as described above. For DENV inhibition assays (FIG. 12), human wild type A549 cells were seeded into 24-well plates at a density of 20,000 cells/well and incubated for 24 h. The cells were treated with DMEM containing 20 µM uridine supplied with 48 nM GSK983 and specified DP concentrations (1 ml for each well) for 4 h at 37° C. Then, the DENV-Luc was added into each well (10 µl) and the cells were incubated at 37° C. for an additional 72 h. DENV-Luc replication was monitored by the production of *Renilla* luciferase, which was measured using the *Renilla*-Glo Luciferase Assay System (Promega) according to the specifications of the manufacturer. For the accompanying cell viability assay, A549 cells were treated the same way except the viral infection procedure. Following 48 h or 72 h treatment, cells were harvested and the density of viable cells was determined by flow cytometry (FSC/SSC) using a BD Accuri C6 Flow Cytometer.

Cell cycle analysis based on 5-ethynyl-uridine (EU) incorporation.

A549 or K562 cells were treated with indicated concentrations of DP, or neither (untreated) for 4 h. Cells were seeded into 6-well plates at a density of 400,000 cells/mL at the time of the assay. The final concentration of DMSO in each well was <0.1%. After 15 h incubation with DP, cells were treated with 200 µM EU in DMEM (No FBS) for 30 min. EU-treated cells were harvested, pelleted (300 g, 5 min), washed (0.5 mL 1×PBS), and resuspended in 70% EtOH (1 mL, 0° C.) with mild vortexing. Cells were fixed in 70% EtOH overnight at 4° C. The following day, fixed cells were pelleted (1900 g, 5 min), washed (0.5 mL 1×PBS) and resuspended in 200 µL of a freshly prepared EU labeling solution containing Tris-HCl (100 mM, pH 8.5), $CuSO_4$ (1 mM), ascorbic acid (100 mM), and the azide-functionalized fluorophore Azide-fluor 488 (10 µM). Cells were incubated in the EU labeling solution in the dark at room temperature for 30 min. The cells were pelleted (475 g, 5 min), and the supernatant was removed by vacuum. Cells were washed twice (0.5 mL 1×PBS for each wash) and analyzed by flow cytometry using a BD Accuri C6 Flow Cytometer. Azide-fluor 488 fluorescence was detected in FL1.

Mouse Experiments. AG129B6 mice (129/Sv mice lacking alpha/beta interferon [IFN-α] and IFN-β receptors) were retro-orbitally infected with $4\times10^6$ PFU/mouse and dosed with 10 mg/kg GSK983 and 50 mg/kg DP b.i.d via intraperitoneal injection of individual drugs (i.p). The analysis of viral titers from spleens harvested at 4 days post-infection was performed as described in 'Mateo R, Nagamine C M, Kirkegaard K. 2015. Suppression of drug resistance in dengue virus. mBio 6(6):e01960-15. doi:10.1128/mBio.01960-15'.

A459 and K562 Cell Count Experiments. Human wild type A549 cells were seeded into 24-well plates at a density of 20,000 cells/well and incubated for 24 h. The cells were treated with DMEM containing 20 μM uridine supplied with 158 nM GSK983 and specified DP concentrations (1 ml for each well). Following 72 h treatment at 37° C., the cells were harvested and the density of viable cells was determined by flow cytometry (FSC/SSC) using a BD Accuri C6 Flow Cytometer.

Similarly, human wild type K562 cells were seeded into 24-well plates at a density of 50,000 cells/well and incubated for 24 h. The cells were treated with DMEM containing 20 μM uridine supplied with 50 nM GSK983 and specified NBMPR concentrations (1 ml for each well). Following 72 h treatment at 37° C., the cells were harvested and the density of viable cells was determined by flow cytometry (FSC/SSC) using a BD Accuri C6 Flow Cytometer.

What is claimed is:

1. A pharmaceutical formulation comprising:
   (i) an effective dose of an inhibitor of dihydroorotate dehydrogenase (DHODH) having a structure of Formula 1:

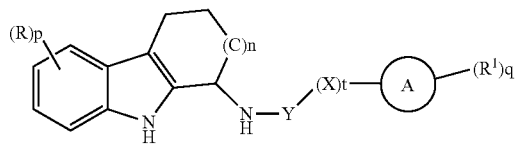

(I)

wherein: n is 0, 1, or 2; t is 0 or 1; X is —NH—, —O—, —$R^{10}$—, —O$R^{10}$—, $R^{10}$O—, —$R^{10}$O$R^{10}$—, —N$R^{10}$—, —$R^{10}$N—, —$R^{10}$N$R^{10}$—, —$R^{10}$S(O)$_m$—, or —$R^{10}$S(O)$_m$$R^{10}$—; Y is —C(O)— or —S(O)$_m$—; each R is the same or different and is independently selected from the group consisting of halogen, haloalkyl, alkyl, alkenyl, alkynyl, cycloalkyl, cycloalkenyl, —$R^{10}$cycloalkyl, Ay, —NH$R^{10}$Ay, Het, —NHHet, —NH$R^{10}$Het, —O$R^2$, —OAy, —OHet, —$R^{10}$O$R^2$, —N$R^2R^3$, —N$R^2$Ay, —$R^{10}$N$R^2R^3$, —$R^{10}$N$R^2$Ay, —$R^{10}$C(O)$R^2$, —C(O)$R^2$, —CO$_2R^2$, —$R^{10}$CO$_2R^2$, —C(O)N$R^2R^3$, —C(O)Ay, —C(O)N$R^2$Ay, —C(O)Het, —C(O)NH$R^{10}$Het, —$R^{10}$C(O)N$R^2R^3$, —C(S)N$R^2R^3$, —$R^{10}$C(S)N$R^2R^3$, —$R^{10}$NHC(NH)N$R^2R^3$, —C(NH)N$R^2R^3$, —$R^{10}$C(NH)N$R^2R^3$, —S(O)$_2$NR$^2$R$^3$, —S(O)$_2$NR$^2$Ay, —R$^{10}$SO$_2$NHCOR$^2$,
—R$^{10}$SO$_2$NR$^2$R$^3$, —R$^{10}$SO$_2$R$^2$, —S(O)$_m$R$^2$, —S(O)$_m$Ay, cyano, nitro, or azido;

each R$^1$ is the same or different and is independently selected from the group consisting of halogen, haloalkyl, alkyl, alkenyl, alkynyl, cycloalkyl, cycloalkenyl, —R$^{10}$cycloalkyl, Ay, —NHR$^{10}$Ay, Het, —NHHet, —NHR$^{10}$Het, —OR$^2$, —OAy, —OHet, —R$^{10}$OR$^2$, —NR$^2$R$^3$, —NR$^2$Ay, —R$^{10}$NR$^2$R$^3$, —R$^{10}$NR$^2$Ay, —R$^{10}$C(O)R$^2$, —C(O)R$^2$, —CO$_2$R$^2$, —R$^{10}$CO$_2$R$^2$, —C(O)NR$^2$R$^3$, —C(O)Ay, —C(O)NR$^2$Ay, —C(O)Het, —C(O)NHR$^{10}$Het, —R$^{10}$C(O)NR$^2$R$^3$, —C(S)NR$^2$R$^3$, —R$^{10}$C(S)NR$^2$R$^3$, —R$^{10}$NHC(NH)NR$^2$R$^3$, —C(NH)NR$^2$R$^3$, —R$^{10}$C(NH)NR$^2$R$^3$, —S(O)$_2$NR$^2$R$^3$, —S(O)$_2$NR$^2$Ay, —R$^{10}$SO$_2$NHCOR$^2$, —R$^{10}$SO$_2$NR$^2$R$^3$, —R$^{10}$SO$_2$R$^2$, —S(O)$_m$R$^2$, —S(O)$_m$Ay, cyano, nitro, or azido;

each m independently is 0, 1, or 2;

each R$^{10}$ is the same or different and is independently selected from alkylene, cycloalkylene, alkenylene, cycloalkenylene, and alkynylene;

p and q are each independently selected from 0, 1, 2, 3, 4, or 5;

each of R$^2$ and R$^3$ are the same or different and are independently selected from the group consisting of H, alkyl, alkenyl, alkynyl, cydoalkyl, cydoalkenyl, —R$^{10}$cycloalkyl, —R10OH, —R$^{10}$(OR$^{10}$)$_w$, and —R$^{10}$NR$^4$R$^5$;

w is 1-10;

each of R$^4$ and R$^5$ are the same or different and are independently selected from the group consisting of alkyl, cycloalkyl, alkenyl, cycloalkenyl, and alkynyl;

Ay represents an aryl group;

Het represents a 5- or 6-membered heterocyclyl or heteroaryl group;

ring A is aryl or heteroaryl, provided that when the A ring is aryl, t is 0, and Y is SO$_2$, then p is not 0;

including salts and solvates thereof;

or brequinar; and (ii) an effective dose of dipyridamole;

wherein the formulation provides for reduced toxicity toward host cells relative to administration of the DHODH inhibitor as a single agent.

2. The pharmaceutical formulation of claim 1, wherein the DHODH inhibitor is selected from the group consisting of GSK983, GSK984, 6Br-oTol and 6Br-pF, as depicted below.

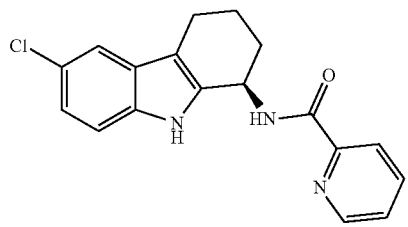

GSK983

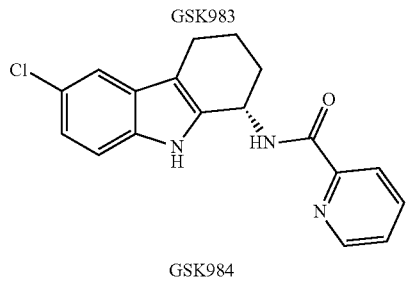

GSK984

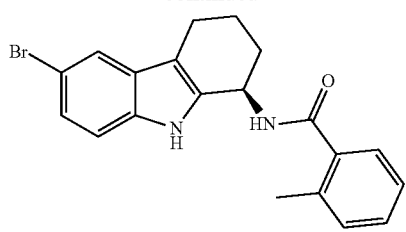

6Br-oTol

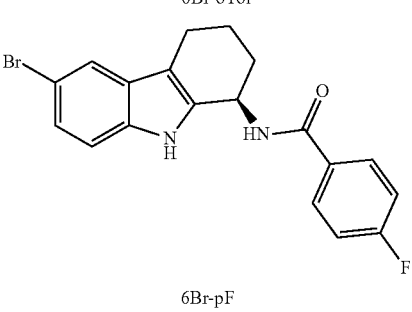

6Br-pF

3. The formulation of claim 1, further comprising a nucleoside or nucleotide analog inhibitor of uridine cytidine kinase selected from the group consisting of 5'-azido-5'-deoxycytidine, 5'-azido-5'-deoxyuridine, 5'-iodo-5'-deoxyuridine, -5'-azido-5'-deoxy-6-azauridine, 5-O-nitrouridine, 5-O-nitro-5-fluorouridine, 5-azacytidine 5'-triphosphate, and 5-nitrouridine.

4. The formulation of claim 1, further comprising cyclopentenyluridine or cyclopentenylcytidine.

5. The formulation of claim 1 wherein the combination of dipyridamole and the DHODH inhibitor has a cellular toxicity profile on human cells that provides for a reduction in toxicity of at least 50% less toxic than the DHODH inhibitor administered as a single agent.

6. The formulation of claim 1 wherein the combination of dipyridamole and the DHODH inhibitor has a cellular toxicity profile on human cells that provides for a reduction in toxicity of at least 90% less toxic than the DHODH inhibitor administered as a single agent.

7. A method of inhibiting pathogenic RNA virus proliferation in a subject, in need thereof, the method comprising:

administering to a subject an effective amount of a formulation comprising an effective dose of (i) an inhibitor of DHODH, wherein the DHODH inhibitor is selected from the group consisting of GSK983, 6Br-pF, 6Br-oTol and GSK984, as depicted below, and (ii) an effective dose of dipyridamole;

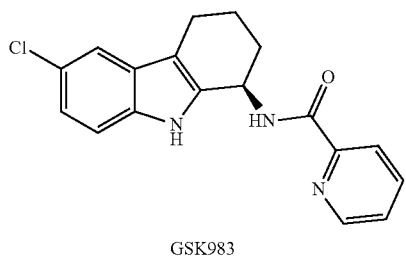

GSK983

-continued

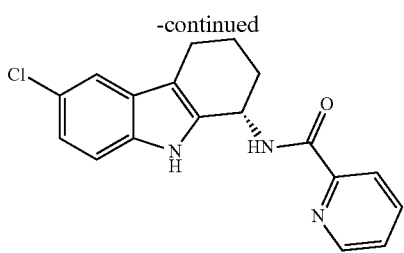

GSK984

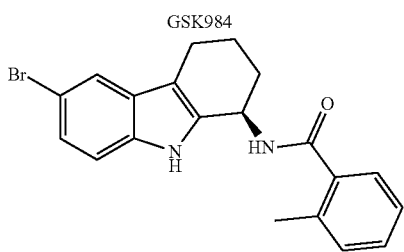

6Br-oTol

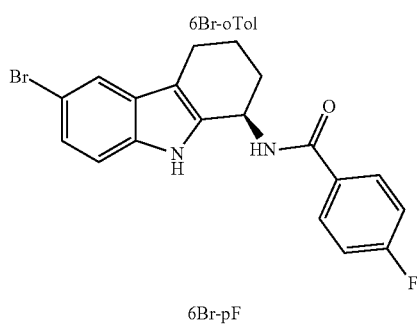

6Br-pF wherein the formulation provides for reduced toxicity toward the subject relative to administration of the DHODH inhibitor as a single agent.

8. The method of claim 7, wherein the subject is a mammal.

9. The method of claim 8, wherein the mammal is a human.

10. The method of Claim 7, wherein the RNA virus is a retrovirus.

11. The method of claim 7, wherein the subject is infected with the virus.

12. The method of claim 7, wherein the subject has been exposed to the virus.

13. The method of claim 7 wherein the combination of dipyridamole and the DHODH inhibitor has a cellular toxicity profile on human cells that provides for a reduction in toxicity of at least 50% less toxic than the DHODH inhibitor administered as a single agent.

14. The method of claim 7 wherein the combination of dipyridamole and the DHODH inhibitor has a cellular toxicity profile on human cells that provides for a reduction in toxicity of at least 90% less toxic than the DHODH inhibitor administered as a single agent.

* * * * *